(12) United States Patent
Shintou et al.

(10) Patent No.: US 9,801,960 B2
(45) Date of Patent: *Oct. 31, 2017

(54) PROBE FOR A BIOLOGICAL SPECIMEN AND LABELLING METHOD AND SCREENING METHOD USING THE PROBE

(71) Applicant: CANON KABUSHIKI KAISHA, Tokyo (JP)

(72) Inventors: Taichi Shintou, Saitama (JP); Takeshi Miyazaki, Yokohama (JP); Masashi Hirose, Machida (JP); Taketoshi Okubo, Asaka (JP); Kohei Watanabe, Yokohama (JP); Tsuyoshi Nomoto, Tokyo (JP); Toshio Tanaka, Tsu (JP); Yuhei Nishimura, Tsu (JP); Yasuhito Shimada, Tsu (JP); Norihiro Nishimura, Tsu (JP)

(73) Assignee: CANON KABUSHIKI KAISHA, Tokyo (JP)

(*) Notice: Subject to any disclaimer, the term of this patent is extended or adjusted under 35 U.S.C. 154(b) by 42 days.

This patent is subject to a terminal disclaimer.

(21) Appl. No.: 14/624,558

(22) Filed: Feb. 17, 2015

(65) Prior Publication Data
US 2015/0157745 A1 Jun. 11, 2015

Related U.S. Application Data

(62) Division of application No. 13/133,381, filed as application No. PCT/JP2009/071866 on Dec. 24, 2009.

(30) Foreign Application Priority Data

Dec. 25, 2008 (JP) ................ 2008-330987

(51) Int. Cl.
| | |
|---|---|
| *A61K 49/00* | (2006.01) |
| *C07D 209/56* | (2006.01) |
| *C07D 209/58* | (2006.01) |
| *C07D 401/02* | (2006.01) |
| *C07D 417/02* | (2006.01) |
| *A61K 51/04* | (2006.01) |
| *C07D 209/08* | (2006.01) |
| *C07D 209/86* | (2006.01) |
| *C07D 209/94* | (2006.01) |
| *C07D 401/08* | (2006.01) |
| *C07D 403/06* | (2006.01) |
| *C07D 403/08* | (2006.01) |
| *C07D 413/08* | (2006.01) |
| *C07D 417/06* | (2006.01) |

(Continued)

(52) U.S. Cl.
CPC ...... *A61K 51/0453* (2013.01); *A61K 49/0002* (2013.01); *A61K 49/006* (2013.01); *A61K 49/0008* (2013.01); *A61K 49/0021* (2013.01); *A61K 49/10* (2013.01); *C07D 209/08* (2013.01); *C07D 209/86* (2013.01); *C07D 209/94* (2013.01); *C07D 401/08* (2013.01); *C07D 403/06* (2013.01); *C07D 403/08* (2013.01); *C07D 413/08* (2013.01); *C07D 417/06* (2013.01); *C07D 417/14* (2013.01); *C09B 23/0091* (2013.01); *C09B 23/04* (2013.01); *C09B 23/105* (2013.01); *G01N 33/582* (2013.01); *G01N 2333/4603* (2013.01); *G01N 2500/10* (2013.01)

(58) Field of Classification Search
None
See application file for complete search history.

(56) References Cited

U.S. PATENT DOCUMENTS

| | | |
|---|---|---|
| 4,366,314 A | 12/1982 | Beecken |
| 5,370,842 A | 12/1994 | Miyazaki et al. |

(Continued)

FOREIGN PATENT DOCUMENTS

| | | |
|---|---|---|
| CN | 1887883 A | 1/2007 |
| CN | 101100465 A | 1/2008 |

(Continued)

OTHER PUBLICATIONS

Definition of "Hair cell" from the http://medical-dictionary.thefreedictionary.com/, accessed Mar. 16, 2017.*

(Continued)

*Primary Examiner* — Nissa Westerberg
(74) *Attorney, Agent, or Firm* — Fitzpatrick, Cella, Harper & Scinto

(57) ABSTRACT

Provided is a novel probe for a biological specimen for labelling by itself and clearly visualizing one of a specific cell and a specific cell organ in a living body, the probe having excellent spectral characteristics and exhibiting excellent storage stability. The probe for a biological specimen contains, as an active agent, at least one kind of compound represented by a general formula (I).

(Chem 1)

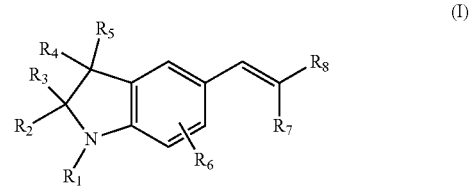

12 Claims, 3 Drawing Sheets

(51) Int. Cl.
| | | |
|---|---|---|
| C07D 417/14 | (2006.01) | |
| C09B 23/01 | (2006.01) | |
| C09B 23/04 | (2006.01) | |
| C09B 23/10 | (2006.01) | |
| G01N 33/58 | (2006.01) | |
| A61K 49/10 | (2006.01) | |

(56) References Cited

U.S. PATENT DOCUMENTS

| | | |
|---|---|---|
| 5,380,490 A | 1/1995 | Hoshi et al. |
| 5,512,446 A | 4/1996 | Miyazaki et al. |
| 5,534,441 A | 7/1996 | Miyazaki et al. |
| 5,601,983 A | 2/1997 | Takayama et al. |
| 5,624,798 A | 4/1997 | Yamamoto et al. |
| 5,653,675 A | 8/1997 | Kanno et al. |
| 5,670,315 A | 9/1997 | Yamamoto et al. |
| 5,679,516 A | 10/1997 | Okamoto et al. |
| 5,679,581 A | 10/1997 | Miyazaki et al. |
| 5,700,647 A | 12/1997 | Miyazaki et al. |
| 5,846,730 A | 12/1998 | Miyazaki et al. |
| 5,863,789 A | 1/1999 | Komatsu et al. |
| 5,944,882 A | 8/1999 | Shinozaki et al. |
| 6,022,961 A | 2/2000 | Yamamoto et al. |
| 6,424,418 B2 | 7/2002 | Kawabata et al. |
| 6,472,191 B1 | 10/2002 | Yano et al. |
| 6,686,439 B2 | 2/2004 | Kenmoku et al. |
| 6,803,444 B2 | 10/2004 | Suzuki et al. |
| 6,853,477 B2 | 2/2005 | Nomoto et al. |
| 6,858,417 B2 | 2/2005 | Yano et al. |
| 6,861,496 B2 | 3/2005 | Kenmoku et al. |
| 6,864,074 B2 | 3/2005 | Yano et al. |
| 6,916,861 B2 | 7/2005 | Nomoto et al. |
| 6,951,745 B2 | 10/2005 | Nomoto et al. |
| 7,153,622 B2 | 12/2006 | Honma et al. |
| 7,235,396 B2 | 6/2007 | Nomoto et al. |
| 7,354,995 B2 | 4/2008 | Imamura et al. |
| 7,399,644 B2 | 7/2008 | Honma et al. |
| 7,419,820 B2 | 9/2008 | Watanabe et al. |
| 7,524,659 B2 | 4/2009 | Nomoto et al. |
| 7,527,963 B2 | 5/2009 | Nomoto et al. |
| 7,615,233 B2 | 11/2009 | Yano et al. |
| 7,615,640 B2 | 11/2009 | Horiuchi et al. |
| 7,632,618 B2 | 12/2009 | Nomoto et al. |
| 7,846,727 B2 | 12/2010 | Nishiguchi et al. |
| 7,875,465 B2 | 1/2011 | Shiotsuka et al. |
| 7,919,263 B2 | 4/2011 | Shiotsuka et al. |
| 7,960,168 B2 | 6/2011 | Watanabe et al. |
| 7,972,792 B2 | 7/2011 | Fujimoto et al. |
| 7,989,219 B2 | 8/2011 | Shiotsuka et al. |
| 2004/0220235 A1 | 11/2004 | Augelli-Szafran et al. |
| 2004/0256002 A1 | 12/2004 | Horiuchi et al. |
| 2005/0090671 A1* | 4/2005 | Chang .............. C07D 403/14 548/311.7 |
| 2005/0249669 A1 | 11/2005 | Chang et al. |
| 2006/0171946 A1* | 8/2006 | Sabbadini .......... A61K 31/685 424/145.1 |
| 2007/0190590 A1 | 8/2007 | Kubo et al. |
| 2007/0259394 A1 | 11/2007 | Kanome et al. |
| 2008/0064037 A1 | 3/2008 | Chang et al. |
| 2009/0134042 A1 | 5/2009 | Nomoto et al. |
| 2009/0233280 A1 | 9/2009 | Nomoto et al. |
| 2010/0151510 A1 | 6/2010 | Kanome et al. |
| 2010/0166663 A1 | 7/2010 | Nomoto et al. |
| 2011/0079223 A1 | 4/2011 | Masada et al. |
| 2011/0102495 A1 | 5/2011 | Kaneko et al. |
| 2011/0152123 A1 | 6/2011 | Nishiguchi et al. |
| 2011/0189096 A1 | 8/2011 | Watanabe et al. |
| 2011/0236310 A1 | 9/2011 | Watanabe et al. |
| 2012/0207683 A1 | 8/2012 | Tanaka et al. |
| 2013/0280169 A1 | 10/2013 | Watanabe et al. |
| 2014/0017722 A1 | 1/2014 | Watanabe et al. |

FOREIGN PATENT DOCUMENTS

| | | |
|---|---|---|
| EP | 1 526 159 A1 | 4/2005 |
| JP | 62-502548 A | 10/1987 |
| JP | 63-28932 B2 | 6/1988 |
| JP | 2-84390 A | 3/1990 |
| JP | 10-181210 A | 7/1998 |
| JP | 2002-514470 A | 5/2002 |
| JP | 2002-514471 A | 5/2002 |
| JP | 2008-522953 A | 7/2008 |
| WO | 86/06374 A1 | 11/1986 |
| WO | 99/58159 A1 | 11/1999 |
| WO | 99/58160 A1 | 11/1999 |
| WO | 2004/011555 A1 | 2/2004 |
| WO | 2006/062233 A1 | 6/2006 |
| WO | 2009/128266 A1 | 10/2009 |

OTHER PUBLICATIONS

Definition of "ex vivo" from the http://medical-dictionary.thefreedictionary.com/, accessed Mar. 16, 2017.*

PCT International Search Report and Written Opinion of the International Searching Authority, International Application No. PCT/JP2009/071866, dated Mar. 9, 2010.

Haglund, MD,., Phil, et al. "Enhanced Optical Imaging of Rat Gliomas and Tumor Margins", Neurosurgery, vol. 35, No. 5, Nov. 1994, pp. 930-941

Kiesslich, et al., "Confocal Laser Endoscopy for Diagnosing Intraepithelial Neoplasias and Colorectal Cancer in Vivo", Gastroenterology, vol. 127, No. 3, 2004, pp. 706-713.

Li, et al., "Tumor Localization Using Fluorescence of Indocyanine Green (ICG) in Rat Models", SPIE, vol. 2389, 1995, pp. 789-797.

Gawinecki, et al., "The effect of the amino group on the spectral properties of substituted styrylpyridinium salts", Dyes and Pigments, vol. 45, 2000, pp. 103-107.

Horiuchi, et al., "Highly-efficient metal-free organic dyes for dye-sensitized solar cells", Chem. Commun., vol. 24, 2003, pp. 3036-3037.

Yang, et al., "Substituent-Dependent Photoinduced Intramolecular Charge Transfer in N-Aryl-Substituted trans-4-Aminostilbenes", J. Am. Chem. Soc., vol. 126, 2004, pp. 12325-12335.

Zhang, et al., "Synthesis of N-Vinylcarbazole Derivatives with Acceptor Groups", Tetrahedron Letters, vol. 38, No. 50, 1997, pp. 8721-8722.

Mahboobi, et al., "2-Aroylindoles and 2-Aroylbenzofurans with N-Hydroxyacrylamide Substructures as a Novel Series of Rationally Designed Histone Deacetylase Inhibitors", J. Med. Chem., vol. 50, 2007, pp. 4405-4418.

Pete, et al., "Synthesis of 5-Substituted Indole Derivatives, Part 5. A Synthesis of 5-Formyl-1H-Indole-2-Carboxylates: The CH2SO3H Functionality as a Masked Formyl Group", Herterocycles, vol. 60, No. 12, 2003, pp. 2761-2765.

European Search Report dated Jul. 17, 2012 in European Application No. 09835114.1.

Chang, et al., "A Novel Carbazole Derivative, BMVC: a Potential Antitumor Agent and Fluorescence Marker of Cancer Cells", Chemistry & Biodiversity, vol. 1, No. 9, 2004, pp. 1377-1384.

Kang, et al., "A Dual Selective Antitumor Agent and Fluorescence Probe: The Binary BMVC—Porphyrin Photosensitizer", ChemMedChem, vol. 3, No. 5, 2008, pp. 725-728.

Wang, et al., "Diversity-Oriented Fluorescence Library Approach (DOFLA) to the Discovery of Chymotrypsin Sensor", Journal of Combinatorial Chemistry, vol. 10, No. 3, 2008, pp. 460-465.

Hassner, et al., "Charge-Shift Probes of Membrane Potential, Synthesis", Journal of Organic Chemistry, vol. 49, No. 14, 1984, pp. 2546-2551.

Fluhler, et al., "Spectra, Membrane Binding, and Potentiometric Responses of New Charge Shift Probes", Biochemistry, vol. 24, No. 21, 1985, pp. 5749-5755.

Tsai, et al., "Effect of different electronic properties on 9-aryl-substituted BMVC derivatives for new fluorescence probes", Journal of Luminescence, vol. 127, No. 1, 2007, pp. 41-47.

(56) References Cited

OTHER PUBLICATIONS

European Office Action dated Apr. 29, 2013 in European Application No. 09 835 114.1.
European Office Action dated May 23, 2014 in European Application No. 09835114.1.
Wang, et al., "Combinatorial Synthesis of Benzimidazolium Dyes and Its Diversity Directed Application toward GTP-Selective Fluorescent Chemosensors", J. American Chemical Society, vol. 128, No. 32, 2006, pp. 10380-10381.
Jansma, et al., "Automated Microflow NMR: Routine Analysis of Five-Microliter Samples", Analytical Chemistry, vol. 77, No. 19, 2005, pp. 6509-6515.

* cited by examiner

PROBE FOR A BIOLOGICAL SPECIMEN AND LABELLING METHOD AND SCREENING METHOD USING THE PROBE

This application is a divisional of application Ser. No. 13/133,381, which was the National Stage of International Application No. PCT/JP2009/071866, filed Dec. 24, 2009.

TECHNICAL FIELD

The present invention relates to a probe for a biological specimen for labelling a biological specimen in a simple manner and with high sensitivity, and a labelling method and a screening method using the probe.

BACKGROUND ART

Molecular imaging is means for forming an image for observing a biological activity at cellular and molecular levels. The advances in molecular imaging technologies of recent years allow various cellular and molecular behaviors in a living body to be observed from the outside (captured as images), resulting in that the molecular imaging becomes important means for a diagnostic technology in a medical area and for research in a life science area.

Magnetic resonance imaging (MRI), positron emission tomography (PET), and optical topography are mainly studied as techniques of the molecular imaging, and widely utilized in the medical area and in the life science area depending on the purposes. Of those, a molecular imaging technology with PET is widely employed for early diagnosis of tumors and exploratory studies on drug candidates, as means for labelling a specific biomolecule by using a probe. Further, a technology of visualizing a cell and a molecule in a living body with a staining compound allows capturing of changes in a cell and a molecule within a living body in a simple manner, and hence has attracted attention as an important technology in analysis of life phenomena, early diagnosis of various diseases, application to the field of drug discovery, and the like. A staining method of visualizing one of a cell and a tissue has been long known, and various staining agents are used depending on the purposes. For example, fluorescence staining agents such as fluorescein are used for microangiography of the retina (see Neurosurgery, 35, p. 930, 1994) and fundoscopy (see Gastroenterology, 127(3), pp. 706-713, 2004). However, there has been a problem that the fluorescence sensitivity is not sufficient, and a stained site cannot clearly detected owing to scattering by a body tissue. Further, there has been a problem that indocyanine green as a cyanine-based dye does not exhibit sufficient fluorescence intensity in many cases in the above-mentioned applications (see SPIE, 2389, pp. 789-797, 1995), and hence needs to be used in a large amount to increase the sensitivity, with a result that an unnecessary portion may be stained. In addition, there has been a problem that the compound has low light fastness, and hence tends to be discolored during observation. Therefore, there is a demand for the development of a novel fluorescent dye having high luminance and satisfactory light fastness.

DISCLOSURE OF THE INVENTION

It is an object of the present invention to provide a novel probe for a biological specimen, which has excellent spectral characteristics and also exhibits excellent storage stability.

It is another object of the present invention to provide a labelling method for a cell or a cell organ in vivo, ex vivo, and in vitro by using the novel probe for a biological specimen. Further, it is still another object of the present invention to provide a screening method using the novel probe for a biological specimen.

The inventors of the present invention have intensively studied in order to solve the above-mentioned problems, and have succeeded in obtaining a probe for a biological specimen which contains, as an active agent, at least one kind of compound represented by the following general formula (I). In addition, the inventors have established a labelling method for a cell and a cell tissue in vivo, ex vivo, and in vitro by using the probe for a biological specimen. That is, the present invention is as follows.

The present invention relates to a probe for a biological specimen including, as an active agent, at least one kind of compound represented by the general formula (I).

(Chem 1)

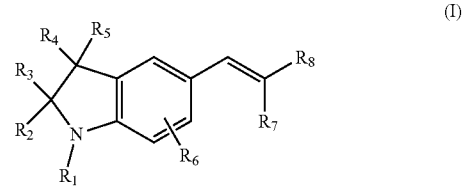

(I)

In the general formula (I): $R_1$ represents one of a hydrogen atom, an alkyl group, an aralkyl group, an alkenyl group, an aryl group, a heterocyclic group, and an acyl group; $R_2$ to $R_5$ each independently represent one of a hydrogen atom, an alkyl group, an aryl group, a carboxylic acid group, a carboxylic acid ester group, and an acyl group, and $R_2$ and $R_4$ may be bonded to each other to form a ring; and $R_6$ represents one of a hydrogen atom, an alkyl group, an alkoxy group, and a halogen atom, $R_7$ and $R_8$ each independently represent one of a hydrogen atom, an alkenyl group, a cyano group, a carboxylic acid group, a carboxylic acid ester group, a sulfonic acid group, an acyl group, and a heterocyclic group, and $R_7$ and $R_8$ may be bonded to each other to form a ring.

A labelling method for a biological specimen according to the present invention is a labelling method involving labelling by bringing a biological specimen into contact with the above-mentioned probe for a biological specimen.

A screening method according to the present invention is a screening method using the probe for a biological specimen.

A diagnostic probe according to the present invention is a diagnostic probe including, as an active agent, the probe for a biological specimen.

A diagnostic device according to the present invention is a diagnostic device including the probe for a biological specimen.

Further, the present invention includes the use of the compound represented by the above general formula (I) as a label for a biological specimen.

The present invention provides a probe for a biological specimen for labelling a biological specimen in a simple manner and with high sensitivity, the probe exhibiting high storage stability and having a large Stokes' shift. Further, the labelling of a cell or a cell organ with high sensitivity enables the imaging of morphological features such as size and shape. In particular, the progression and cure of a disease can be objectively evaluated by imaging a disease-related site and monitoring its time-dependent change. The probe is also applicable to a technology of selectively imaging a specific body tissue at a molecular level. Further, the speed of drug development including screening becomes faster, with the result that a cost reduction can be achieved. The probe is also applicable to the high precision diagnosis of new diseases and the development of treatment method for the new diseases. Further, the probe is expected to be used as an index in screening for safety evaluation of a chemical substance. In addition, the probe may be used, for example, for life science research to understand unexplained phenomena, and thus, may become an effective basic technology that dramatically develops the industry.

DESCRIPTION OF THE EMBODIMENTS

Figure 1:
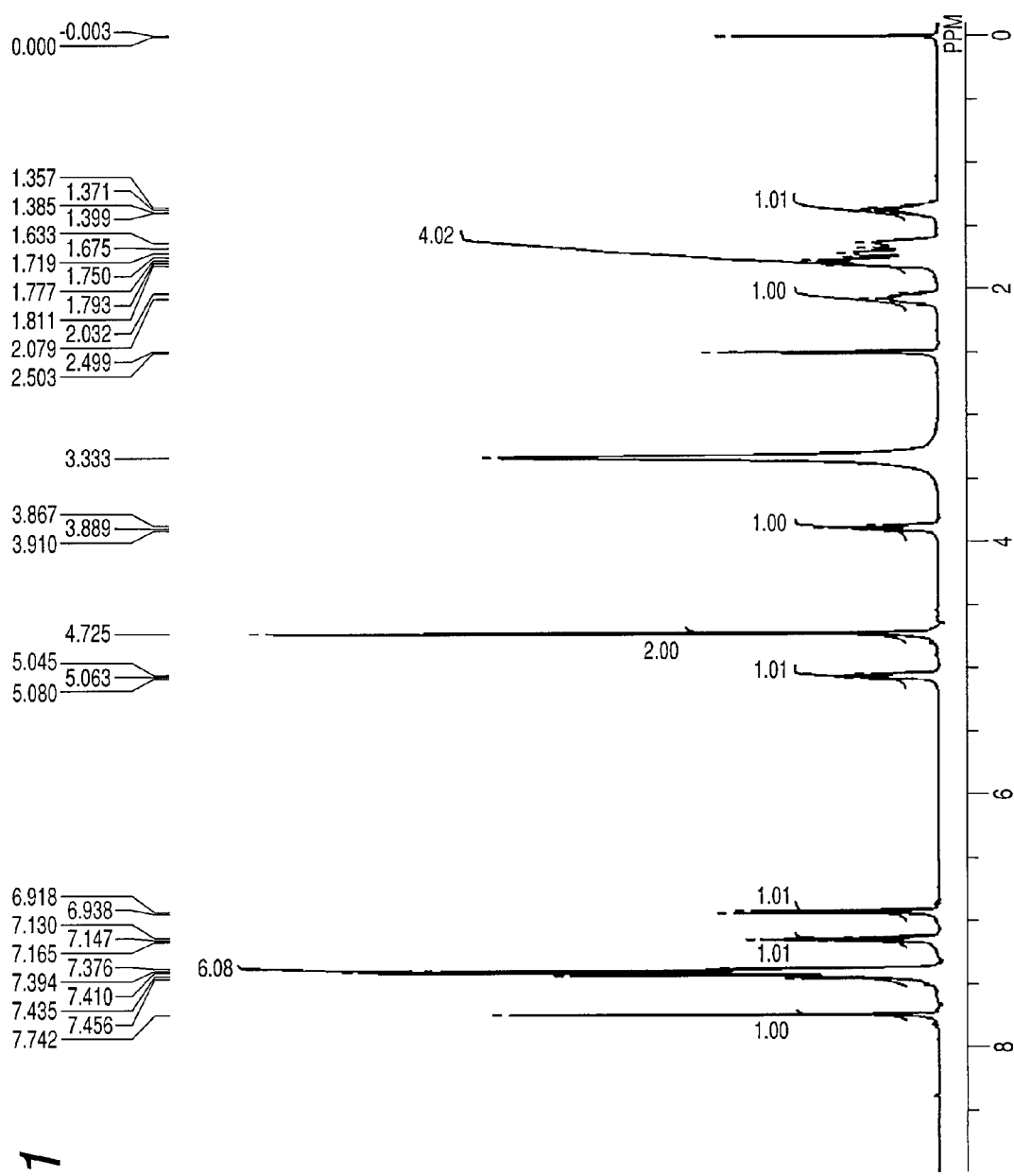
FIG. 1 illustrates a $^1$H-NMR spectrum of a staining compound (1) of the present invention in DMSO-d$_6$ at room temperature at 400 MHz.

Hereinafter, the present invention is described in more detail.

The inventors of the present invention have intensively studied to solve the above-mentioned problems of the prior art. As a result, the inventors have found that the staining compound represented by the following general formula (I) is a novel probe for a biological specimen for labelling a biological specimen with high sensitivity, and enabling more precise diagnosis and drug screening. Thus, the present invention has been completed.

(Chem 2)

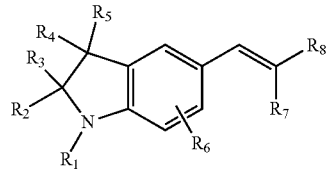

(I)

In the general formula (I): $R_1$ represents one of a hydrogen atom, an alkyl group, an aralkyl group, an alkenyl group, an aryl group, a heterocyclic group, and an acyl group; $R_2$ to $R_5$ each independently represent one of a hydrogen atom, an alkyl group, an aryl group, a carboxylic acid group, a carboxylic acid ester group, and an acyl group, and $R_2$ and $R_4$ may be bonded to each other to form a ring; $R_6$ represents one of a hydrogen atom, an alkyl group, an alkoxy group, and a halogen atom; and $R_7$ and $R_8$ each independently represent one of a hydrogen atom, an alkenyl group, a cyano group, a carboxylic acid group, a carboxylic acid ester group, a sulfonic acid group, an acyl group, and a heterocyclic group, and $R_7$ and $R_8$ may be bonded to each other to form a ring.

The alkyl group represented by $R_1$ in the general formula (I) is not particularly limited and examples thereof include linear, branched, and cyclic alkyl groups having 1 to 20 carbon atoms such as a methyl group, an ethyl group, a propyl group, a butyl group, a pentyl group, a hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a cyclopropyl group, a cyclobutyl group, and a cyclopentyl group.

The aralkyl group represented by $R_1$ is not particularly limited and examples thereof include a benzyl group and a phenetyl group.

The alkenyl group represented by $R_1$ is not particularly limited and examples thereof include alkenyl groups having 2 to 20 carbon atoms such as a vinyl group, a 2,2-diphenylvinyl group, a 3-butenyl group, and a cyclohexenyl group.

The aryl group represented by $R_1$ is not particularly limited and examples thereof include 6- to 14-membered monocyclic and polycyclic aryl groups such as a phenyl group, a naphthyl group, a phenanthryl group, and an anthracenyl group.

The heterocyclic group represented by $R_1$ is not particularly limited and examples thereof include 4- to 10-membered monocyclic and bicyclic heterocyclic groups having 1 to 4 atoms selected from nitrogen, oxygen, and sulfur, such as a pyridyl group, a pyrazinyl group, a pyrimidinyl group, a pyrrolyl group, a thienyl group, a furyl group, a pyranyl group, an oxazolyl group, a thiazolyl group, a triazolyl group, a tetrazolyl group, an imidazolyl group, a pyrazolyl group, a morpholinyl group, a thiomorpholinyl group, a piperidinyl group, a piperazinyl group, a quinolyl group, an isoquinolyl group, an indolyl group, an isoindolyl group, a benzofuryl group, and a benzothienyl group.

The acyl group represented by $R_1$ is not particularly limited and examples thereof include an acetyl group, a propionyl group, a butyryl group, a pentanoyl group, a benzoyl group, a 1-naphthoyl group, and a 2-naphthoyl group.

$R_1$ may further have a substituent and the substituent is not particularly limited as long as the storage stability of the staining compound is not significantly inhibited. Examples thereof include: alkyl groups such as a methyl group, an ethyl group, an n-propyl group, an isopropyl group, an n-butyl group, an isobutyl group, a sec-butyl group, and a tert-butyl group; aryl groups such as a phenyl group and a naphthyl group; alkoxy groups such as a methoxy group, an ethoxy group, and a butoxy group; aryloxy groups such as a phenoxy group and a naphthyloxy group; alkylsulfanyl groups such as a thiomethyl group, a thioethyl group, a thiopropyl group, a thiobutyl group, and a thiophenyl group; monosubstituted amino groups such as a methylamino group and a butylamino group; disubstituted amino groups such as a dimethylamino group, an N-ethyl-N-phenylamino group, and a diphenylamino group; acyl groups such as an acetyl group, a benzoyl group, a carboxylic acid group, a carboxylic acid ester group, and a carbamoyl group; sulfonyl groups such as a sulfonic acid group, a sulfonic acid ester group, and a sulfamoyl group; heterocyclic groups such as a pyridyl group, a triazinyl group, and a benzothiazolyl group; a nitro group; halogen atoms such as a fluorine atom, a chlorine atom, a bromine atom, and an iodine atom; a polyethylene glycol group; and salts such as a quaternary ammonium salt, a carboxylic acid salt, and a sulfonic acid salt. Of those substituents, it is preferred that $R_1$ have a substituent which has property of improving the water solubility and, for example, a carboxylic acid group, a sulfonic acid group, a polyethylene glycol group, a carboxylic acid salt, and a sulfonic acid salt are particularly preferably used, but are not limited thereto. $R_1$ may be independently and arbitrarily selected from the substituents exemplified above, and because the fluorescence intensity is large, preferred examples include an aralkyl group, an alkenyl group, and an aryl group. Specifically, a phenyl group, a bromophenyl group, a benzyl group, a bromobenzyl group, a methylthiophenyl group, a methoxyphenyl group, a methoxynaphthyl group, a benzylphenyl group, a 2,2-diphenylvinyl group, and a 2,2-diphenylvinylphenyl group are preferred. More preferred are a phenyl group, a bromophenyl group, a benzyl group, a methylthiophenyl group, a methoxyphenyl group, and a methoxynaphthyl group. In particular, a methylthiophenyl group is preferred because there is a tendency that a Stokes' shift becomes remarkably large.

The alkyl group represented by each of $R_2$ to $R_5$ in the general formula (I) is not particularly limited and examples thereof include linear, branched, and cyclic alkyl groups having 1 to 20 carbon atoms such as a methyl group, an ethyl group, a propyl group, a butyl group, a pentyl group, a hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a cyclopropyl group, a cyclobutyl group, and a cyclopentyl group.

The aryl group represented by each of $R_2$ to $R_5$ is not particularly limited and examples thereof include 6- to 14-membered monocyclic and polycyclic aryl groups such as a phenyl group, a naphthyl group, a phenanthryl group, and an anthracenyl group.

The carboxylic acid ester group represented by each of $R_2$ to $R_5$ is not particularly limited and examples thereof include a carboxylic acid methyl group, a carboxylic acid ethyl group, a carboxylic acid propyl group, and a carboxylic acid butyl group.

The acyl group represented by each of $R_2$ to $R_5$ is not particularly limited and examples thereof include an acetyl group, a propionyl group, a butyryl group, a pentanoyl group, a benzoyl group, a 1-naphthoyl group, and a 2-naphthoyl group.

Each of $R_2$ to $R_5$ may further have a substituent and the substituent is not particularly limited as long as the storage stability of the staining compound is not significantly inhibited. Examples thereof include: alkyl groups such as a methyl group, an ethyl group, an n-propyl group, an isopropyl group, an n-butyl group, an isobutyl group, a sec-butyl group, and a tert-butyl group; aryl groups such as a phenyl group and a naphthyl group; alkoxy groups such as a methoxy group, an ethoxy group, and a butoxy group; aryloxy groups such as a phenoxy group and a naphthyloxy group; alkylsulfanyl groups such as a thiomethyl group, a thioethyl group, a thiopropyl group, a thiobutyl group, and a thiophenyl group; monosubstituted amino groups such as a methylamino group and a butylamino group; disubstituted amino groups such as a dimethylamino group, an N-ethyl-N-phenylamino group, and a diphenylamino group; acyl groups such as an acetyl group, a benzoyl group, a carboxylic acid group, a carboxylic acid ester group, and a carbamoyl group; sulfonyl groups such as a sulfonic acid group, a sulfonic acid ester group, and a sulfamoyl group; heterocyclic groups such as a pyridyl group, a triazinyl group, and a benzothiazolyl group; a nitro group; halogen atoms such as a fluorine atom, a chlorine atom, a bromine atom, and an iodine atom; a polyethylene glycol group; and salts such as a quaternary ammonium salt, a carboxylic acid salt, and a sulfonic acid salt. Of those substituents, it is preferred that each of $R_2$ to $R_5$ have a substituent which has property of improving the water solubility and, for example, a carboxylic acid group, a sulfonic acid group, a polyethylene glycol group, a carboxylic acid salt, and a sulfonic acid salt are particularly preferably used, but are not limited thereto.

The ring which is formed by $R_2$ and $R_4$ bonded to each other is not particularly limited and examples thereof include: saturated aliphatic rings such as a cyclooctane ring, a cycloheptane ring, a cyclohexane ring, a cyclopentane ring, and a cyclobutane ring; and partially saturated aliphatic rings such as a cyclopentene ring and a cyclohexene ring. Further, the ring may have a substituent and the substituent is not particularly limited as long as the storage stability of the staining compound is not significantly inhibited. Examples thereof include alkyl groups such as a methyl group, an ethyl group, an n-propyl group, an isopropyl group, an n-butyl group, an isobutyl group, a sec-butyl group, and a tert-butyl group; aryl groups such as a phenyl group and a naphthyl group; alkoxy groups such as a methoxy group, an ethoxy group, and a butoxy group; aryloxy groups such as a phenoxy group and a naphthyloxy group; alkylsulfanyl groups such as a thiomethyl group, a thioethyl group, a thiopropyl group, a thiobutyl group, and a thiophenyl group; monosubstituted amino groups such as a methylamino group and a butylamino group; disubstituted amino groups such as a dimethylamino group, an N-ethyl-N-phenylamino group, and a diphenylamino group; acyl groups such as an acetyl group, a benzoyl group, a carboxylic acid group, a carboxylic acid ester group, and a carbamoyl group; sulfonyl groups such as a sulfonic acid group, a sulfonic acid ester group, and a sulfamoyl group; heterocyclic groups such as a pyridyl group, a triazinyl group, and a benzothiazolyl group; a nitro group; halogen atoms such as a fluorine atom, a chlorine atom, a bromine atom, and an iodine atom; a polyethylene glycol group; and salts such as a quaternary ammonium salt, a carboxylic acid salt, and a sulfonic acid salt. Of those substituents, it is preferred that the ring have a substituent which has property of improving the water solubility and, for example, a carboxylic acid group, a sulfonic acid group, a polyethylene glycol group, a carboxylic acid salt, and a sulfonic acid salt are particularly preferably used, but are not limited thereto.

It is preferred that $R_2$ to $R_5$ each independently represent one of a hydrogen atom, an alkyl group, and an aryl group, and $R_2$ and $R_4$ be bonded to each other to form a ring. It is more preferred that $R_2$ and $R_4$ be bonded to each other to form a ring, because which is a stable chemical structure. Specific examples thereof include a cyclooctane ring, a cycloheptane ring, a cyclohexane ring, a cyclopentane ring, and a cyclobutane ring. In terms of storage stability, a cyclopentane ring is more preferred.

The alkyl group represented by $R_6$ in the general formula (I) is not particularly limited and examples thereof include linear, branched, and cyclic alkyl groups having 1 to 20 carbon atoms such as a methyl group, an ethyl group, a propyl group, a butyl group, a pentyl group, a hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a cyclopropyl group, a cyclobutyl group, and a cyclopentyl group.

The alkoxy group represented by $R_6$ in the general formula (I) is not particularly limited and examples thereof include alkoxy groups having 1 to 20 carbon atoms such as a methoxy group, an ethoxy group, a propoxy group, a butoxy group, a pentyloxy group, a decyloxy group, a hexyloxy group, a heptyloxy group, an octyloxy group, a nonyloxy group, a dodecyloxy group, and an octadecyloxy group. Examples of the halogen atom represented by $R_6$ include a fluorine atom, a chlorine atom, a bromine atom, and an iodine atom.

$R_6$ preferably represents one of a hydrogen atom, a halogen atom, and an alkoxy group, and more preferably represents one of a hydrogen atom and a halogen atom.

The alkenyl group represented by each of $R_7$ and $R_8$ in the general formula (I) is not particularly limited and examples thereof include a 2-cyanoacrylic acid group, a ethylidene malononitrile group, a 2-ethylidene malonic acid dimethyl ester group, a 2-ethylidene malonic acid diethyl ester group, a 2-ethylidene malonic acid butyl ester group, a 5-ethylidene-4-oxo-2-thioxothiazolidinyl-3-acetic acid, 5-ethylidene-4-oxo-2-thioxothiazolidinyl-3-propanoic acid, 3-ethyl-5-ethylidene-2-thioxothiazolidin-4-one, and 5-ethylidene-4-oxo-2-(3-ethyl-4-oxo-2-thioxothiazolidene)-thiazolidinyl-3-acetic acid.

The carboxylic acid ester group represented by each of $R_7$ and $R_8$ is not particularly limited and examples thereof include a carboxylic acid methyl group, a carboxylic acid ethyl group, a carboxylic acid propyl group, and a carboxylic acid butyl group.

The acyl group represented by each of $R_7$ and $R_8$ is not particularly limited and examples thereof include an acetyl group, a propionyl group, a butyryl group, a pentanoyl group, a benzoyl group, a 1-naphthoyl group, and a 2-naphthoyl group.

The heterocyclic group represented by each of $R_7$ and $R_8$ is not particularly limited and examples thereof include 4- to 10-membered monocyclic and bicyclic heterocyclic groups having 1 to 4 atoms selected from nitrogen, oxygen, and sulfur, such as a pyridyl group, a pyrazinyl group, a pyrimidinyl group, a pyrrolyl group, a thienyl group, a furyl group, a pyranyl group, an oxazolyl group, a thiazolyl group, a triazolyl group, a tetrazolyl group, an imidazolyl group, a pyrazolyl group, a morpholinyl group, a thiomorpholinyl group, a piperidinyl group, a piperazinyl group, a quinolyl group, an isoquinolyl group, an indolyl group, an isoindolyl group, a benzofuryl group, and a benzothienyl group.

Further, the ring may have a substituent and the substituent is not particularly limited as long as the storage stability of the staining compound is not significantly inhibited. Examples thereof include: alkyl groups such as a methyl group, an ethyl group, an n-propyl group, an isopropyl group, an n-butyl group, an isobutyl group, a sec-butyl group, and a tert-butyl group; aryl groups such as a phenyl group and a naphthyl group; alkoxy groups such as a methoxy group, an ethoxy group, and a butoxy group; aryloxy groups such as a phenoxy group and a naphthyloxy group; alkylsulfanyl groups such as a thiomethyl group, a thioethyl group, a thiopropyl group, a thiobutyl group, and a thiophenyl group; monosubstituted amino groups such as a methylamino group and a butylamino group; disubstituted amino groups such as a dimethylamino group, an N-ethyl-N-phenylamino group, and a diphenylamino group; acyl groups such as an acetyl group, a benzoyl group, a carboxylic acid group, a carboxylic acid ester group, and a carbamoyl group; sulfonyl groups such as a sulfonic acid group, a sulfonic acid ester group, and a sulfamoyl group; heterocyclic groups such as a pyridyl group, a triazinyl group, and a benzothiazolyl group; a nitro group; halogen atoms such as a fluorine atom, a chlorine atom, a bromine atom, and an iodine atom; a polyethylene glycol group; and salts such as a quaternary ammonium salt, a carboxylic acid salt, and a sulfonic acid salt. Of those substituents, it is preferred that the ring have a substituent which has property of improving the water solubility and, for example, a carboxylic acid group, a sulfonic acid group, a polyethylene glycol group, a carboxylic acid salt, and a sulfonic acid salt are particularly preferably used, but are not limited thereto.

For $R_7$ and $R_8$, any one of $R_7$ and $R_8$ preferably represents, in terms of ease of synthesis of the compound, one of a cyano group, a carboxylic acid group, and a heterocyclic group, and any one of $R_7$ and $R_8$ particularly preferably represents a cyano group. Further, when any one of $R_7$ and $R_8$ represents a hydrogen atom, the other preferably represents one of a heterocyclic group represented by the following general formula (II) and an alkenyl group.

(Chem 3)

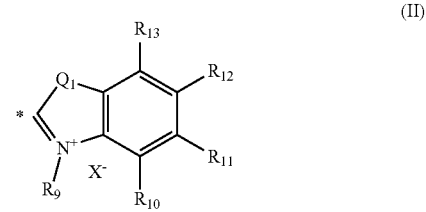

(II)

In the general formula (II): $R_9$ represents one of an alkyl group and an aryl group; $R_{10}$ to $R_{13}$ each independently represent one of a hydrogen atom, an alkyl group, an aryl group, an alkoxy group, a carboxylic acid group, a sulfonic acid group, a heterocyclic group, an amino group, and a halogen atom; one of $R_{10}$ and $R_{11}$, $R_{11}$ and $R_{12}$, and $R_{12}$ and $R_{13}$ may be bonded to each other to form a ring; $X^-$ represents an anionic group; $Q_1$ represents one of a sulfur atom, an oxygen atom, $-C(R_{14})(R_{15})-$, $-CH=CH-$, and $-N(R_{16})-$; $R_{14}$ to $R_{16}$ each independently represent one of a hydrogen atom, an alkyl group, and an aryl group.

The alkyl group represented by $R_9$ in the general formula (II) is not particularly limited and examples thereof include linear, branched, and cyclic alkyl groups having 1 to 20 carbon atoms such as a methyl group, an ethyl group, a propyl group, a butyl group, a pentyl group, a hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a cyclopropyl group, a cyclobutyl group, and a cyclopentyl group.

The aryl group represented by $R_9$ is not particularly limited and examples thereof include 6- to 14-membered monocyclic and polycyclic aryl groups such as a phenyl group, a naphthyl group, a phenanthryl group, and an anthracenyl group.

$R_9$ may further have a substituent and the substituent is not particularly limited as long as the storage stability of the staining compound is not significantly inhibited. Examples thereof include: alkyl groups such as a methyl group, an ethyl group, an n-propyl group, an isopropyl group, an n-butyl group, an isobutyl group, a sec-butyl group, and a tert-butyl group; aryl groups such as a phenyl group and a naphthyl group; alkoxy groups such as a methoxy group, an ethoxy group, and a butoxy group; aryloxy groups such as a phenoxy group and a naphthyloxy group; alkylsulfanyl groups such as a thiomethyl group, a thioethyl group, a thiopropyl group, a thiobutyl group, and a thiophenyl group; monosubstituted amino groups such as a methylamino group and a butylamino group; disubstituted amino groups such as a dimethylamino group, an N-ethyl-N-phenylamino group, and a diphenylamino group; acyl groups such as an acetyl group, a benzoyl group, a carboxylic acid group, a carboxylic acid ester group, and a carbamoyl group; sulfonyl groups such as a sulfonic acid group, a sulfonic acid ester group, and a sulfamoyl group; heterocyclic groups such as a pyridyl group, a triazinyl group, and a benzothiazolyl group; a nitro group; halogen atoms such as a fluorine atom, a chlorine atom, a bromine atom, and an iodine atom; a polyethylene glycol group; and salts such as a quaternary ammonium salt, a carboxylic acid salt, and a sulfonic acid salt. Of those substituents, it is preferred that $R_9$ have a substituent which has property of improving the water solubility and, for example, a carboxylic acid group, a sulfonic acid group, a polyethylene glycol group, a carboxylic acid salt, and a sulfonic acid salt are particularly preferably used, but are not limited thereto. $R_9$ preferably represents an alkyl group. In addition, the alkyl group preferably has a substituent such as a carboxylic acid group, a sulfonic acid group, a polyethylene glycol group, and salts thereof because the water solubility of the compound is increased and the fluorescence intensity of the compound is also increased.

The alkyl group represented by each of $R_{10}$ to $R_{13}$ in the general formula (II) is not particularly limited and examples thereof include linear, branched, and cyclic alkyl groups having 1 to 20 carbon atoms such as a methyl group, an ethyl group, a propyl group, a butyl group, a pentyl group, a hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a cyclopropyl group, a cyclobutyl group, and a cyclopentyl group.

The aryl group represented by each of $R_{10}$ to $R_{13}$ is not particularly limited and examples thereof include 6- to 14-membered monocyclic and polycyclic aryl groups such as a phenyl group, a naphthyl group, a phenanthryl group, and an anthracenyl group.

The alkoxy group represented by each of $R_{10}$ to $R_{13}$ is not particularly limited and examples thereof include alkoxy groups having 1 to 20 carbon atoms such as a methoxy group, an ethoxy group, a propoxy group, a butoxy group, a pentyloxy group, a decyloxy group, a hexyloxy group, a heptyloxy group, an octyloxy group, a nonyloxy group, a dodecyloxy group, and an octadecyloxy group.

The heterocyclic group represented by each of $R_{10}$ to $R_{13}$ is not particularly limited and examples thereof include 4- to 10-membered monocyclic and bicyclic heterocyclic groups having 1 to 4 atoms selected from nitrogen, oxygen, and sulfur, such as a pyridyl group, a pyrazinyl group, a pyrimidinyl group, a pyrrolyl group, a thienyl group, a furyl group, a pyranyl group, an oxazolyl group, a thiazolyl group, a triazolyl group, a tetrazolyl group, an imidazolyl group, a pyrazolyl group, a morpholinyl group, a thiomorpholinyl group, a piperidinyl group, a piperazinyl group, a quinolyl group, an isoquinolyl group, an indolyl group, an isoindolyl group, a benzofuryl group, and a benzothienyl group.

The amino group represented by each of $R_{10}$ to $R_{13}$ is not particularly limited and examples thereof include: an unsubstituted amino group; monosubstituted amino groups such as an N-methylamino group, an N-butylamino group, an N-hexylamino group, an N-tetradecylamino group, an N-phenylamino group, and an N-naphthylamino group; disubstituted amino groups such as an N,N-dimethylamino group, an N,N-diethylamino group, an N,N-diphenylamino group, and an N,N-methylpropylamino group; carbonylamino groups such as an acetylamino group, an ethylcarbonylamino group, a tert-butylcarbonylamino group, a benzoylamino group, a naphthoylamino group, and a methoxycarbonylamino group; and sulfonylamino groups such as a methylsulfonylamino group, an ethylsulfonylamino group, a tert-butylsulfonylamino group, and an iso-propoxysulfonylamino group.

Examples of the halogen atom represented by each of $R_{10}$ to $R_{13}$ include a fluorine atom, a chlorine atom, a bromine atom, and an iodine atom.

$R_{10}$ to $R_{13}$ each preferably represent one of a hydrogen atom, a carboxylic acid group, a sulfonic acid group, an amino group, and a halogen atom, and more preferably represent a hydrogen atom and a sulfonic acid group, each of which improves the water solubility of the compound. Further, salts such like a carboxylic acid and a sulfonic acid also preferably fall within the scope of the present invention.

The ring which is formed by one of $R_{10}$ and $R_{11}$, $R_{11}$ and $R_{12}$, and $R_{12}$ and $R_{13}$ bonded to each other is not particularly limited and examples thereof include: aromatic rings having 3 to 10 carbon atoms such as a benzene ring and a naphthalene ring; saturated rings such as a cyclooctane ring, a cycloheptane ring, a cyclohexane ring, a cyclopentane ring, and a cyclobutane ring; partially saturated rings such as a cyclopentene ring and a cyclohexene ring; and heterocycles such as a pyridine ring and a pyrimidine ring. Further, the ring may have a substituent and the substituent is not particularly limited as long as the storage stability of the staining compound is not significantly inhibited. Examples thereof include: alkyl groups such as a methyl group, an ethyl group, an n-propyl group, an isopropyl group, an n-butyl group, an isobutyl group, a sec-butyl group, and a tert-butyl group; aryl groups such as a phenyl group and a naphthyl group; alkoxy groups such as a methoxy group, an ethoxy group, and a butoxy group; aryloxy groups such as a phenoxy group and a naphthyloxy group; alkylsulfanyl groups such as a thiomethyl group, a thioethyl group, a thiopropyl group, a thiobutyl group, and a thiophenyl group; monosubstituted amino groups such as a methylamino group and a butylamino group; disubstituted amino groups such as a dimethylamino group, an N-ethyl-N-phenylamino group, and a diphenylamino group; acyl groups such as an acetyl group, a benzoyl group, a carboxylic acid group, a carboxylic acid ester group, and a carbamoyl group; sulfonyl groups such as a sulfonic acid group, a sulfonic acid ester group, and a sulfamoyl group; heterocyclic groups such as a pyridyl group, a triazinyl group, and a benzothiazolyl group; a nitro group; halogen atoms such as a fluorine atom, a chlorine atom, a bromine atom, and an iodine atom; a polyethylene glycol group; and salts such as a quaternary ammonium salt, a carboxylic acid salt, and a sulfonic acid salt. Of those substituents, it is preferred that the ring have a substituent which has property of improving the water solubility and, for example, a carboxylic acid group, a sulfonic acid group, a polyethylene glycol group, a carboxylic acid salt, and a sulfonic acid salt are particularly preferably used, but are not limited thereto. The ring which is formed by one of $R_{10}$ and $R_{11}$, $R_{11}$ and $R_{12}$, and $R_{12}$ and $R_{13}$ bonded to each other is preferably a benzene ring, because the storage stability of the compound is improved.

$X^-$ in the general formula (II) represents an anionic group. Here, the anionic group is not particularly limited and examples thereof include: halogen ions such as a fluoride ion, a chloride ion, a bromide ion, and an iodide ion; inorganic acid ions such as a sulfuric acid ion, a phosphoric acid ion, a nitric acid ion, a tetrafluoroboric acid ion, and a hexafluorophosphoric acid ion; Lewis acid-containing ions such as a tetrachloroaluminum ion; and organic acid ions such as an acetic acid ion, a lactic acid ion, a methanesulfonic acid ion, a benzenesulfonic acid ion, a p-toluenesulfonic acid ion, a trifluoroacetic acid ion, a trifluoromethanesulfonic acid ion, and a tetraphenylboric acid ion.

Preferred examples of the anionic group represented by $X^-$ include a chloride ion, a bromide ion, an iodide ion, a sulfuric acid ion, a nitric acid ion, and a methanesulfonic acid ion, and more preferred examples include, in terms of ease of synthesis of the compound, a bromide ion and an iodide ion.

$Q_1$ in the general formula (II) represents one of a sulfur atom, an oxygen atom, —$C(R_{14})(R_{15})$—, —CH=CH—, and —$N(R_{16})$—.

The alkyl group represented by each of $R_{14}$ to $R_{16}$ in $Q_1$ is not particularly limited and examples thereof include linear, branched, and cyclic alkyl groups having 1 to 20 carbon atoms such as a methyl group, an ethyl group, a propyl group, a butyl group, a pentyl group, a hexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a cyclopropyl group, a cyclobutyl group, and a cyclopentyl group.

The aryl group represented by each of $R_4$ to $R_{16}$ in $Q_1$ is not particularly limited and examples thereof include 6- to 14-membered monocyclic and polycyclic aryl groups such as a phenyl group, a naphthyl group, a phenanthryl group, and an anthracenyl group.

One of a benzoxazolyl ring group where $Q_1$ represents an oxygen atom, a benzothiazolyl ring group where $Q_1$ represents a sulfur atom, and a dimethylindolenyl ring group where $Q_1$ represents —$C(CH_3)(CH_3)$— is particularly preferred because the storage stability of the compound is satisfactory.

In the general formula (I), the ring formed by $R_7$ and $R_8$ bonded to each other is not particularly limited and examples thereof include a partially saturated ring and a heterocycle each formed of one of 5- and 6-membered rings.

When the ring formed by $R_7$ and $R_8$ bonded to each other is an aliphatic ring formed of one of 5- and 6-membered rings, the aliphatic ring is not particularly limited and examples thereof include a 2,3-dihydroindene ring, an indene-1,3-dione ring, a 4-cyclopentene-1,3-dione ring, a fluorene ring, a cyclohexanone ring, and a 5,5-dimethyl-1-cyclohexene ring.

When the ring formed by $R_7$ and $R_8$ bonded to each other is a heterocycle formed of one of 5- and 6-membered rings, the heterocycle is not particularly limited and a particularly preferred example thereof includes a heterocycle formed of a 5-membered ring represented by one of the following general formulae (III) and (IV).

(Chem 4)

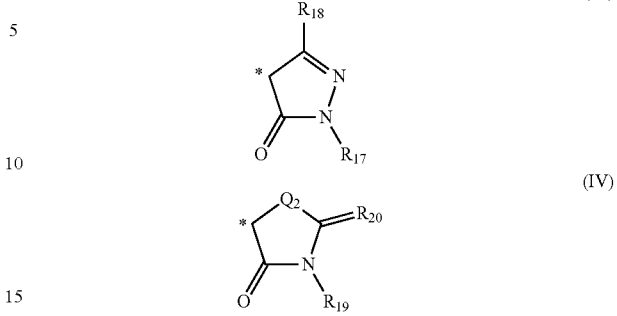

In the general formula (III): $R_{17}$ represents one of a hydrogen atom, an alkyl group, an aryl group, and a heterocyclic group; and $R_{18}$ represents one of an alkyl group, an aryl group, a carboxylic acid group, a carboxylic acid ester group, a hydroxyl group, and an amino group. In the general formula (IV): $Q_2$ represents one of an oxygen atom, a sulfur atom, and —$N(R_{21})$—; $R_{19}$ represents one of a hydrogen atom, an alkyl group, an aryl group, and a heterocyclic group; $R_{20}$ represents one of a sulfur atom, an oxygen atom, =$NR_{22}$, a heterocycle, a methylene group replaced by a heterocycle, and a dicyanomethylene group; $R_{21}$ and $R_{22}$ each represent one of a hydrogen atom, an alkyl group, an aryl group, and a heterocyclic group.

The alkyl group represented by each of $R_{17}$ and $R_{18}$ in the general formula (III) is not particularly limited and 1.5 examples thereof include linear, branched, and cyclic alkyl groups having 1 to 20 carbon atoms such as a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a cyclopropyl group, a cyclobutyl group, and a cyclopentyl group.

The aryl group represented by each of $R_{17}$ and $R_{18}$ is not particularly limited and examples thereof include 6- to 14-membered monocyclic and polycyclic aryl groups such as a phenyl group, a naphthyl group, a phenanthryl group, and an anthracenyl group. The ring may further have a substituent and the substituent is not particularly limited as long as the storage stability of the staining compound is not significantly inhibited. Examples thereof include: alkyl groups such as a methyl group, an ethyl group, an n-propyl group, an isopropyl group, an n-butyl group, an isobutyl group, a sec-butyl group, and a tert-butyl group; aryl groups such as a phenyl group and a naphthyl group; alkoxy groups such as a methoxy group, an ethoxy group, and a butoxy group; aryloxy groups such as a phenoxy group and a naphthyloxy group; alkylsulfanyl groups such as a thiomethyl group, a thioethyl group, a thiopropyl group, a thiobutyl group, and a thiophenyl group; monosubstituted amino groups such as a methylamino group and a butylamino group; disubstituted amino groups such as a dimethylamino group, an N-ethyl-N-phenylamino group, and a diphenylamino group; acyl groups such as an acetyl group, a benzoyl group, a carboxylic acid group, a carboxylic acid ester group, and a carbamoyl group; sulfonyl groups such as a sulfonic acid group, a sulfonic acid ester group, and a sulfamoyl group; heterocyclic groups such as a pyridyl group, a triazinyl group, and a benzothiazolyl group; a nitro group; halogen atoms such as a fluorine atom, a chlorine atom, a bromine atom, and an iodine atom; a polyethylene glycol group; and salts such as a quaternary ammonium salt, a carboxylic acid salt, and a sulfonic acid salt. Of those substituents, it is preferred that the aryl group have a substituent which has property of improving the water solubility and, for example, a carboxylic acid group, a sulfonic acid group, a polyethylene glycol group, a carboxylic acid salt, and a sulfonic acid salt are particularly preferably used, but are not limited thereto.

The heterocyclic group represented by $R_{17}$ is not particularly limited and examples thereof include 4- to 10-membered monocyclic and bicyclic heterocyclic groups having 1 to 4 atoms selected from nitrogen, oxygen, and sulfur, such as a pyridyl group, a pyrazinyl group, a pyrimidinyl group, a pyrrolyl group, a thienyl group, a furyl group, a pyranyl group, an oxazolyl group, a thiazolyl group, a triazolyl group, a tetrazolyl group, an imidazolyl group, a pyrazolyl group, a morpholinyl group, a thiomorpholinyl group, a piperidinyl group, a piperazinyl group, a quinolyl group, an isoquinolyl group, an indolyl group, an isoindolyl group, a benzofuryl group, and a benzothienyl group.

$R_{17}$ in the general formula (III) preferably represents an aryl group in terms of stability of the compound. In addition, the aryl group preferably has a substituent such as a carboxylic acid group, a sulfonic acid group, a polyethylene glycol group, a carboxylic acid salt, and sulfonic acid salt because the water solubility is improved.

The carboxylic acid ester group represented by $R_{18}$ is not particularly limited and examples thereof include a carboxylic acid methyl ester group, a carboxylic acid ethyl ester group, a carboxylic acid propyl ester group, and a carboxylic acid butyl ester group.

The amino group represented by $R_{18}$ is not particularly limited and examples thereof include: an unsubstituted amino group; monosubstituted amino groups such as an N-methylamino group, an N-butylamino group, an N-hexylamino group, an N-tetradecylamino group, an N-phenylamino group, and an N-naphthylamino group; disubstituted amino groups such as an N,N-dimethylamino group, an N,N-diethylamino group, an N,N-diphenylamino group, and an N,N-methylpropylamino group; carbonylamino groups such as an acetylamino group, an ethylcarbonylamino group, a tert-butylcarbonylamino group, a benzoylamino group, a naphthoylamino group, and a methoxycarbonylamino group; and sulfonylamino groups such as a methylsulfonylamino group, an ethylsulfonylamino group, a tert-butylsulfonylamino group, and an iso-propoxysulfonylamino group.

$R_{18}$ in the general formula (III) preferably represents, in terms of ease of synthesis of the compound, one of an alkyl group, an aryl group, a carboxylic acid group, and an amino group, and particularly preferably represents one of an alkyl group and a carboxylic acid group.

$Q_2$ in the general formula (IV) represents one of an oxygen atom, a sulfur atom, and —N($R_{21}$)—.

The alkyl group represented by each of $R_{19}$, $R_{21}$, and $R_{22}$ in the general formula (IV) and $Q_2$ is not particularly limited and examples thereof include linear, branched, and cyclic alkyl groups having 1 to 20 carbon atoms such as a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, a cyclopropyl group, a cyclobutyl group, and a cyclopentyl group. The alkyl group may further have a substituent and the substituent is not particularly limited as long as the storage stability of the staining compound is not significantly inhibited. Examples thereof include: alkyl groups such as a methyl group, an ethyl group, an n-propyl group, an isopropyl group, an n-butyl group, an isobutyl group, a sec-butyl group, and a tert-butyl group; aryl groups such as a phenyl group and a naphthyl group; alkoxy groups such as a methoxy group, an ethoxy group, and a butoxy group; aryloxy groups such as a phenoxy group and a naphthyloxy group; alkylsulfanyl groups such as a thiomethyl group, a thioethyl group, a thiopropyl group, a thiobutyl group, and a thiophenyl group; monosubstituted amino groups such as a methylamino group and a butylamino group; disubstituted amino groups such as a dimethylamino group, an N-ethyl-N-phenylamino group, and a diphenylamino group; acyl groups such as an acetyl group, a benzoyl group, a carboxylic acid group, a carboxylic acid ester group, and a carbamoyl group; sulfonyl groups such as a sulfonic acid group, a sulfonic acid ester group, and a sulfamoyl group; heterocyclic groups such as a pyridyl group, a triazinyl group, and a benzothiazolyl group; a nitro group; halogen atoms such as a fluorine atom, a chlorine atom, a bromine atom, and an iodine atom; a polyethylene glycol group; and salts such as a quaternary ammonium salt, a carboxylic acid salt, and a sulfonic acid salt. Of those substituents, it is preferred that the alkyl group have a substituent which has property of improving the water solubility and, for example, a carboxylic acid group, a sulfonic acid group, a polyethylene glycol group, a carboxylic acid salt, and a sulfonic acid salt are particularly preferably used, but are not limited thereto.

The aryl group represented by each of $R_{19}$, $R_{21}$, and $R_{22}$ in the general formula (IV) and $Q_2$ is not particularly limited and examples thereof include 6- to 14-membered monocyclic and polycyclic aryl groups such as a phenyl group, a naphthyl group, a phenanthryl group, and an anthracenyl group.

The heterocyclic group represented by each of $R_{19}$ to $R_{22}$ in the general formula (IV) and $Q_2$ is not particularly limited and examples thereof include 4- to 10-membered monocyclic and bicyclic heterocyclic groups having 1 to 4 atoms selected from nitrogen, oxygen, and sulfur, such as a pyridyl group, a pyrazinyl group, a pyrimidinyl group, a pyrrolyl group, a thienyl group, a furyl group, a pyranyl group, an oxazolyl group, a thiazolyl group, a triazolyl group, a tetrazolyl group, an imidazolyl group, a pyrazolyl group, a morpholinyl group, a thiomorpholinyl group, a piperidinyl group, a piperazinyl group, a quinolyl group, an isoquinolyl group, an indolyl group, an isoindolyl group, a benzofuryl group, 2-thioxothiazolidin-4-one group, and a benzothienyl group.

$R_{19}$ in the general formula (IV) preferably represents an alkyl group. In addition, the alkyl group preferably has a substituent such as a carboxylic acid group, a sulfonic acid group, a polyethylene glycol group, a carboxylic acid salt, and a sulfonic acid salt because the water solubility of the compound is increased and the fluorescence intensity is also increased.

$R_{20}$ in the general formula (IV) preferably represents one of a sulfur atom, an oxygen atom, a heterocycle, and a methylene group replaced by a heterocycle. In the case where $R_{20}$ represents a sulfur atom, the staining property tends to be improved. Also, in the case where $R_{20}$ represents a heterocycle such as 2-thioxothiazolidin-4-one having a substituent at the 3-position, the maximum fluorescence emission wavelength is often shifted to a long-wavelength side and detected in a near-infrared wavelength area, which allows the application in a near-infrared area. Accordingly, the above-mentioned cases are more preferred.

The compound represented by the general formula (I) preferably contains at least one of a carboxylic acid group, a sulfonic acid group, and a polyethylene glycol group because the water solubility is improved. Salts of a carboxylic acid and a sulfonic acid also fall within the scope of the present invention. Specific examples thereof include: but not particularly limited to; alkaline metal salts such as a sodium salt and a potassium salt; alkaline earth salts such as a magnesium salt and a calcium salt; amine salts such as an ammonium salt, a pyridinium salt, a piperidinium salt, and a triethylammonium salt; and amino acid salts such as a tryptophan salt, a lysine salt, a leucine salt, a phenylalanine salt, a valine salt, and an arginine salt. Preferred examples include a sodium salt, a potassium salt, an ammonium salt, a pyridinium salt, and a piperidinium salt.

The staining compound according to the present invention can be utilized for labelling of a biological specimen as a staining agent that is retained in a specific site in the biological specimen by itself, and stains the specific site retaining the compound in the biological specimen based on the coloring property of the structure of the compound itself. Further, the staining compound according to the present invention can be used as a probe such that a compound capable of transmitting an optical signal is further added to the staining compound, by utilizing a feature of being retained in a specific site in a biological specimen. The compound to be added may be bonded directly or via a linker molecule. For the compound to be added, such a low molecular weight compound that can penetrate a biological membrane such as a cell membrane and permeate into a biological specimen is preferably used.

Next, a production method for a staining compound having a structure represented by the general formula (I) of the present invention is described below.

The staining compound represented by general formula (I) according to the present invention can be easily synthesized by a known method (for example, Chem. Comm., Vol. 24, pp. 3036-3037, 2003). Hereinafter, an exemplary synthesis scheme is described.

That is, the coupling of an aldehyde derivative (A) and a compound (B) yields one of staining compounds (I) and (I'). For example, a method described below is given as a specific coupling method. One of the compounds (I) and (I') may be isolated before use, and may be used in mixture. Further, functional groups of the aldehyde derivative (A), the compound (B), and the staining compound represented by the general formula (I) may be additionally subjected to reactions such as known protection and deprotection reactions, and hydrolysis, as necessary. This can be appropriately selected by those skilled in the art.

(Chem 5)

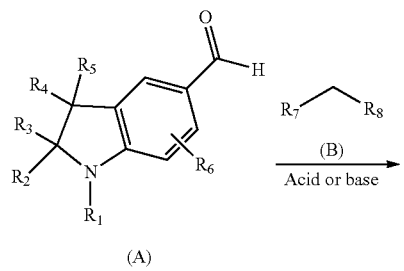

(A)

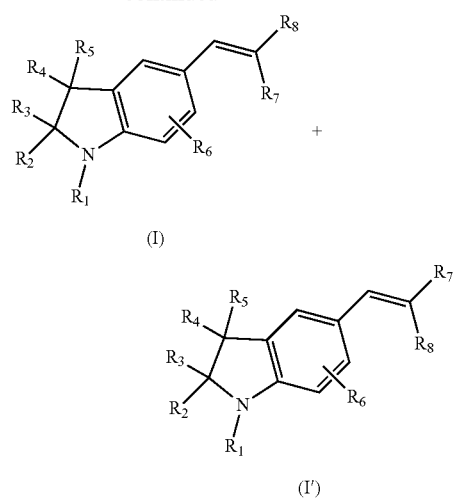

The aldehyde derivative (A) to be used in the present invention is commercially available and can also be synthesized by a known method (for example, J. Am. Chem. Soc., Vol. 126, pp. 12325-12335, 2004, Tetrahedron Letters, Vol. 38, No. 50, pp. 8721-8722, 1997, J. Med. Chem., 50, pp. 4405-4418, 2007, and Hetetocycles, Vol. 60, No. 12, pp. 2761-2765, 2003).

Preferred specific examples of the aldehyde derivative (A) to be used in the present invention are described, but are not limited to the following examples.

(Chem 6-1)

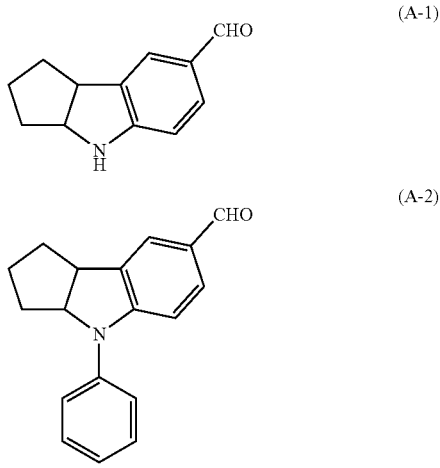

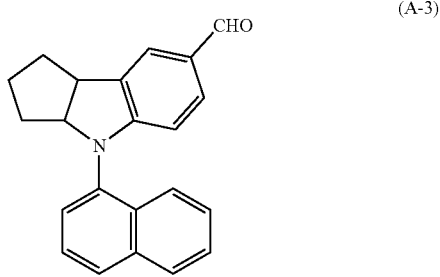

(A-4) 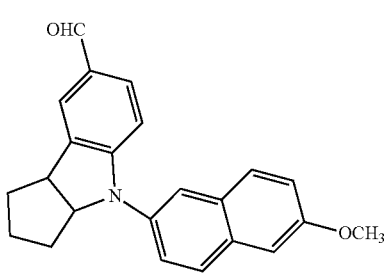
(A-5) 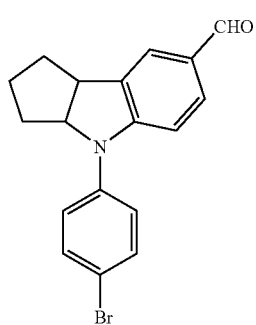
(A-6) 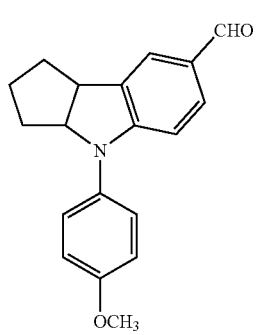
(A-7) 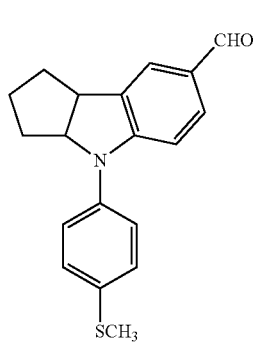
(A-8) 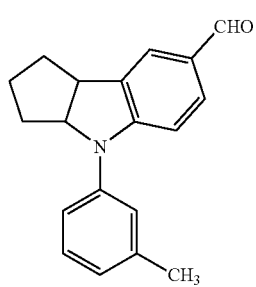
(A-9) 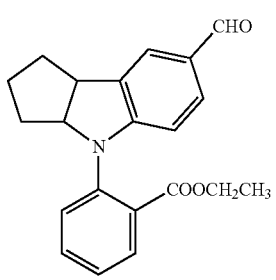
(A-10) 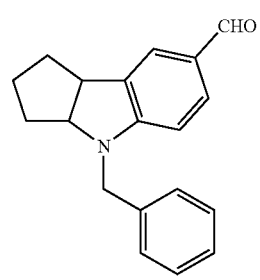
(A-11) 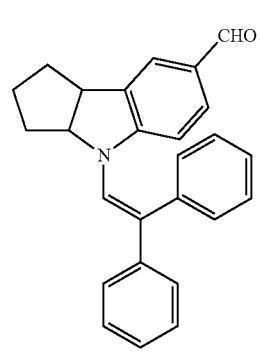
(A-12) 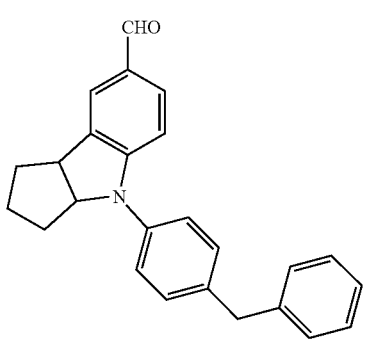
A-13) 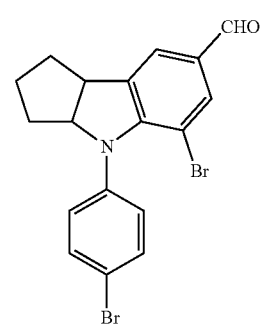

-continued
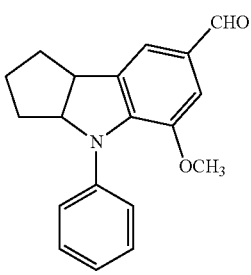 (A-14)
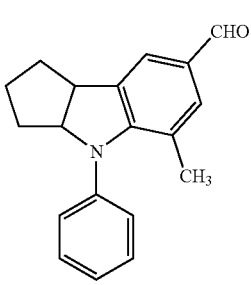 (A-15)
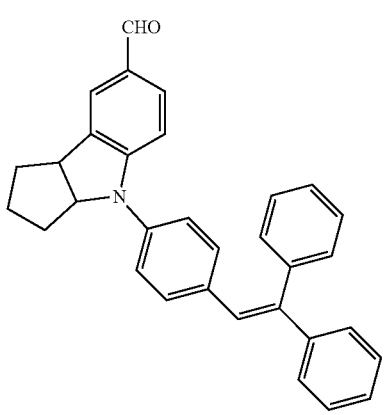 (A-16)
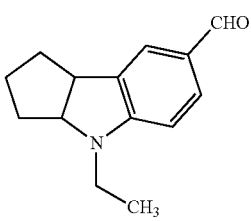 (A-17)
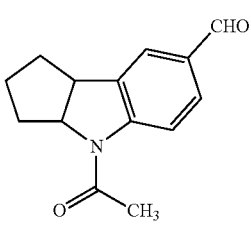 (A-18)
(Chem 6-2)
-continued
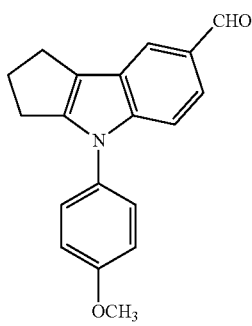 (A-19)
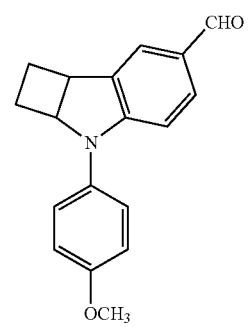 (A-20)
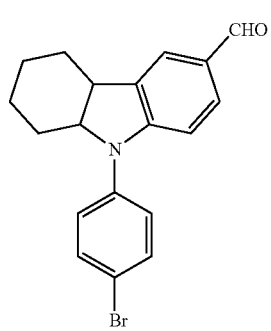 (A-21)
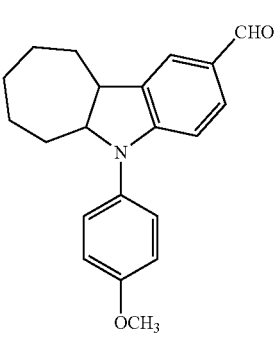 (A-22)
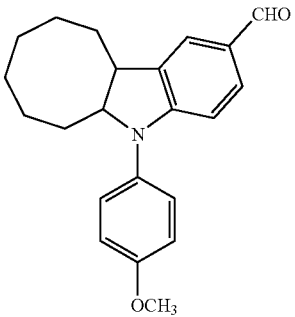 (A-23)

(A-24)
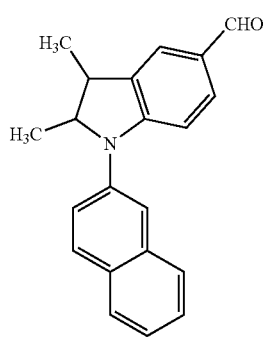
(A-25)
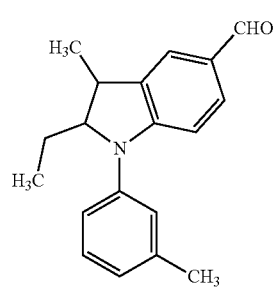
(A-26)
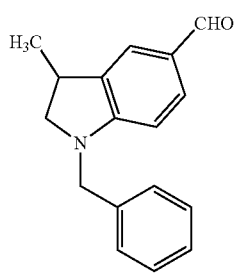
(A-27)
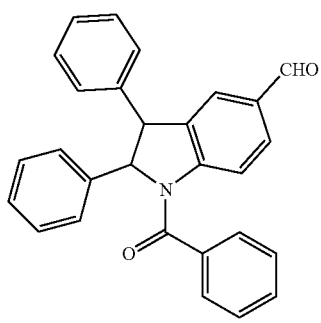
(A-28)
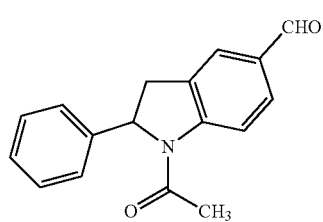
(A-28)
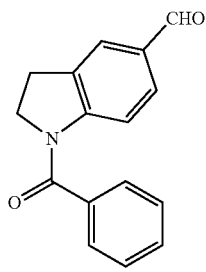
(A-29)
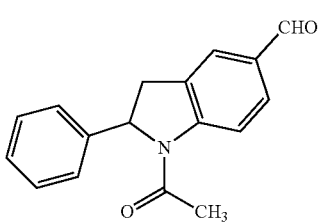
(A-30)
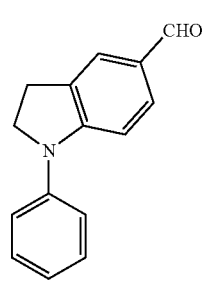
(A-31)
(A-32)

-continued
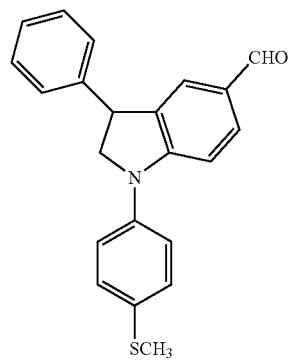
(A-33)
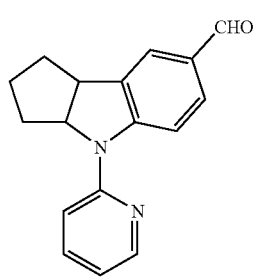
(A-34)
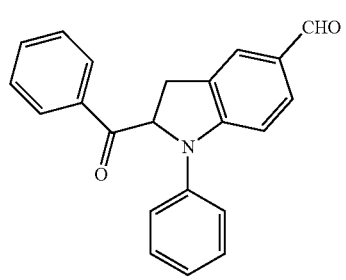
(A-35)
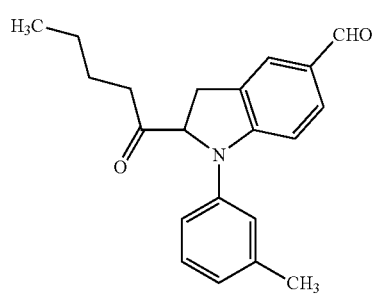
(A-36)
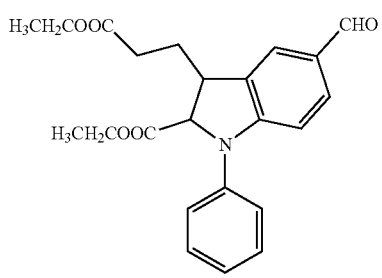
(A-37)
-continued
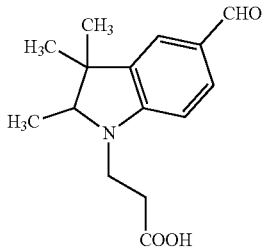
(A-38)
(Chem 6-3)
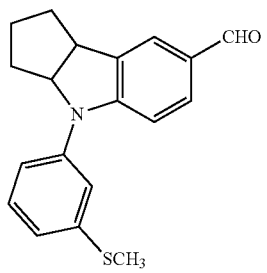
(A-39)
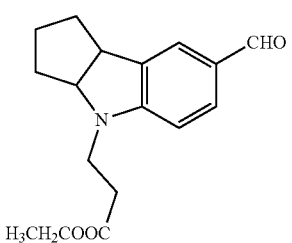
(A-40)
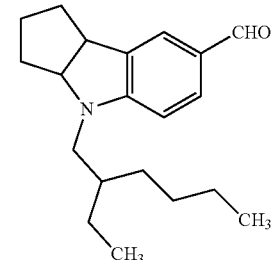
(A-41)
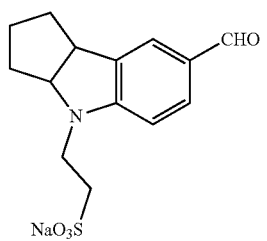
(A-42)
Preferred specific examples of the compound (B) to be used in present invention are described, but are not-limited to the following examples.
(Chem 7-1)
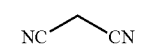
(B-1)
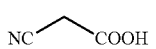
(B-2)

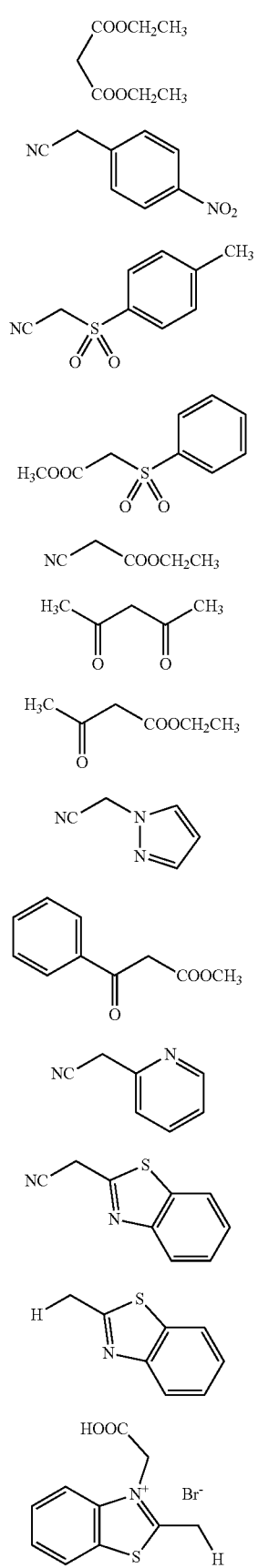
(B-3)
(B-4)
(B-5)
(B-6)
(B-7)
(B-8)
(B-9)
(B-10)
(B-11)
(B-12)
(B-13)
(B-14)
(B-15)
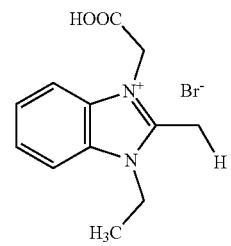
(B-16)
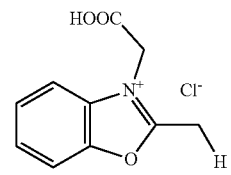
(B-17)
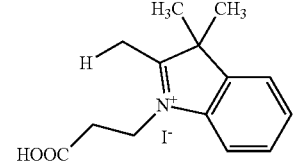
(B-18)
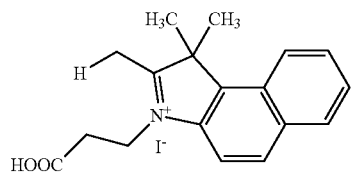
(B-19)
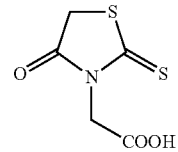
(B-20)
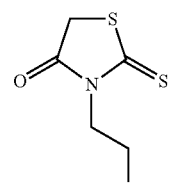
(B-21)
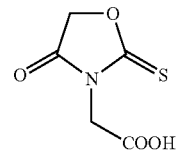
(B-22)
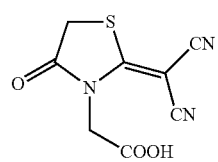
(B-23)

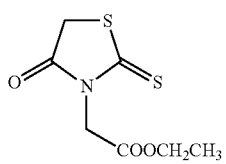 (B-24)
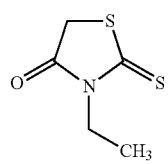 (B-25)
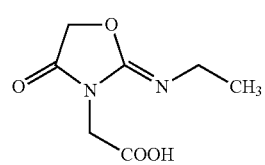 (B-26)
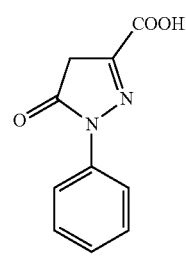 (B-27)
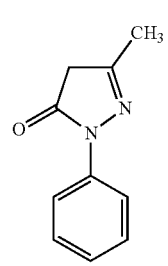 (B-28)
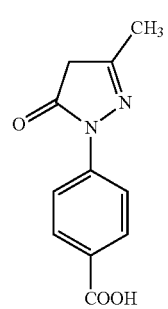 (B-29)
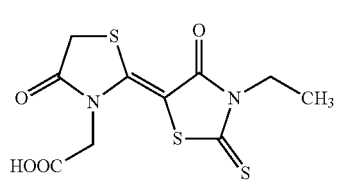 (B-30)
(Chem 7-2)
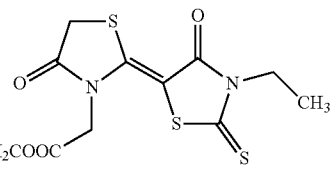 (B-31)
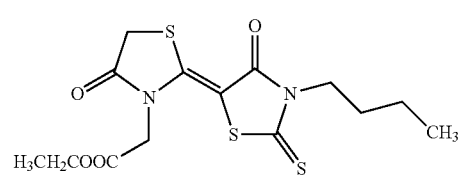 (B-32)
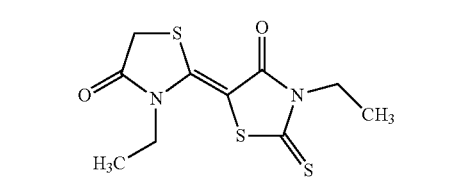 (B-33)
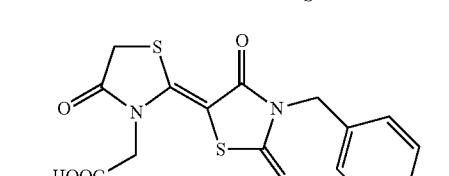 (B-34)
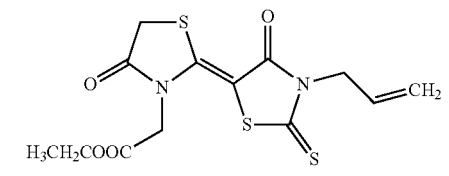 (B-35)
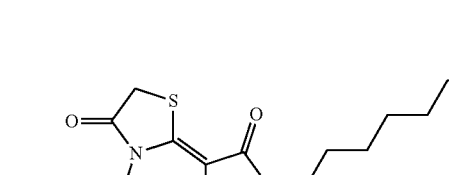 (B-36)
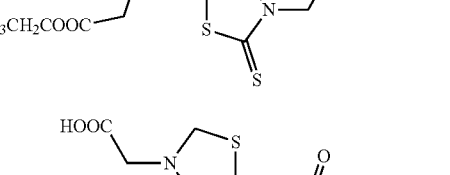 (B-37)
(B-47)
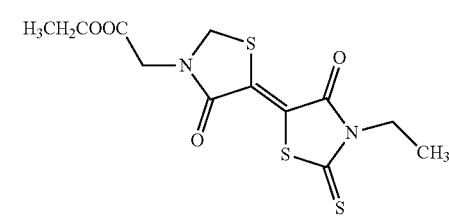 (B-38)

-continued (B-39)
(B-40)
(B-41)
(B-42)
(B-43)
(B-44)
(B-45)
(B-46)

-continued (B-47)
(B-48)
(B-49)
(B-50)
(B-51)
(B-52)

(B-53) 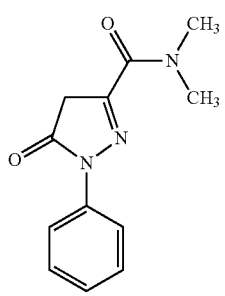
(B-54) 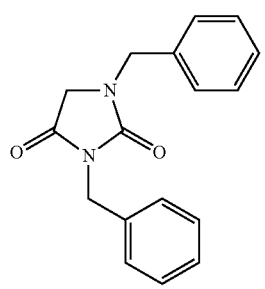
(B-55) 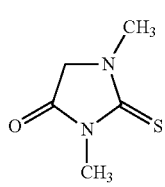
(B-56) 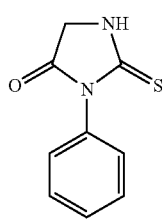
(B-57) 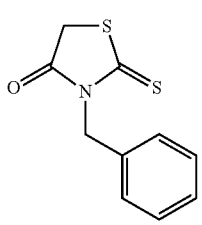
(B-58) 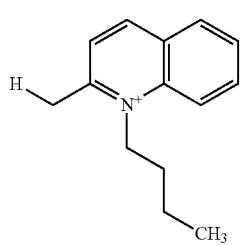
(B-59) 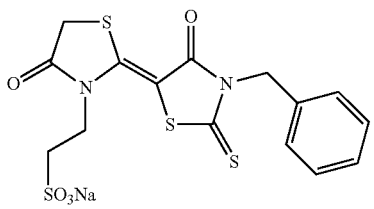
(Chem 7-3)
(B-60) 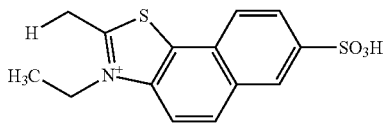
(B-61) 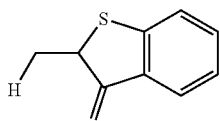
(B-62) 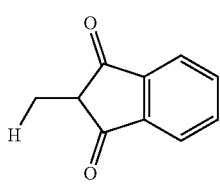
(B-63) 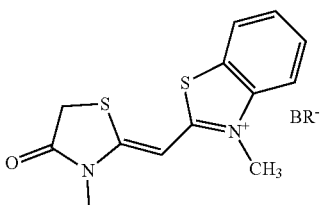
(B-64) 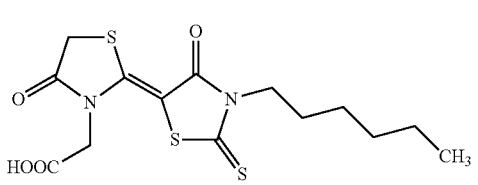
(B-65) 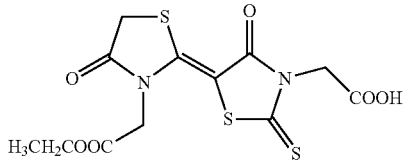
(B-66) 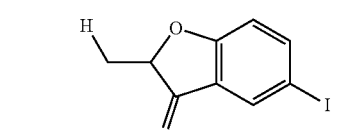
(B-67) 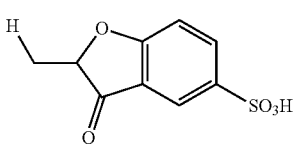

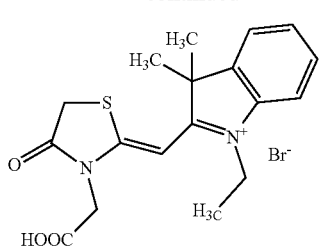
(B-68)

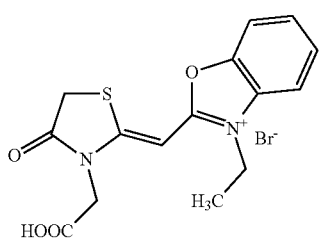
(B-69)

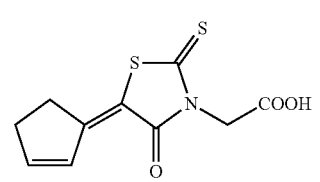
(B-70)

The amount of the compound (B) to be used is 0.1 to 10-fold mol, preferably 0.5 to 3-fold mol, and more preferably 0.8 to 2-fold mol with respect to 1 mol of the aldehyde derivative (A).

This step may also be performed without using any solvent but is preferably performed in the presence of a solvent. The solvent is not particularly limited as long as it is not involved in the reaction, and examples thereof include: an ester-based solvent such as methyl acetate, ethyl acetate, isopropyl acetate, and butyl acetate; a nitrile-based solvent such as acetonitrile, propionitrile, and benzonitrile; an aromatic solvent such as benzene, toluene, xylene, ethylbenzene, chlorobenzene, and mesitylene; an ether-based solvent such as diisopropyl ether, methyl tert-butyl ether, and tetrahydrofuran; an alcohol-based solvent such as methanol, ethanol, n-propyl alcohol, iso-propyl alcohol, butyl alcohol, and diethylene glycol; a ketone-based solvent such as acetone and methyl ethyl ketone; N,N-dimethylformamide (hereinafter abbreviated as DMF); N,N-dimethylsulfoxide (hereinafter abbreviated as DMSO); water; and acetic acid. Preferred examples include an alcohol-based solvent such as methanol, ethanol, n-propyl alcohol, iso-propyl alcohol, butyl alcohol, and diethylene glycol, water, and acetic acid, and more preferred examples include ethanol, iso-propyl alcohol, diethylene glycol, and acetic acid. Further, two or more kinds of solvents may be used in mixture, and the mixing ratio may be arbitrarily set during use in mixture. The amount of a reaction solvent to be used in this step is in the range of 0.1 to 1,000-fold weight, preferably 0.5 to 500-fold weight, and more preferably 1.0 to 150-fold weight with respect to the aldehyde derivative (A).

The reaction temperature at which this step is performed is in the range of −80° C. to 250° C., preferably −20° C. to 200° C., and more preferably −5° C. to 150° C. In general, the reaction is completed within 24 hours.

In this step, the reaction rapidly proceeds by the addition of an acid or a base as necessary. The acid to be used is not limited as long as it is not involved in the reaction, and examples thereof include: an inorganic acid such as hydrochloric acid, sulfuric acid, and phosphoric acid; an organic acid such as p-toluenesulfonic acid, formic acid, acetic acid, propionic acid, and trifluoroacetic acid; a strongly acidic ion-exchange resin such as Amberlite (Rohm and Haas Company) and Amberlyst (Rohm and Haas Company); and an inorganic acid salt such as ammonium formate and ammonium acetate. More preferred is an inorganic acid salt such as ammonium formate and ammonium acetate, and still more preferred is ammonium acetate. The amount of the acid to be used is 0.001 to 50-fold mol, preferably 0.01 to 10-fold mol, and more preferably 0.1 to 5-fold mol with respect to 1 mol of the aldehyde derivative (A).

Specific examples of the base to be used in this step include: a metal alkoxide such as potassium tert-butoxide, sodium tert-butoxide, sodium methoxide, and sodium ethoxide; an organic base such as piperidine, pyridine, 2-methylpyridine, dimethylaminopyridine, diethylamine, triethylamine, isopropylethylamine, sodium acetate, potassium acetate, 1,8-diazabicyclo[5.4.0]undeca-7-ene (hereinafter abbreviated as DBU), and ammonium acetate; an organic base such as n-butyl lithium and tert-magnesium chloride; and an inorganic base such as sodium borohydride, metallic sodium, sodium hydride, and sodium carbonate. Preferred examples include potassium tert-butoxide, sodium methoxide, sodium ethoxide, piperidine, dimethylaminopyridine, sodium acetate, and ammonium acetate, and more preferred examples include sodium methoxide, piperidine, sodium acetate, and ammonium acetate. The amount of the above-mentioned base to be used is 0.1 to 20-fold mol, preferably 0.5 to 8-fold mol, and more preferably 1.0 to 4-fold mol with respect to 1 mol of the aldehyde derivative (A).

After the completion of the reaction, the dilution with water, the acid deposition with hydrochloric acid or the like may be performed to obtain a staining compound (I).

The obtained staining compound (I) may be subjected to a conventional method for isolation and purification of an organic compound. For example, after acid deposition has been performed by acidifying a reaction solution with hydrochloric acid or the like, a solid is separated by filtration, followed by neutralization with sodium hydroxide and the like and concentration. Thus, a crude product is obtained. In addition, the crude product is purified by, for example, recrystallization from acetone, methanol, and the like, and silica gel column chromatography. The purification may be performed by using one of those methods alone or by using two or more kinds thereof in combination to afford a product with high purity. The staining compound represented by the general formula (I) can be synthesized by the above-mentioned production method. Hereinafter, specific examples of the staining compound of the present invention are described in items (1) to (142). However, the staining compound is not limited to the following examples. Further, the staining compound of the present invention may have cis and trans structural isomers, and those structural isomers also fall within the scope of the present invention. It should be noted that specific examples of the staining compound of represented by the general formula (II) are described in items (23), (24), (27), (31), (32), (34), (35), (45), (46), (72) to (79), (90), (91), (111), (124), and (126). Further, specific examples of the staining compound represented by the general formula (III) are described in items (14), (15), (21), (22), (26), (42) to (44), (47), (48), (50) to (54), and (128). Still further, specific examples of the staining compound represented by the general formula (IV) are described in items (1) to (4), (9) to (12), (16) to (20), (28) to (30), (37), (38), (40), (55), (58) to (63), (66) to (71), (80) to (89), (92), (94), (95), (97) to (104), (109), (110), (114) to (118), (122), (123), (125), (127), (129), (130), (132), (133), and (136) to (139).
(Chem 8-1)
(1)
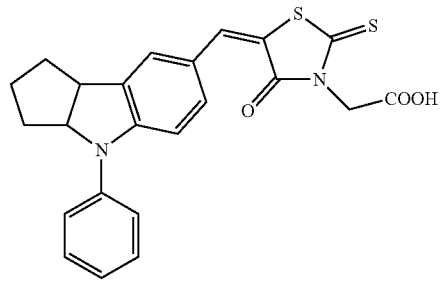
(2)
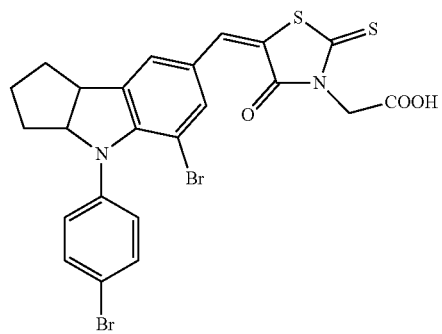
(3)
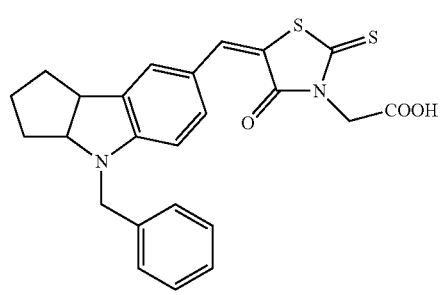
(4)
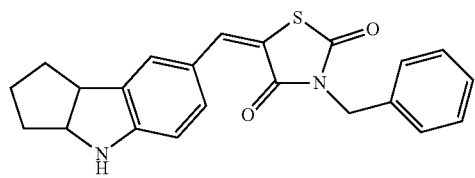
(5)
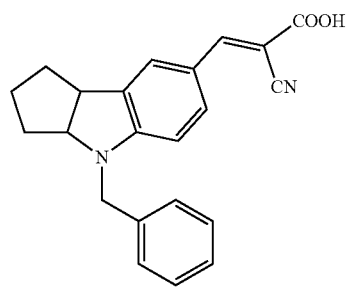
-continued
(6)
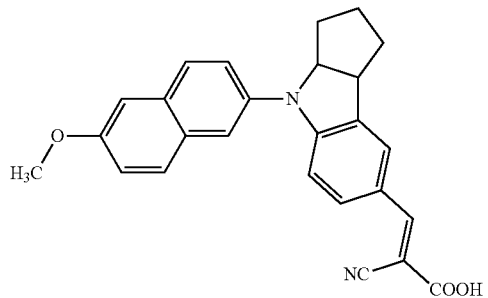
(7)
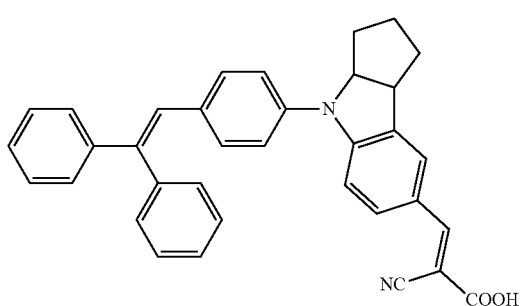
(8)
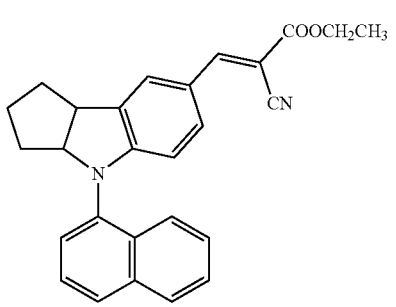
(9)
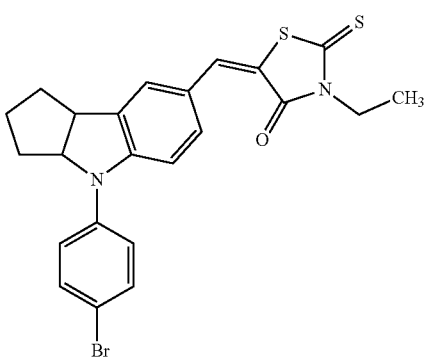
(10)
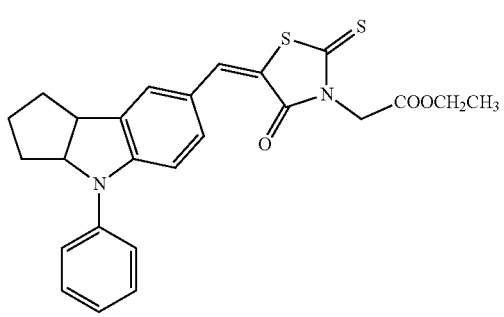

-continued
(11)
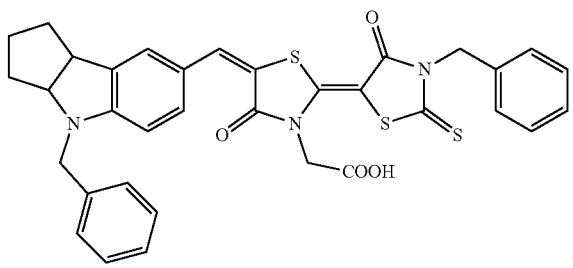
(12)
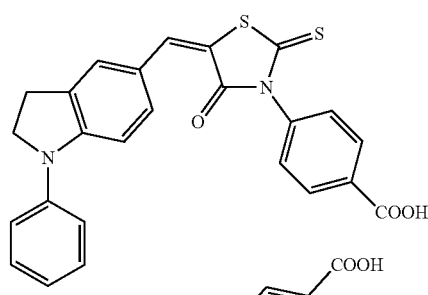
(13)
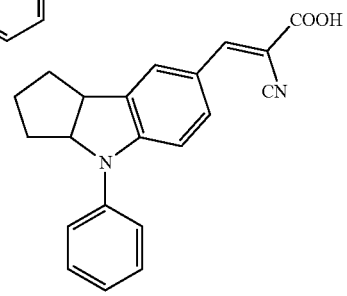
(14)
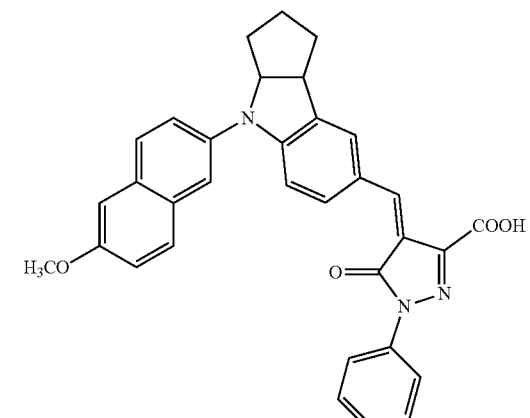
(15)
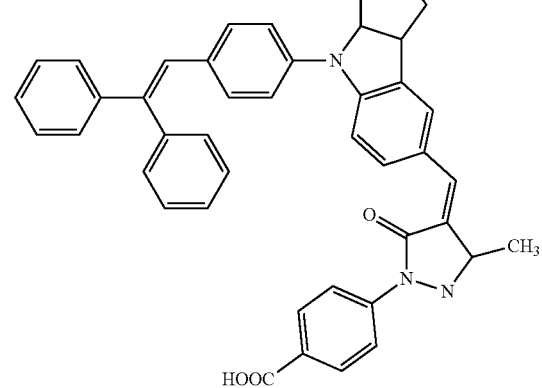
-continued
(16)
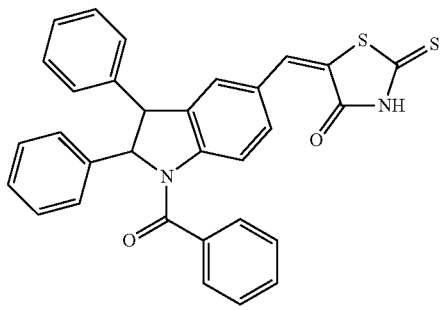
(17)
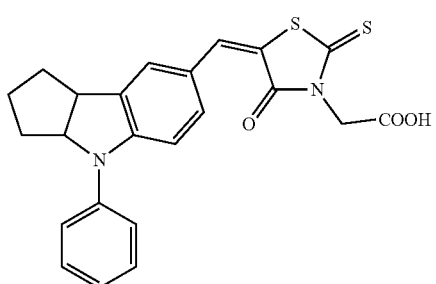
(18)
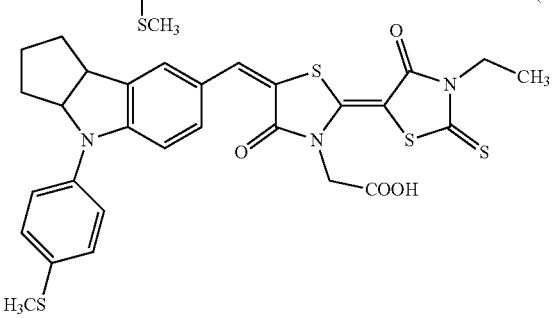
(19)
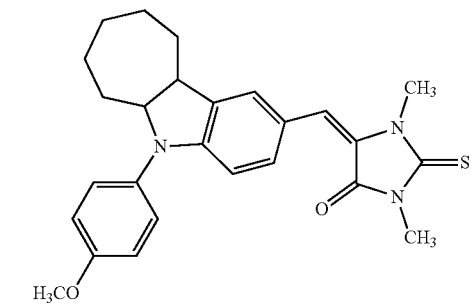
(20)
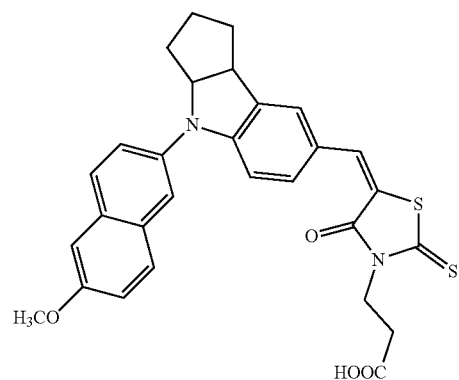

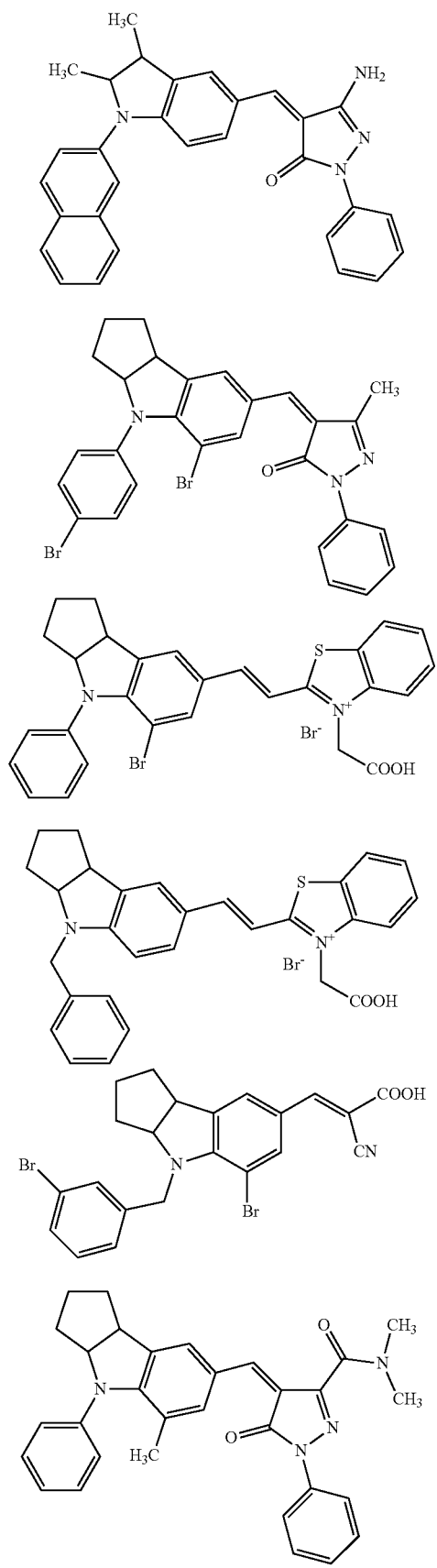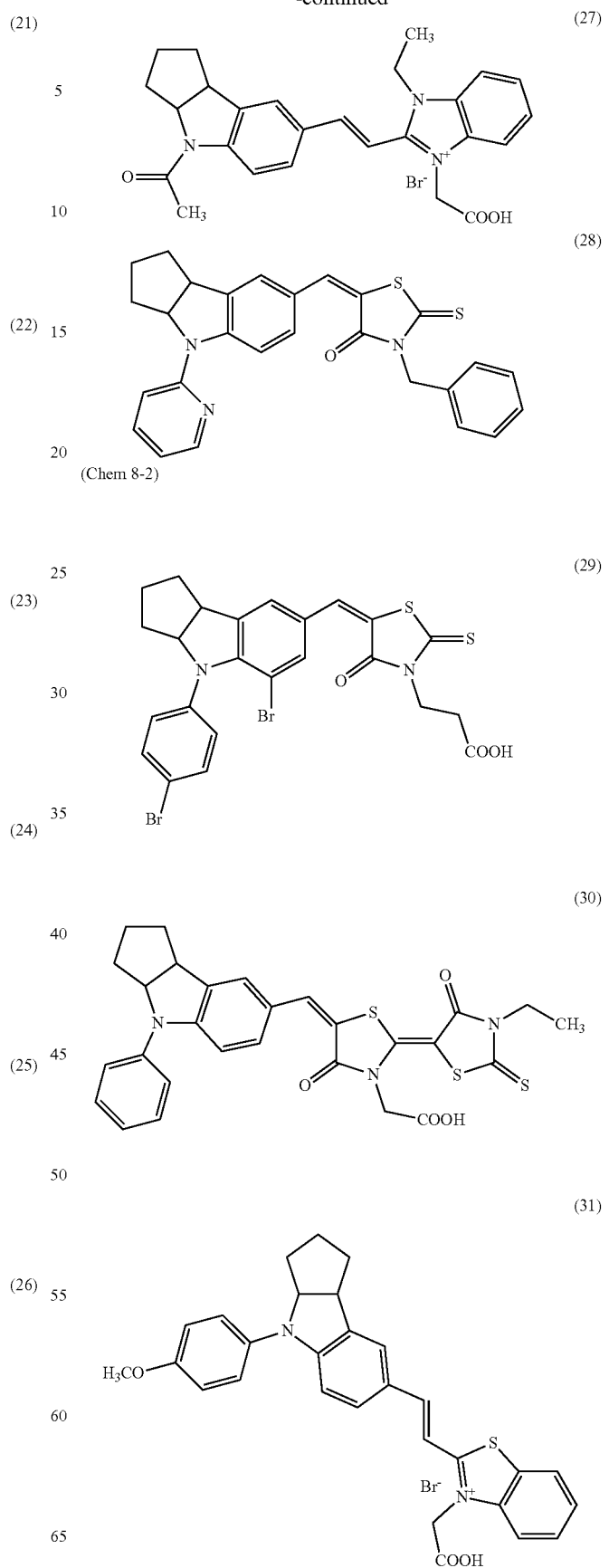

-continued
(32)
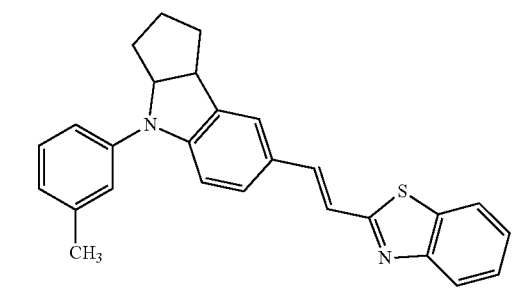
(33)
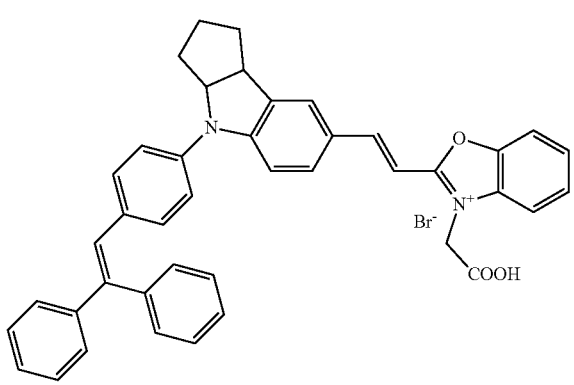
(34)
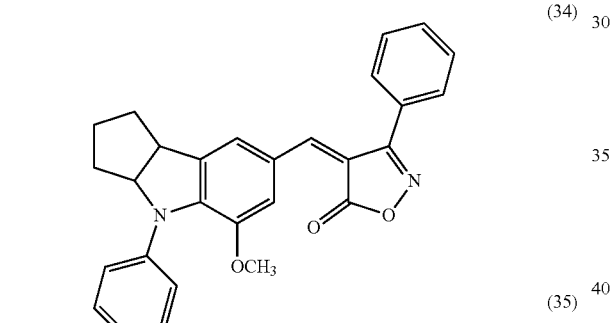
(35)
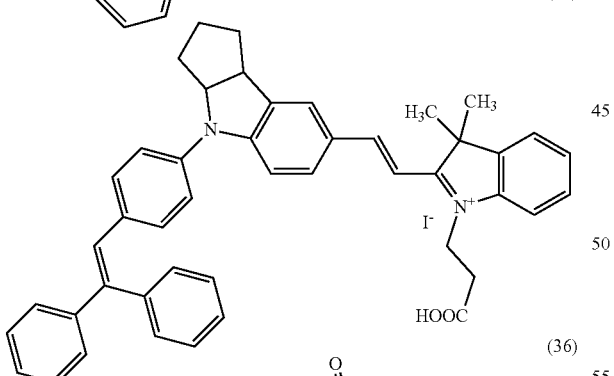
(36)
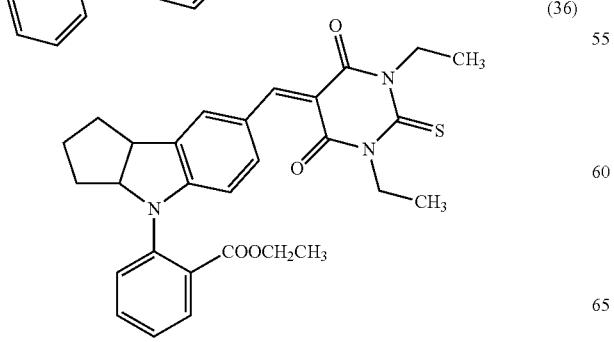
-continued
(37)
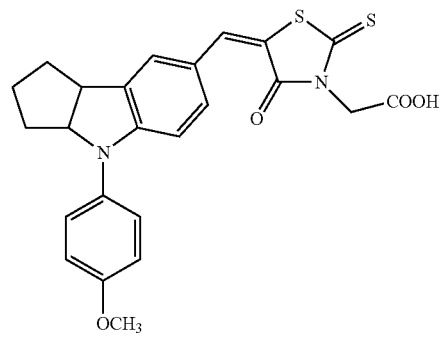
(38)
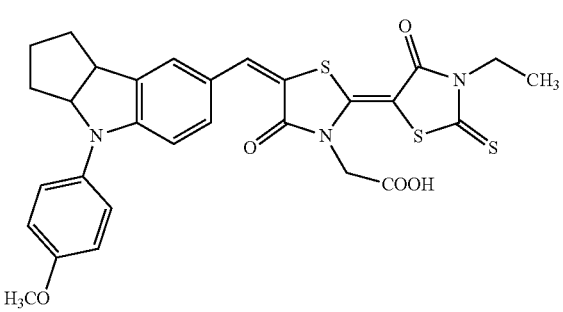
(39)
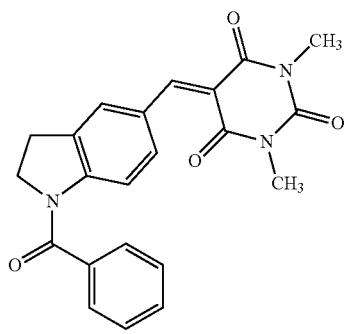
(40)
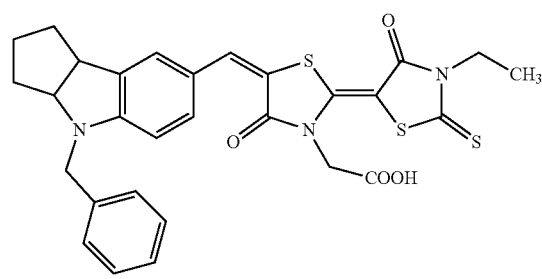
(41)
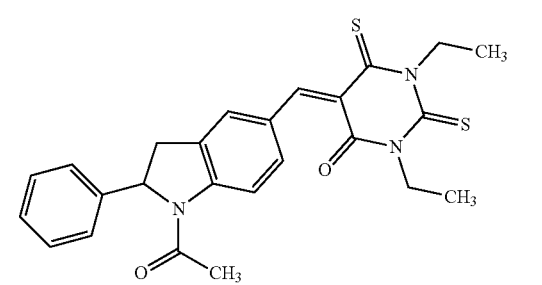

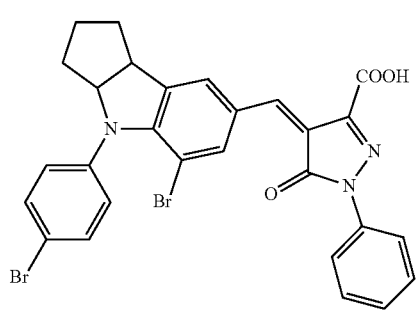

(51)
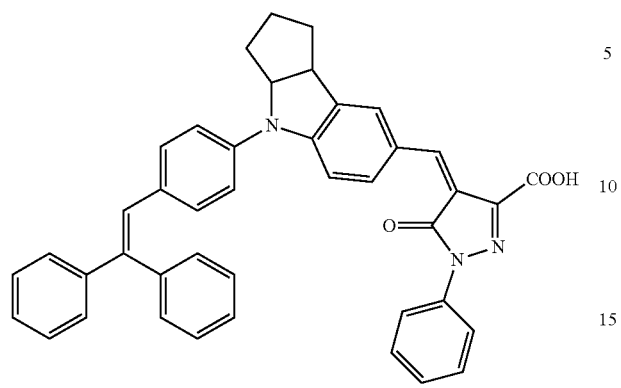
(52)
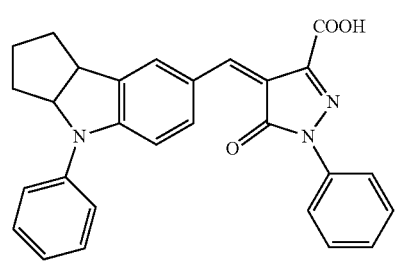
(53)
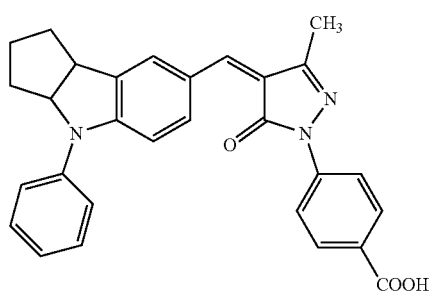
(54)
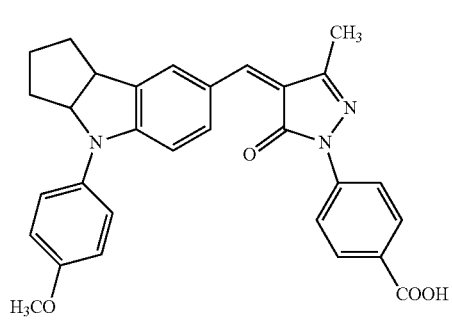
(55)
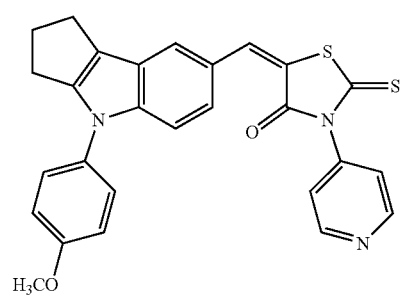
(56)
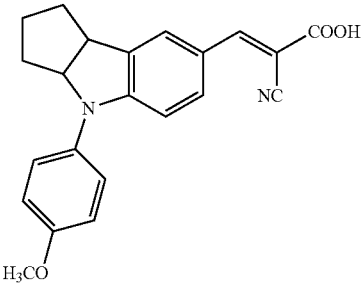
(Chem 8-3)
(57)
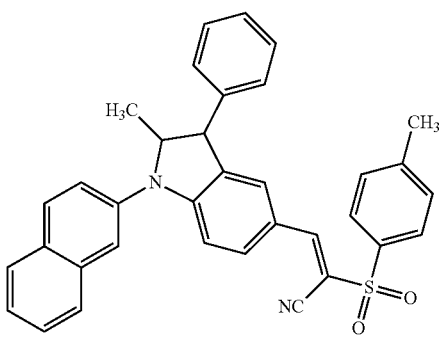
(58)
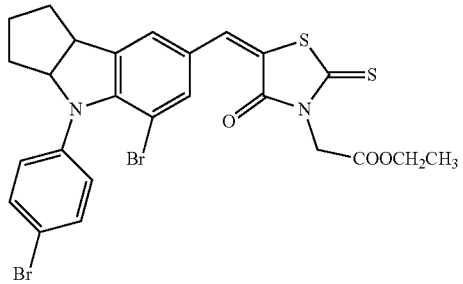
(59)
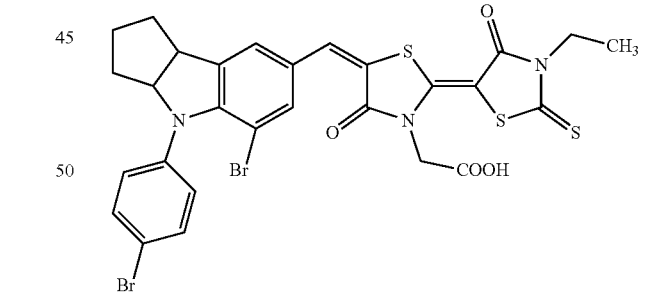
(60)

-continued
(61)
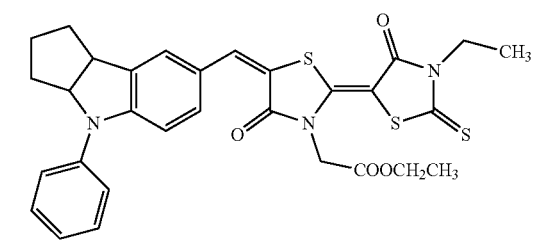
(62)
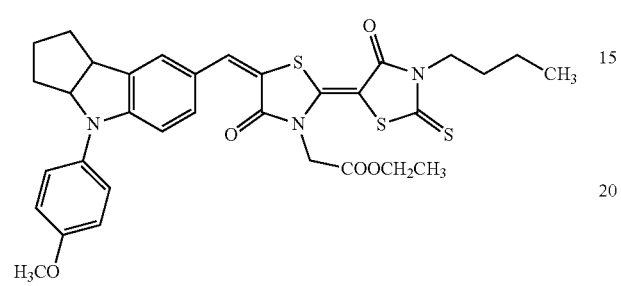
(63)
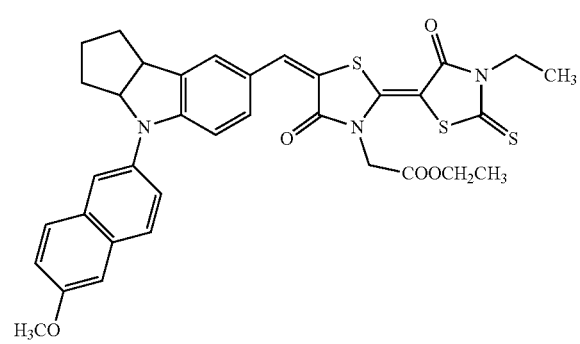
(64)
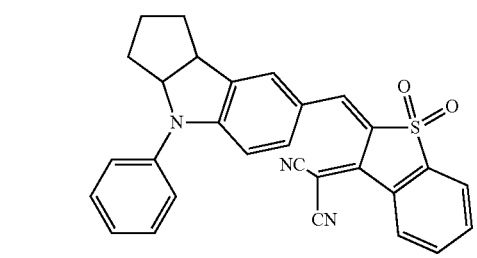
(65)
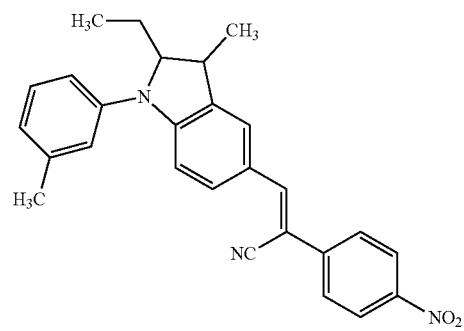
-continued
(66)
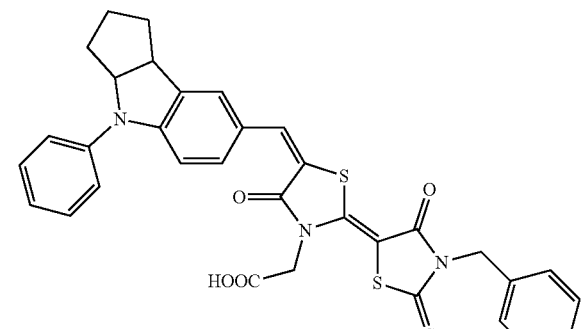
(67)
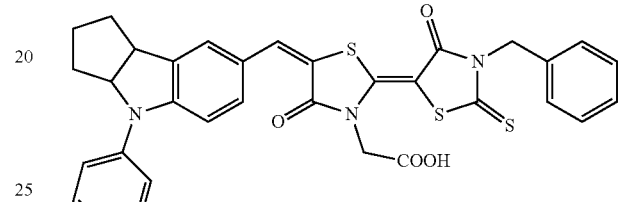
(68)
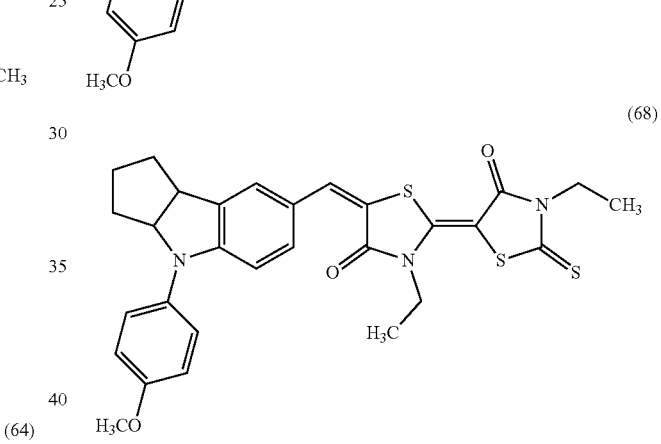
(69)
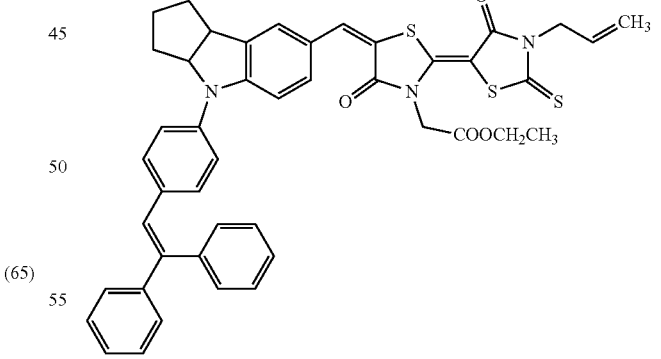
(70)
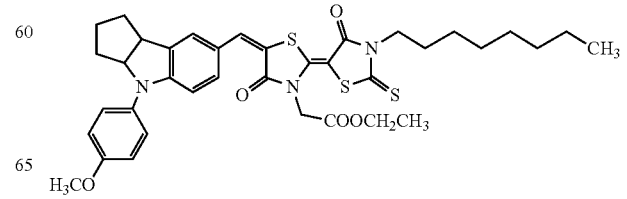

(71)
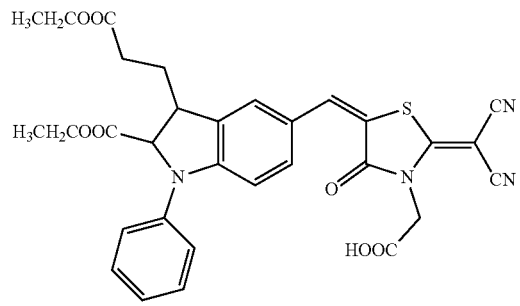
(72)
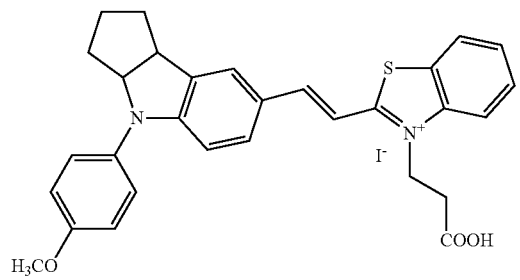
(73)
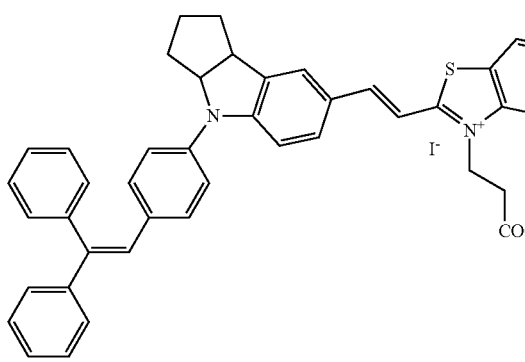
(74)
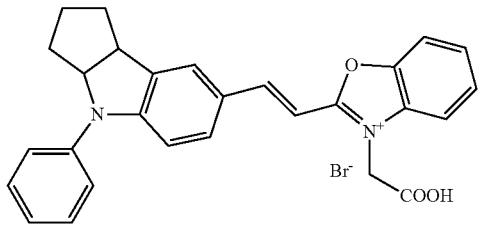
(75)
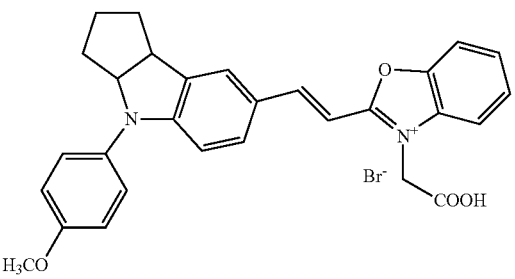
(76)
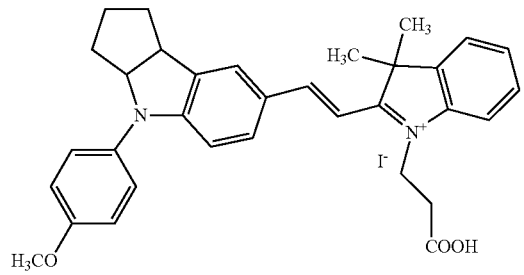
(77)
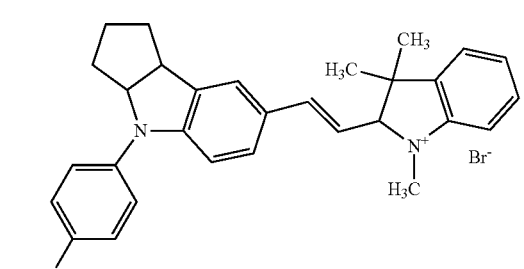
(78)
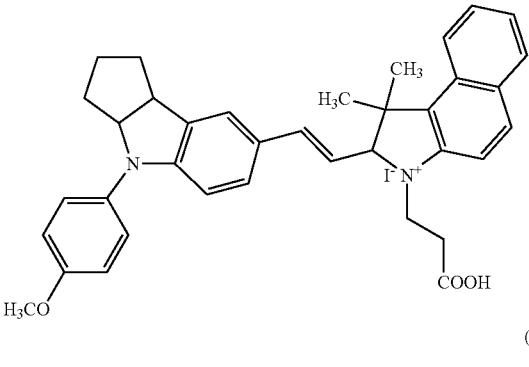
(79)
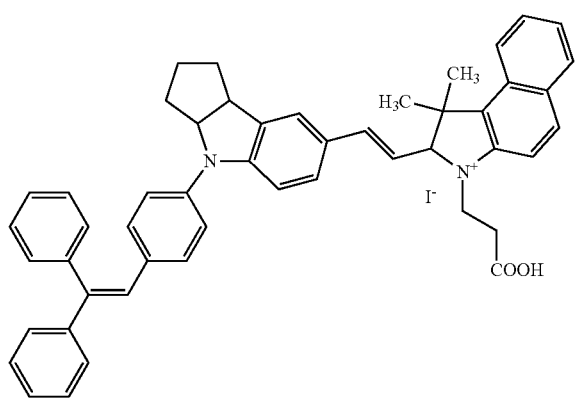
(80)
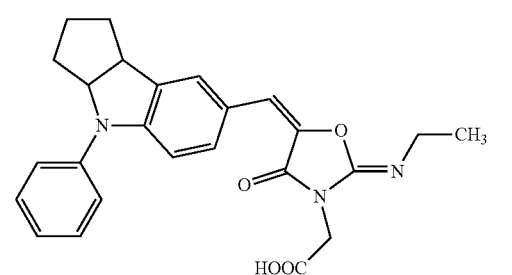

(81)
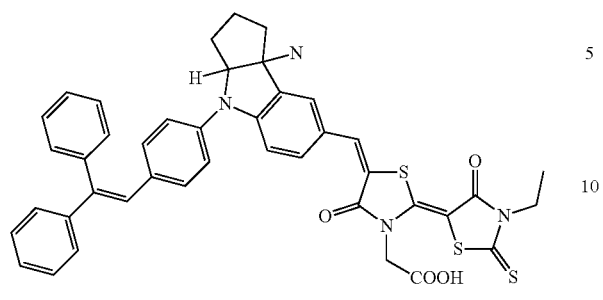
(82)
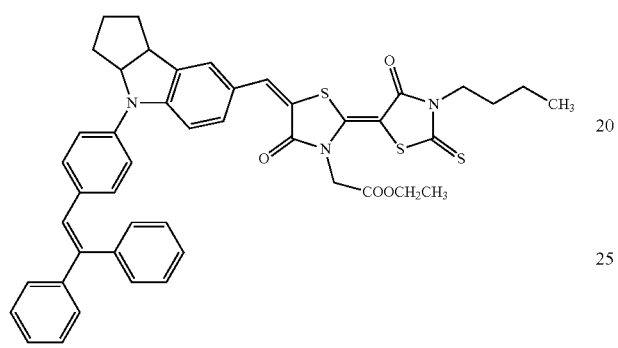
(83)
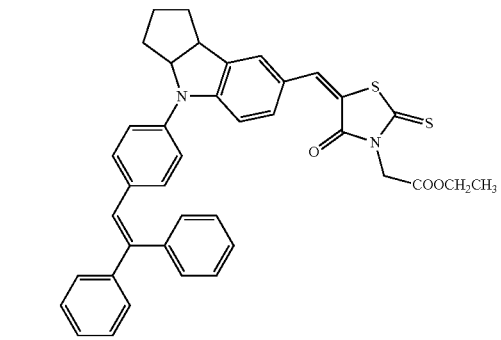
(84)
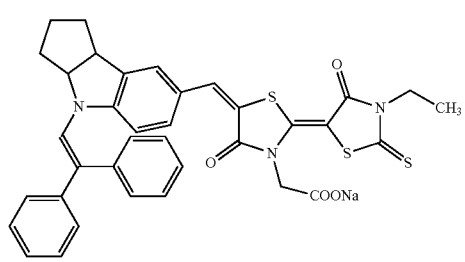
(85)
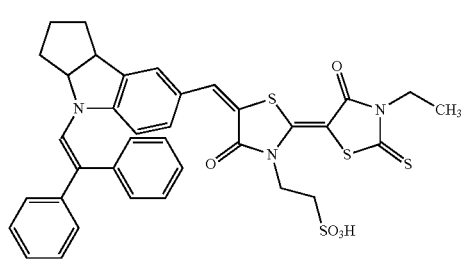
(86)
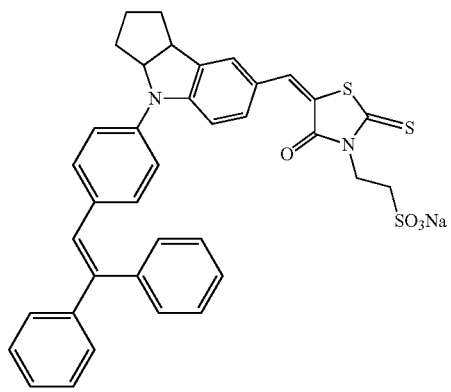
(87)
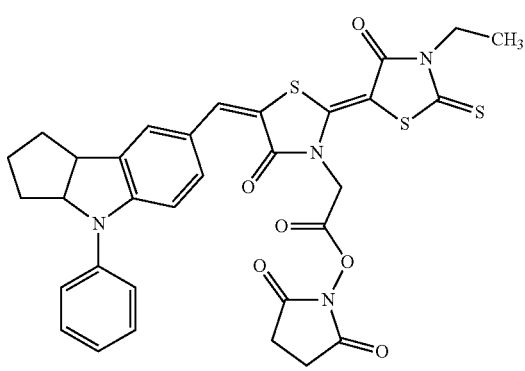
(Chem 8-4)
(88)
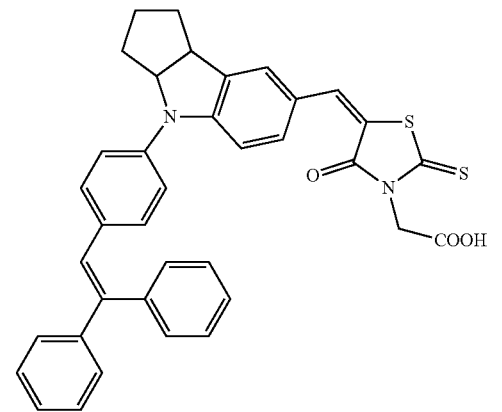
(89)
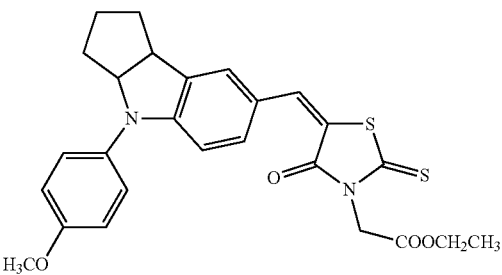

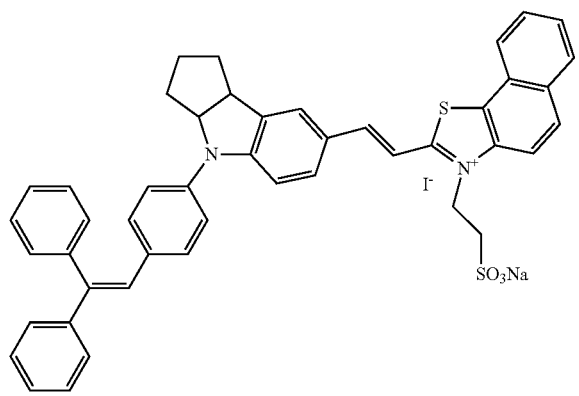
(90)
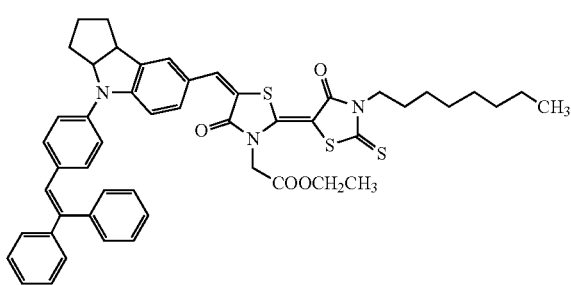
(95)
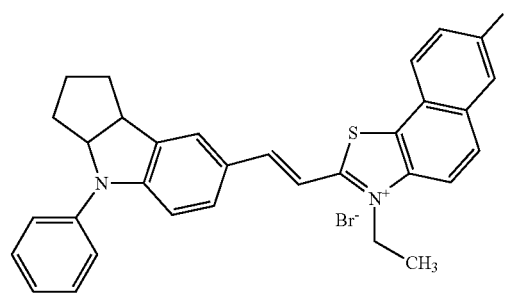
(91)
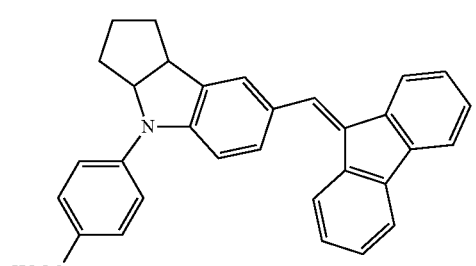
(96)
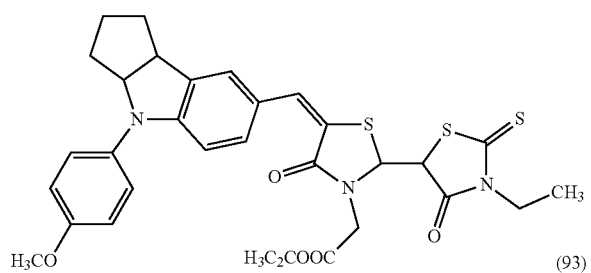
(92)
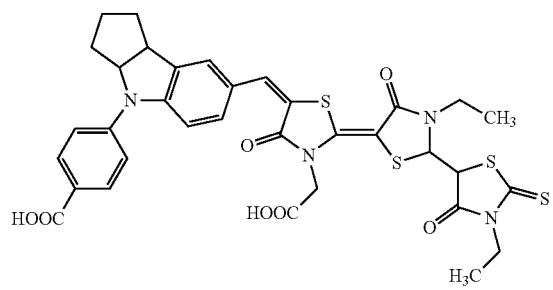
(97)
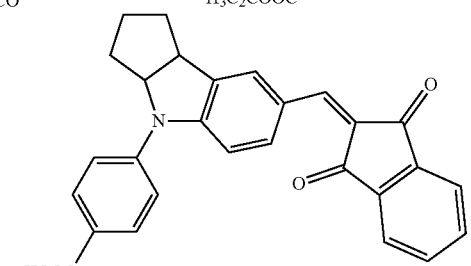
(93)
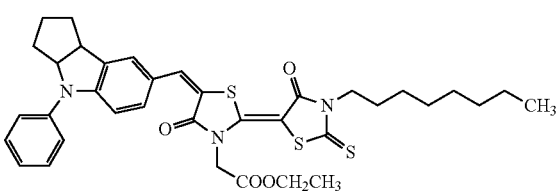
(98)
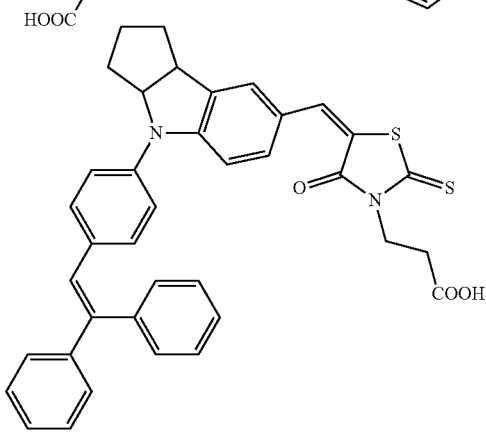
(94)
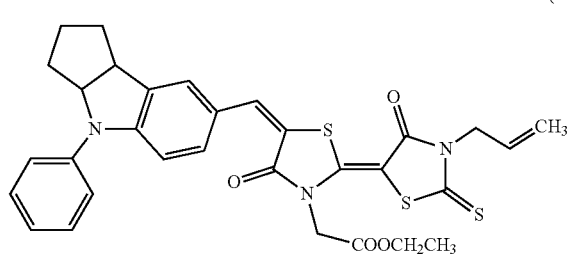
(99)

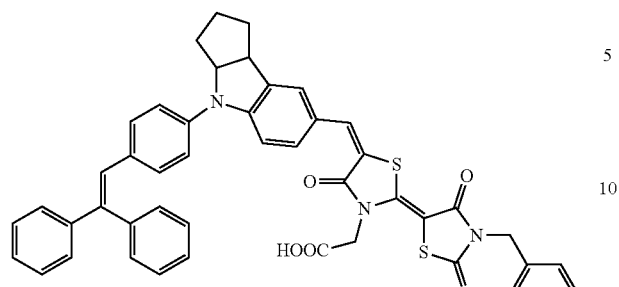
(100)
(101)
(102)
(103)
(104)
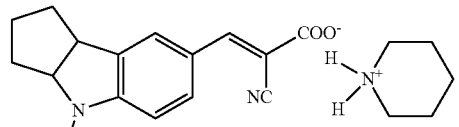
(105)
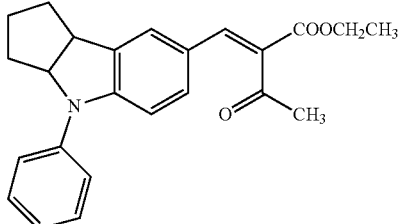
(106)
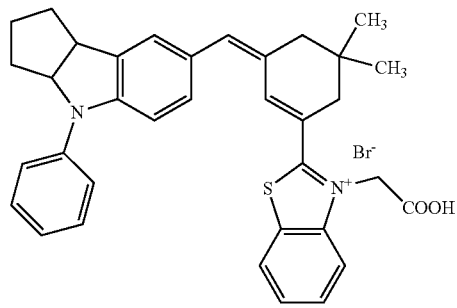
(107)
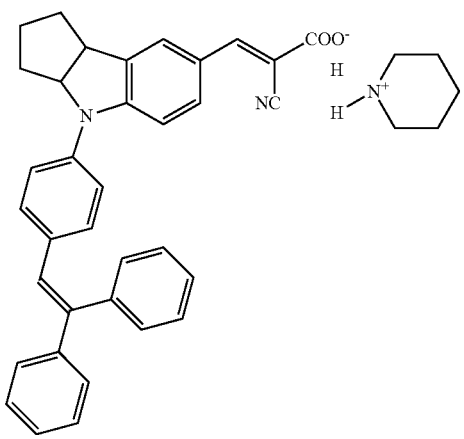
(108)
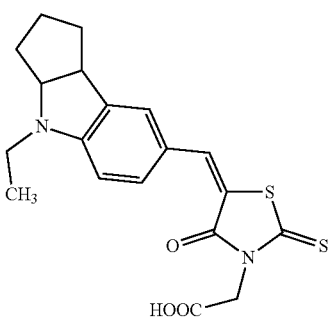
(109)

-continued
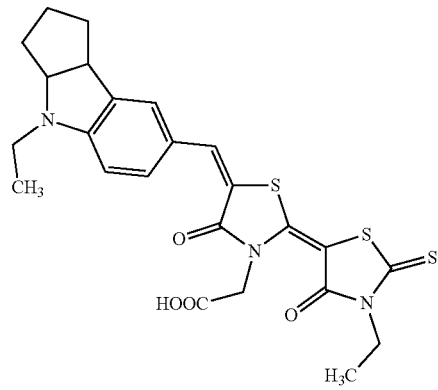
(110)
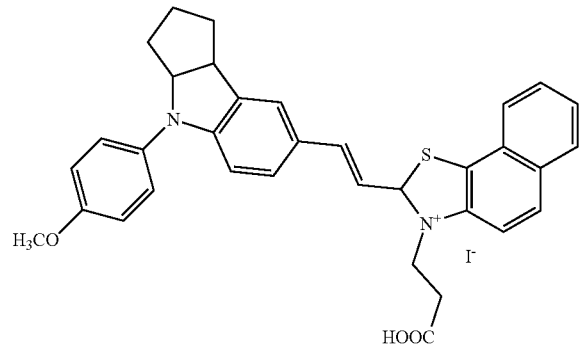
(111)
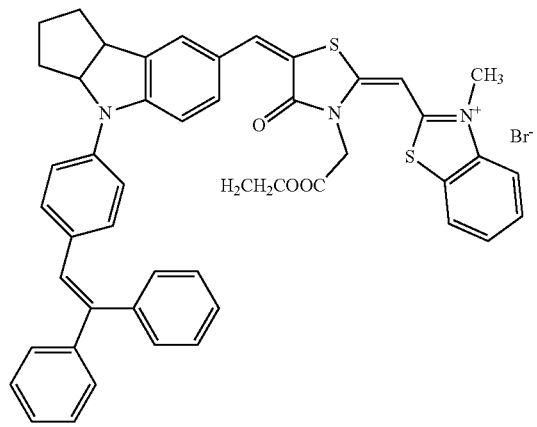
(112)
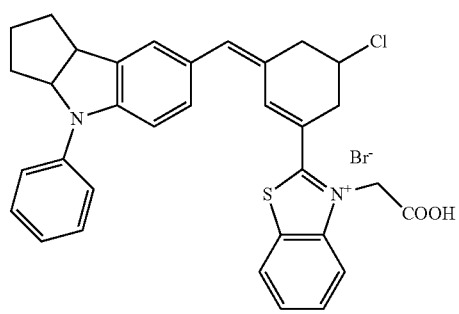
(113)
-continued
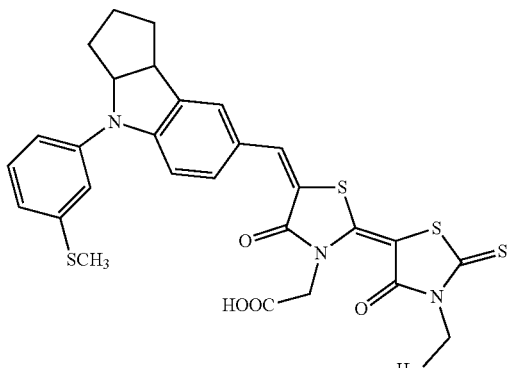
(114)
(Chem 8-5)
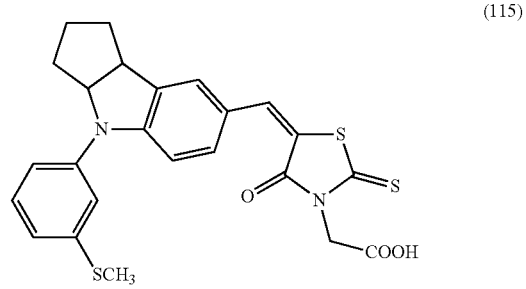
(115)
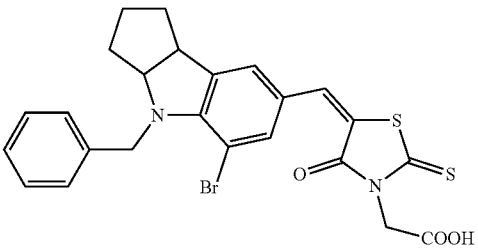
(116)
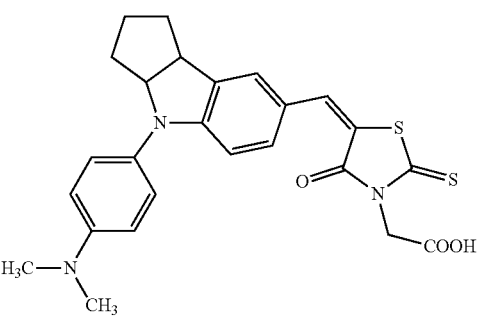
(117)
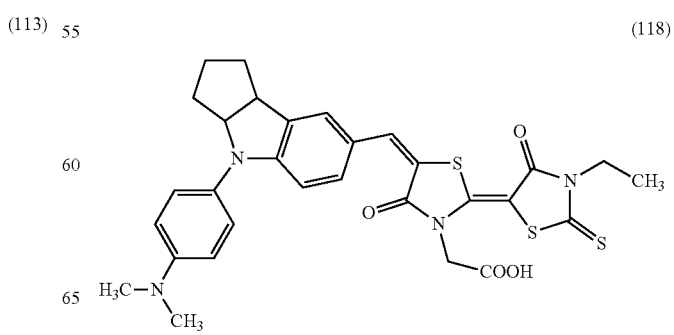
(118)

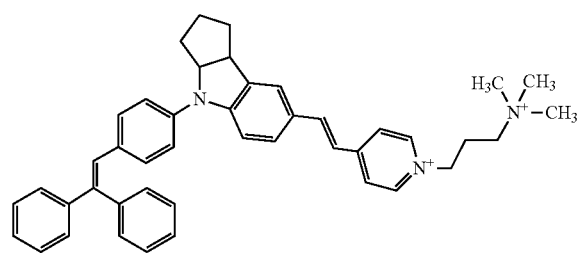
(119)
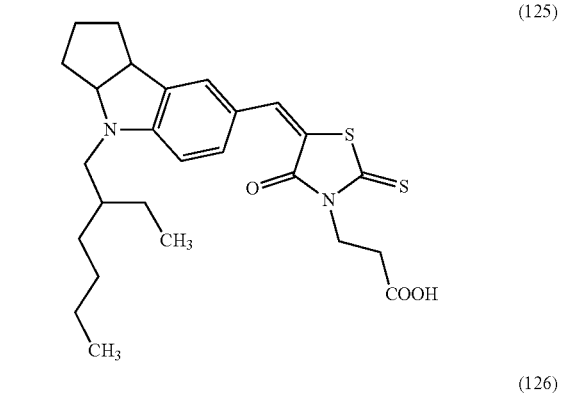
(125)
(120)
(126)
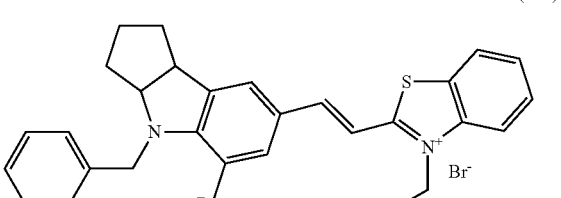
(121)
(127)
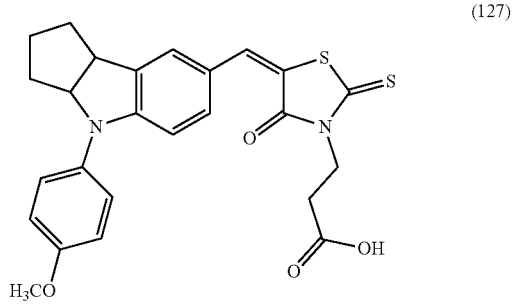
(122)
(128)
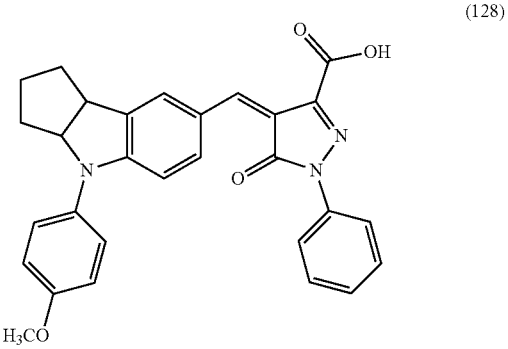
(123)
(129)
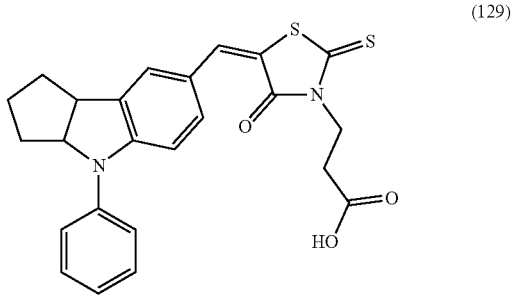
(124)

-continued
(130) 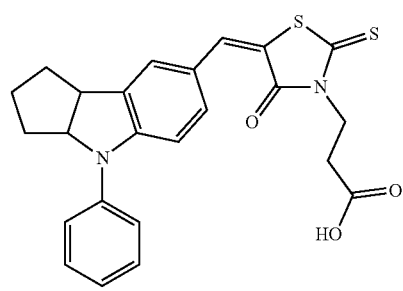
(131) 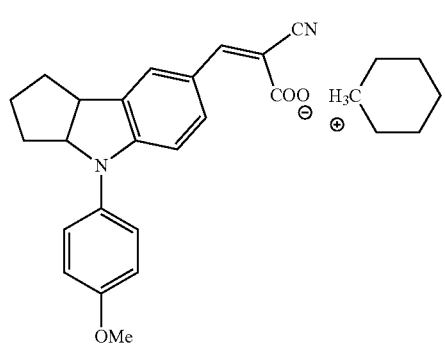
(132) 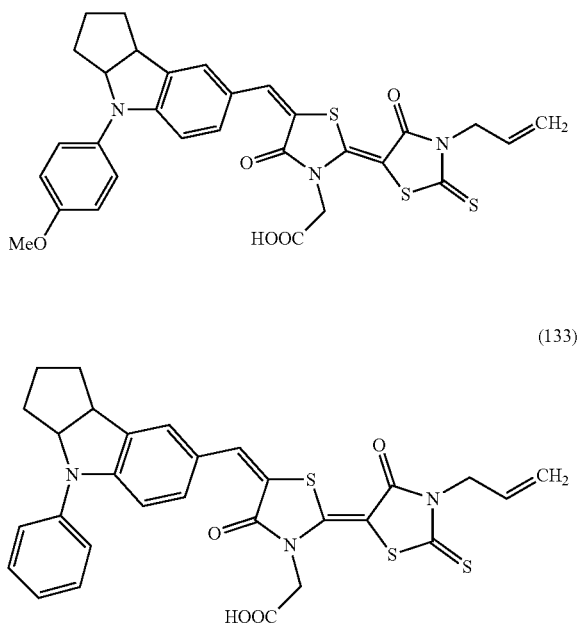
(133)
(134) 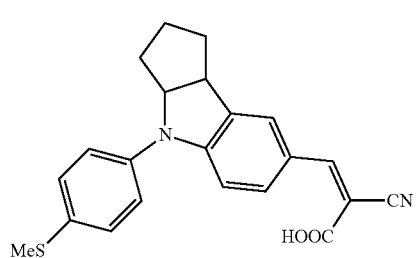
-continued
(135) 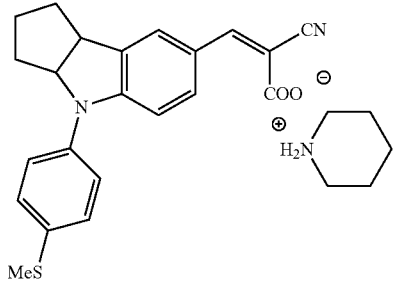
(136) 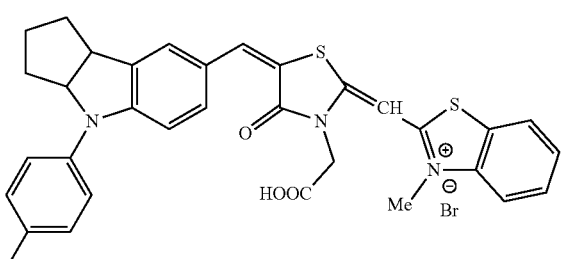
(137) 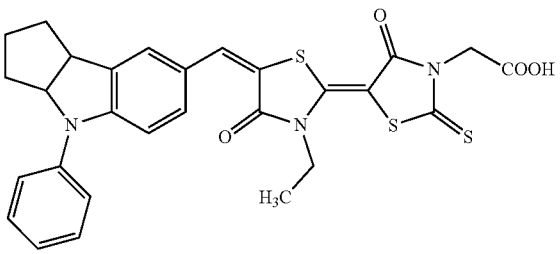
(138) 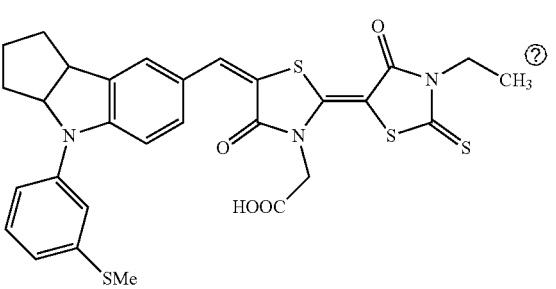
(139) 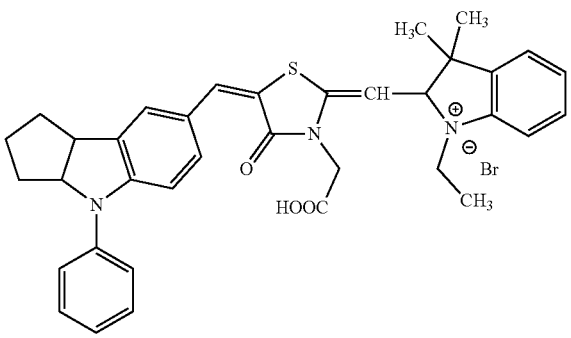

-continued (140)
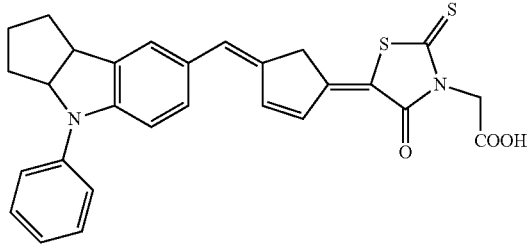

(141)
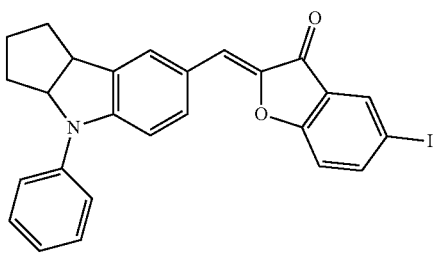

(142)
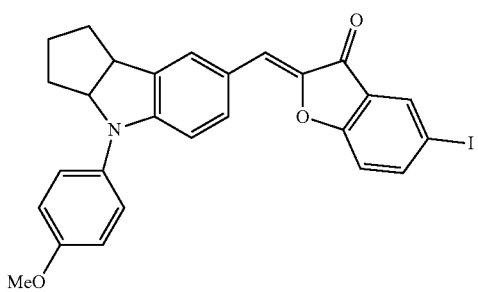

The staining compound according to the present invention has excellent spectral characteristics, also exhibits excellent storage stability, and can label a cell and a cell organ in a living body. Thus, the staining compound can clearly visualize a cell and a cell organ, and can be used as a suitable probe for a biological specimen. Specifically, there are described in detail below.

Labelling can be performed by bringing a biological specimen into contact with a solution of a probe for a biological specimen containing, as an active agent, at least one kind of the compound of the general formula (I) of the present invention. If the probe is a compound having staining property, staining or differential staining is possible. The term "differential staining" as used herein refers to labelling a biological specimen of interest by using multiple kinds of probes for a biological specimen. Sites of a biological specimen to be labelled may be different from or identical to each other. A differential staining step involves bringing a biological specimen into contact with a first probe for a biological specimen and subsequently bringing a second probe for a biological specimen. Further, the biological specimen may be simultaneously brought into contact with the first probe for a biological specimen and the second probe for a biological specimen. If probes for a biological specimen to be used can be distinguished from each other, multiple labels can be confirmed in one-time observation by differential staining.

When the biological specimen is in a living condition (unfixed condition), a labelling solution can be obtained by directly adding the compound of the general formula (I) to various solutions for maintaining the survival of the biological specimen and to the culture solutions for the growth of the biological specimen.

Examples of the biological specimen to be labelled by the method of the present invention include an individual organism, a microorganism, protozoan, a biological tissue, a biological tissue section, a human cell, an animal cell, and a chromosome.

Examples of the biological specimen further include a cell aggregate (spheroid), an oocyte, an embryo, and an individual grown from an embryo. Examples of the individual include individuals in all the processes of developing from a fertilized embryo to an adult of one of a vertebrate or an invertebrate.

Examples of the vertebrate include: small bony fishes such as *Takifugu rubripes*, *Oryzias latipes*, and Zebrafish; small animals such as a rat and a mouse; large animals such as a primate, a pig, and a dog; and a human. Examples of the invertebrate to be used include a *Drosophila* fly and a nematode.

The form of the probe for a biological specimen of the present invention is not particularly limited, and the probe for a biological specimen can be used in a form such as a liquid, a granule, a tablet, a capsule, and a patch. In order to label the inside of a cell or a tissue, in the case of in vivo labelling, the probe may be directly exposed to a tissue to be labelled. More preferably, the probe may be administered to a living body by one of exposure (for example, a liquid) and oral administration to the living body, and may be administered to a living body by, for example, intravascular administration such as intravenous administration and intraarterial administration, peroral administration, sublingual administration, intrarectal administration, intraperitoneal administration, transdermal administration, subcutaneous administration, intradermal administration, intravesical administration, endotracheal (intrabronchial) administration, intraocular administration, transnasal administration, and intraaural administration, which utilize means such as infusion, nebulization, and application.

The probe for a biological specimen of the present invention can be used by dissolving at least one kind of the compound of the general formula (I) in an appropriate solvent. The solvent is not particularly limited as long as it has no influence on a living body, but preferred is an aqueous liquid with high biocompatibility to a living body. Examples of the solvent include: water; physiological saline; buffers such as a phosphate buffer (PBS) and Tris; alcohol-based solvents such as ethanol, ethylene glycol, and glycerin; organic solvents such as DMSO; cell culture media such as D-MEM and HBSS; and infusion solutions such as a lactated Ringer's solution, and particularly preferred is a solvent containing 50% or more of water. Further, two or more kinds of those solvents may be used in mixture.

The dosage of the probe for a biological specimen is not particularly limited as long as a target site can be finally detected, and can be appropriately increased or decreased depending on the kind of the target site and the kind of the probe to be used. In particular, when the probe for a biological specimen is administered in vivo, the smallest possible amount is preferred. Further, when the probe for a biological specimen is administered in vitro, the probe for a biological specimen may be used in an amount that has selectivity for tissue staining and is easy to be distinguished.

The concentration of the probe for a biological specimen to be used is in the range of generally 0.001 nM to 1,000 µM and preferably 0.01 nM to 100 µM.

The administration form, administration route, and dosage for an animal are appropriately selected depending on the body weight and condition of an animal of interest.

The probe for a biological specimen of the present invention may be labelled with a radionuclide.

The kind of the radionuclide used as a label is not particularly limited and may be appropriately selected depending on the usage mode.

The probe for a biological specimen labelled with a radionuclide may be imaged with, for example, autoradiography, positron emission tomography (PET) using a positron emitting nuclide, positron emitting tracer imaging system (PETIS) specialized in plant application, and single photon emission computed tomography (SPECT) using various γ-ray emitting nuclides. Further, the probe for a biological specimen may be detected by magnetic resonance imaging (MRI) utilizing an MR signal derived from a fluorine nucleus and $^{13}C$. In addition, the probe for a biological specimen can be imaged by using a compton camera (GREI) capable of simultaneously imaging multiple molecules as a next-generation molecular imaging apparatus. A distribution condition of a biological specimen can be time-dependently measured and imaged in a noninvasive manner by those methods. Further, a probe for a biological specimen can be quantitatively determined by using, for example, a liquid scintillation counter, an X-ray film, and an imaging plate.

Further, the measurement of the blood (or urinary or fecal) concentration of the probe for a biological specimen labelled with a radioisotope such as $^{14}C$ by using, for example, accelerator mass spectrometry (AMS), can provide pharmacokinetic information (such as area under the blood concentration-time curve (AUC), blood concentration half life ($T_{1/2}$), maximum blood concentration ($C_{max}$), time-to-maximum blood concentration ($T_{max}$), distribution volume, first-pass effect, bioavailability, and urinary and fecal excretion rate) on an unchanged product and a metabolite of a labelled substance.

The radionuclide is not particularly limited and may be appropriately selected depending on the usage mode.

Specifically, in the case of measurement with PET, a positron emitting nuclide such as $^{11}C$, $^{14}C$, $^{13}N$, $^{15}O$, $^{18}F$, $^{19}F$, $^{62}Cu$, $^{68}Ga$, and $^{78}Br$ may be used, for example. Preferred examples include $^{11}C$, $^{13}N$, $^{15}O$, and $^{18}F$, and particularly preferred examples include $^{11}C$ and $^{18}F$.

Further, in the case of measurement with SPECT, a γ-ray emitting nuclide such as $^{99m}Tc$, $^{111}In$, $^{67}Ga$, $^{201}Tl$, $^{123}I$, and $^{133}Xe$ may be used, for example. Preferred examples include $^{99m}Tc$ and $^{123}I$.

In addition, in the case of measurement of animals other than a human, a radionuclide having a longer half life such as $^{125}I$ may be used, for example.

In the case of measurement with GREI, one of $^{131}I$, $^{85}Sr$, and $^{65}Zn$ may be used, for example. The radionuclide may be contained in or bonded to the compound represented by the general formula (I).

A labelling method with the radionuclide is not particularly limited, and a commonly-employed method can be adopted. Further, at least one part of elements of which the compound represented by the general formula (I) is formed may be replaced by or bonded to the radionuclide.

When the compound represented by the general formula (I) is labelled with the radionuclide, the compound preferably has radioactivity of about 1 to 100 μCi per mM.

In this case, the dosage of the probe for a biological specimen to be used is not particularly limited as long as it has no influence, and is appropriately selected depending on the kind of the compound and the kind of the radionuclide used as a label.

For an adult human, the amount of the probe to be used is 0.0001 μg to 1,000 μg and preferably 0.01 μg to 10 μg per day.

Further, to the probe for a biological specimen, preferably added is at least one of a humectant, a surface tension adjusting agent, and a thickener, for example. If a salt concentration and a pH suitable for a living body must be controlled, one of salts such as sodium chloride, various pH adjusting agents, pH buffers, preservatives, antibacterial agents, sweeteners, and flavors may be appropriately added, for example.

The pH adjusting agent is not particularly limited, but preferably adjusts a pH to 5 to 9. Examples thereof include hydrochloric acid, acetic acid, phosphoric acid, citric acid, malic acid, sodium hydroxide, and sodium bicarbonate.

In addition, in order to suppress the pH variation, a pH buffer is preferably added. The pH can be appropriately adjusted by using a weak acid such as phosphoric acid, oxalic acid, citric acid, and acetic acid and a salt thereof in combination.

An imaging method utilizes the probe for a biological specimen of the present invention. For methods of measuring and detecting the probe, a known method to those skilled in the art may be incorporated.

An observation method to be used in the present invention is not particularly limited as long as the method has no influence on both the biological specimen and the probe for a biological specimen, and is a method of capturing a condition and a change of the biological specimen as an image. Examples of the observation method include visible light imaging, near-infrared light imaging, and infrared light imaging, each of which involves irradiating a biological specimen with visible light, near-infrared light, or infrared light, and observing with a camera, CCD, and the like; laser microscopy; fluorescent imaging, fluorescent microscopy, fluorescent endomicroscopy, confocal endomicroscopy, multiphoton-excited fluorescence microscopy, and narrow band imaging, each of which involves irradiating a biological specimen with excitation light from an excitation light source and observing fluorescence derived from a biological specimen emitting light with a fluorescence endoscope etc.; and optical coherence tomography (OCT); and further, soft X-ray microscopy.

Further, the wavelength of excitation light to be used in the present invention is not particularly limited as long as it has no influence on both the biological specimen and the probe for a biological specimen, varies depending on the kind of the probe to be used, and is not particularly limited as long as the probe of the present invention efficiently fluoresces. The wavelength is generally 200 to 1,010 nm, preferably 400 to 900 nm, and more preferably 480 to 800 nm. The wavelength in the case of using light in a near-infrared area is generally 600 to 1,000 nm and preferably 680 to 800 nm excellent in biological permeability.

A fluorescence excitation light source to be used in the present invention is not particularly limited as long as the light source has no influence on both the biological specimen and the probe for a biological specimen, and various laser light sources may be used. Examples thereof include a dye laser, a semiconductor laser, an ion laser, a near-infrared pulse laser, a fiber laser, a halogen lamp, a xenon lamp, and a tungsten lamp. Further, the use of various optical filters allows the acquisition of preferred excitation wavelengths and the detection of only fluorescence.

As mentioned above, if an individual biological specimen has been irradiated with excitation light to cause light emission inside the individual biological specimen and an image of the biological specimen is captured in the condition, a light emitting site can be easily detected. Further, the individual biological specimen can be observed in more detail by combining a bright field image obtained by irradiation with visible light and a fluorescence image obtained by irradiation with excitation light by using an image processing unit.

Many of the probes for a biological specimen among the probes of the present invention have large Stokes' shift. The term "Stokes' shift" as used herein represents a difference between the maximum excitation wavelength and the maximum fluorescence emission wavelength. In general, a measurement error due to excitation light and its scattering light are likely to be generated when Stokes' shift is small. However, the probe for a biological specimen of the present invention is not particularly limited as long as it causes no problem in detection. By selecting a proper probe from two or more kinds of probes for a biological specimen depending on the purposes, multiple sites in a biological specimen can be simultaneously detected with light at single excitation wavelength, and the same site in a biological specimen can be observed in more detail based on a difference between fluorescence emission wavelengths.

Further, the use of a diagnostic medicament containing a radionuclide-labelled probe for a biological specimen allows a biological specimen to be easily imaged by using one of PET, PET-CT, SPECT, MRI, and GREI, for example.

The probe for a biological specimen of the present invention can be screened by using a biological specimen, for example, Zebrafish. In addition, the probe is administered to Zebrafish as a living organism (in vivo), and hence, the screening for safety of the probe for a biological specimen can be simultaneously observed.

In recent years, in U.S. and U.K., Zebrafish has been recognized as a third model animal following a mouse and a rat. Further, it is being clarified that, in a comparison to human, Zebrafish has an 80% homology in terms of the full genome sequence, is almost the same in terms of the number of genes, and is very similar also in terms of the development and structure of principal organs and tissues. It is particularly preferred that Zebrafish be used for screening as a model animal because Zebrafish has a feature that a process in which the respective parts (organs such as heart, liver, kidney, and gastrointestinal tract) are differentiated and formed from fertilized embryos can be observed through its transparent body.

It is shown that Zebrafish is histologically very similar to a human with respect to principal tissues such as retina, brain, and liver, and actions of many of known drugs on Zebrafish are equivalent to those on a human. It is also revealed that a compound first identified in Zebrafish has a similar activity in mammals. Those facts suggest that Zebrafish should be greatly extrapolated to a human. In addition, it is shown that Zebrafish is useful as a movement disease model animal, is very similar to a human with respect to an immune system, is useful as an ophthalmic disease model animal, and is very homologous to a human in a wide range of areas such as an application to screening for acoustic nerve toxicity. Therefore, applications such as screening for the toxicity of a compound and screening for a medicament each using Zebrafish are also being performed.

Specifically, there is exemplified a screening method involving bringing Zebrafish into contact with the probe for a biological specimen of the present invention, and observing an influence of the probe for a biological specimen on Zebrafish. The screening allows the toxicity of the probe for a biological specimen to be objectively assessed.

Further, simultaneously, in the probe for a biological specimen of the present invention, sites to be labelled of a body tissue of Zebrafish are different from each other depending on the kind of the probe. Each of different sites of a body tissue of Zebrafish could not labelled until such a low molecular weight compound as the probe for a biological specimen is used. As target sites, there are exemplified nose, blood vessel, liver, capillary cell, lateral line, skin, tumor, cancer cell, esophagus, stomach, duodenum, small intestine, large intestine, rectum, oral cavity, urinary cavity, and fat.

Further, multiple probes for a biological specimen for staining different sites of a body tissue can be easily prepared by simply changing a substituent in a skeleton of the general formula (I) of the present invention. In addition, those multiple probes for a biological specimen may differ from each other in the excitation wavelength and the fluorescence emission wavelength. Therefore, the probes can be simultaneously administered, which enables multiple staining (simultaneous differential staining with multiple colors). Unlike conventionally known nucleic acid staining agents which nonspecifically label the whole tissue of a living body, the probe for a biological specimen of the present invention can effectively label a specific site. Further, many of the probes of the present invention can label multiple sites with one probe. In this case, multiple sites can be simultaneously monitored. The probe of the present invention can label a specific site with high contrast, and as a result, morphological features such as a size and a shape can be precisely imaged. In particular, the imaging of a disease-related site and the monitoring of its time-dependent change are particularly useful. That is, the monitoring enables the progression and cure of a disease to be objectively evaluated.

The probe for a biological specimen of the present invention based on the site to be labelled can be used for application to a molecular imaging technology. For example, the speed of drug discovery including screening becomes faster, with the result that a cost reduction can be achieved. Further, the probe is also applicable to the development of high precision diagnosis and treatment method for new diseases. In addition, the probe can be used for a life science research to understand unexplained phenomena, for example, and thus may become an effective basic technology that dramatically develops the industry. A method of administering the probe for a biological specimen is not particularly limited. When the probe for a biological specimen is water-soluble, there is exemplified a method of administering the probe for a biological specimen into rearing water. When the probe for a biological specimen is non-water-soluble, there are exemplified a method of administrating the probe for a biological specimen by dispersing the probe alone into rearing water, a method of administrating the probe for a biological specimen together with a trace amount of a surfactant and DMSO, a method of orally administering the probe for a biological specimen mixed in a feed for Zebrafish, and a method of parenterally administering the probe for a biological specimen with injection and the like. It should be appreciated that it does not cause any problem whether the probe for a biological specimen is of a completely dissolved state or is used in a suspended state in a medium containing water. A method of administering the probe for a biological specimen into rearing water is preferred, because which can be easily performed. Thus, the probe for a biological specimen is desirably water-soluble, and also desirably contains a carboxylic acid group and a sulfonic acid group in the compound.

The probe for a biological specimen of the present invention is expected to be used as, for example, an index in evaluation and screening for safety such as effects, adverse effects, general toxicity, neurodevelopmental toxicity, reproductive developmental toxicity, genetic toxicity, and carcinogenicity of a chemical substance. For example, at least one kind of the probe for a biological specimen, Zebrafish as the biological specimen, and a chemical substance to be examined can be used to perform in vivo screening for an influence on an organism. The probe for a biological specimen can be selected as needed depending on, for example, sites to labelled, purposes, and test means. The above-mentioned chemical substance means a collective term of substances each having a chemical action and is not particularly limited, and examples thereof include a pharmaceutical agent, an organic compound, a therapeutic agent, an investigational drug, an agricultural chemical, a cosmetic, an environmental pollutant, and an endocrine disruptor.

Zebrafish is not limited to wild-type Zebrafish and various disease-based models of Zebrafish may be used depending on the purpose of screening. In the case of a disease-based model, the model can be applied for screening for evaluating an effect and safety of a new drug candidate compound by using the probe for a biological specimen of the present invention as an index.

A method of administering a test compound is not particularly limited. When the test compound is water-soluble, there is exemplified a method of administering the test compound into rearing water. When the test compound is non-water-soluble, there are exemplified a method of administering the test compound and a trace amount of a surfactant into a rearing water, a method of orally administering the test compound mixed in a feed for Zebrafish, and a method of parenterally administrating the test compound with an injection and the like.

A screening method of the present invention is highly excellent in terms of a speed and a cost compared with methods each using a mouse, a rat, and the like, because Zebrafish is easy in feeding and propagation and low in market price, and has principal organs and tissues, the basic structures of which are formed in 48 to 72 hours after fertilization.

It is also possible to take a method for the screening, which involving bringing a biological specimen, for example, Zebrafish into contact with the probe for a biological specimen of the present invention, taking out the labelled site (ex vivo), and observing the staining property of the probe for a biological specimen. In addition, it is expected that the staining property of the probe for a biological specimen would be utilized for application development such as development of high precision diagnosis and treatment method for diseases.

The probe for a biological specimen of the present invention can be used for screening the staining property of a tissue and a cell taken out from a biological specimen (in vitro). In addition, it is expected that the staining property of the probe for a biological specimen would be utilized for application development such as development of high precision diagnosis and treatment method for diseases. For example, it is expected that the probe for a biological specimen of the present invention would be used for cytology involving sampling one part of tissues and cells as targets in a trace amount by aspiration with a puncturing cytodiagnostic device and the like, staining the sample with the probe for a biological specimen of the present invention, and assessing the form, kind, and benignancy and malignancy, and the like of the cell.

The probe for a biological specimen of the present invention can be used as means for assessing a difference from a normal cell through labelling with application and the like of a cell tissue suffering from a disease and a site suspected of a tumor during an operation, for example. There also exists an application method involving spraying, as necessary, the probe for a biological specimen of the present invention, which has been stocked in advance inside a diagnostic device or a therapeutic device such as an endoscope, a capsule endoscope, a fiberscope endoscope, and a soft endoscope, onto a part suspected of a tumor and the like, to thereby specify a tumor site. In addition, devices such as a catheter are inserted into, for example, body cavities such as a thoracic cavity and a peritoneal cavity, luminal cavities such as a gastrointestinal tract and an urinary duct, and blood vessel, and the probe for a biological specimen of the present invention can also be drip infused together with a medicament and the like. Further, after the probe for a biological specimen of the present invention has been incorporated into a drug eluting stent and a coat tube of a guide wire, the location can also be confirmed from the outside with an X-ray and the like. A diagnostic device or a therapeutic device each using those probes incorporated therein may also be provided as a kit including a device and a separate probe in combination.

The present invention also encompasses a biological specimen detecting system obtained by combining a probe for a biological specimen of the present invention and a unit for detecting the probe. The unit for detecting the probe may include a unit for exciting a probe and a unit for detecting an optical signal transmitted from the probe.

The probe for a biological specimen of the present invention can be used for diagnosis. Further, the probe can be used as a diagnostic composition containing at least one of the probes for a biological specimen. The usage of the probe for a biological specimen of the present invention is not particularly limited, and for example, the use of a diagnostic substance labelled with the probe for a biological specimen of the present invention is possible, and the use and application as a diagnostic medicament containing the diagnostic substance is also possible.

EXAMPLES

Next, the present invention is described in more detail by way of examples, and the present invention is not limited thereto. A $^1$H-NMR spectrophotometer (ECA-400, manufactured by JEOL Ltd.), LC/TOF MS (LC/MSD TOF, manufactured by Agilent Technologies, Inc.), and a spectral scanning multimode reader (Varioskan Flash, manufactured by Thermo Fisher Scientific Inc.) were used as analyzers.

Synthesis Examples of Compounds

Next, Synthesis Examples 1 and 2 are described as typical synthesis examples of compounds. The change of an aldehyde derivative and a compound (B) and the heating under reflux together with one of an appropriate acid and base can afford a target compound.

Synthesis Example 1

Synthesis of Staining Compound (1)

To a solution obtained by dissolving 3.0 g (11.4 mmol) of an aldehyde derivative (A-2) in 20 mL of acetic acid, added were 2.2 g (11.5 mmol) of a compound (B-20) and 0.9 g of ammonium acetate, followed by stirring under reflux for 2 hours. After completion of the reaction, 50 mL of water were slowly added dropwise thereto while cooling, and the mixture was cooled to room temperature. A solid precipitate was filtrated, washed with 100 mL of water twice, and further washed with 50 mL of 2-propanol, to thereby afford 3.2 g (yield: 64.4%) of a target product (1).
[Analysis Result of Compound (1)]

[1] $^1$H NMR (400 MHz, DMSO-$d_6$, room temperature): δ [ppm]=1.36-1.40 (m, 1H), 1.63-1.81 (m, 4H), 2.04-2.08 (m, 1H), 3.89 (t, 1H, J=8.47 Hz), 4.73 (s, 2H), 5.06 (t, 1H, J=7.10 Hz), 6.93 (d, 1H, J=8.24 Hz), 7.15 (t, 1H, J=7.10 Hz), 7.38-7.46 (m, 6H), 7.74 (s, 1H).

FIG. 1 illustrates a spectrum thereof.

[2] Mass spectrometry (ESI-TOF): m/z=435.0859 (M)$^-$.

Synthesis Example 22

Synthesis of Staining Compound (7)

To a solution obtained by dissolving 3.43 g (10.0 mmol) of an aldehyde derivative (A-16) in 20 mL of toluene, added were 1.13 g (10.0 mmol) of a compound (B-7) and 2.5 g (30.0 mmol) of piperidine, followed by stirring under reflux for 2.5 hours. After completion of the reaction, the mixture was cooled to room temperature, diluted with 100 mL of toluene, supplemented with 100 mL of water, and stirred. After the whole had been left to stand still, an organic layer was separated and dried over anhydrous sodium sulfate. After filtration, toluene was distilled off under reduced pressure, and recrystallization of the residue from ethanol afforded 1.3 g (yield: 31.7%) of a target product (7).
[Analysis Result of Compound (7)]

[1] $^1$H NMR (400 MHz, DMSO-$d_6$, room temperature): δ [ppm]=1.36-1.47 (m, 1H), 1.64-1.81 (m, 4H), 2.04-2.13 (m, 1H), 3.90 (t, 4H, J=8.93 Hz), 5.18 (s, 1H), 6.89 (d, 1H, J=8.24 Hz), 7.19 (dd, 1H, J=2.52, 8.93 Hz), 7.34 (d, 1H, J=2.29 Hz), 7.55 (dd, 1H, J=2.29, 8.70 Hz), 7.75 (d, 1H, J=8.7 Hz), 7.83 (t, 2H, J=4.58 Hz), 7.89 (d, 1H, J=8.7 Hz), 7.95 (s, 1H), 8.07 (s, 1H).

[2] Mass spectrometry (ESI-TOF): m/z=409.1574 (M)$^-$.

Figure 2:
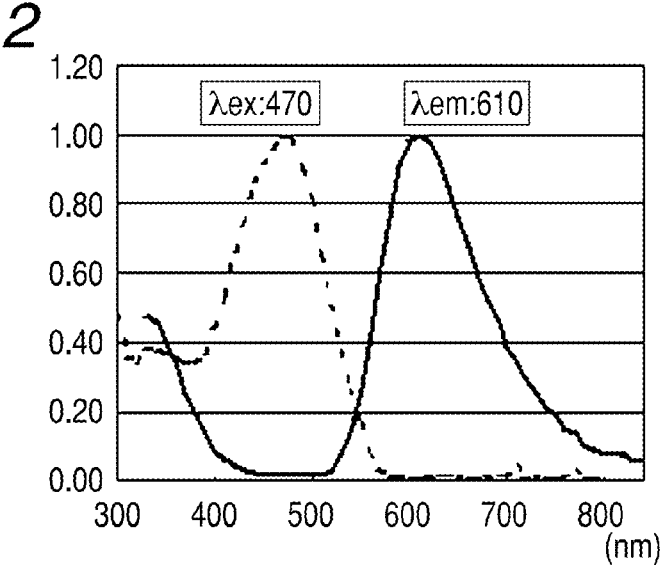
FIG. 2 illustrates spectral shifts of an excitation wavelength λex and a fluorescence emission wavelength λem of a staining compound (7) of the present invention.

FIG. 2 illustrates spectral shifts at the excitation wavelength λex and the fluorescence emission wavelength λem of the staining compound (7).

Example 1

[In Vivo Labelling with Probe for Biological Specimen]

Five juveniles of Zebrafish were put into one well of a well plate together with rearing water. After rearing water had been discharged, 1 mL of distilled water was added to the well, and a solution of a staining compound (1) in DMSO was further added thereto so as to achieve a concentration of 10 ng/mL, followed by gentle stirring (pipetting). Further, Egg Water was prepared by dissolving artificial seawater SEALIFE (manufactured by Marinetech Co., Ltd.) in distilled water at a concentration of 60 mg/L. After the whole had been left to stand for 1 hour, distilled water in the well was discharged and replaced by 1 mL of fresh Egg Water. In addition, such an operation that Egg Water was discharged and replaced by 1 mL of fresh Egg Water was repeated twice. One of the juveniles was taken out from the well onto a dish, supplemented with 100 μL of a 3% methylcellulose aqueous solution to fix the movement of the juvenile, and photographed with a stereoscopic microscope (MZ10F: manufactured by Leica Microsystems K.K.).

Next, the juvenile was embedded in a 5% low temperature melting agarose gel, and a gastrointestinal tract section was prepared with a linear slicer PRO7 (manufactured by Dosaka EM Co., Ltd.). The prepared gastrointestinal tract section was mounted on a slide glass and photographed with a stereoscopic microscope.

This example may include a compound screening method of examining properties and features of a probe for a biological specimen itself.

Examples 2 to 78

The same operation as that in Example 1 was performed except that the staining compound (1) used in Example 1 was changed to any one of the staining compounds described in Table 1.

Figure 3:
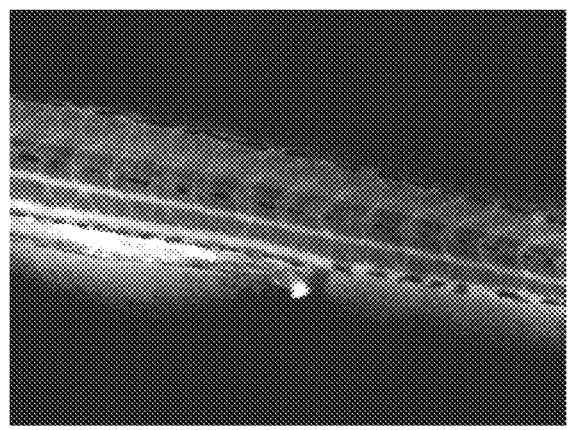
FIG. 3 shows a photograph of a part (blood vessel) observed in Example 6.
Figure 4:
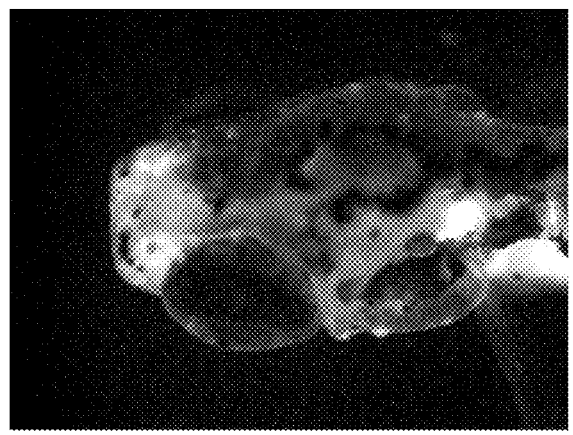
FIG. 4 shows a photograph of a part (nose) observed in Example 15.
Figure 5:
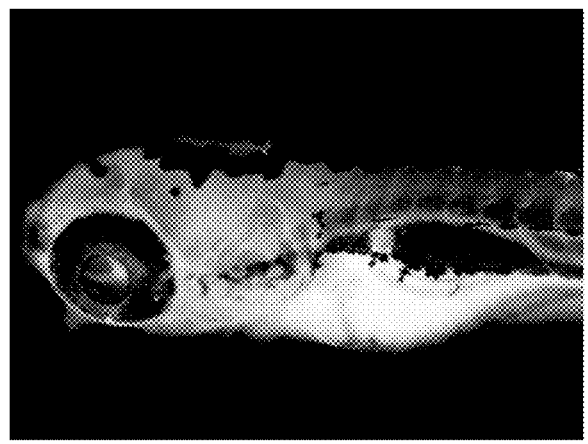
FIG. 5 shows a photograph of a part (blood vessel, liver, gallbladder, and gastrointestinal tract) observed in Example 52.
Figure 6:
FIG. 6 shows a photograph of a part (intrinsic fluorescence) observed in a condition without any staining agent exposure.
Figure 7:
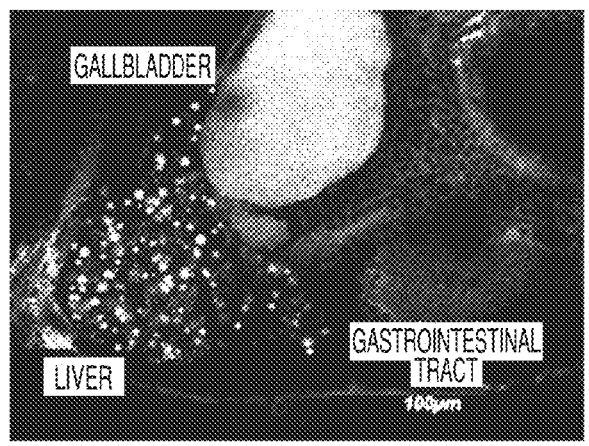
FIG. 7 shows an enlarged photograph of a part (liver, gallbladder, and gastrointestinal tract) observed in Example 52.

FIGS. 3 to 7 each show a typical photograph. FIG. 3 shows a photograph of a part (blood vessel) observed in Example 6. FIG. 4 shows a photograph of a part (nose) observed in Example 15. FIG. 5 shows a photograph of a part (blood vessel, liver, gallbladder, and gastrointestinal tract) observed in Example 52. FIG. 6 shows a photograph of a part (intrinsic fluorescence) observed in a condition that there is no expose to a staining agent. FIG. 7 shows an enlarged photograph of a part (liver, gallbladder, and gastrointestinal tract) observed in Example 52.

Comparative Examples 1 and 2

The same operation as that in Example 1 was performed except that the staining compound (1) used in Example 1 was changed to any one of indocyanine green (ICG) and fluorescein.
<Evaluation>
[Staining Property]

The staining property of each of the staining compounds of Labelled Examples 1 to 78 and Labelled Comparative Examples 1 and 2 was visually evaluated (+++: stained and –: no stained).

[Fluorescence Sensitivity]

The fluorescence intensity of each of the staining compounds of Labelled Examples 1 to 78 and Labelled Comparative Examples 1 and 2 was visually evaluated (+++: strongly observed, ++: moderately observed, +: weakly observed, and –: no stained).

[Storage Stability]

A 10 ng/mL solution of each of the staining compounds of Labelled Examples 1 to 78 and Labelled Comparative Examples 1 and 2 in DMSO was prepared, charged into a well-closed container made of glass, and left to stand still at normal temperature for 1 month. The absorbance and the fluorescence intensity at the time of the start of a storage stability test were measured at a given wavelength, and their rates of change were examined (+++: rates of change of the absorbance and the fluorescence intensity are less than 5%, and thus, the storage stability is highly excellent; ++: rates of change of the absorbance and fluorescence intensity are 5 to 15%, and thus, the storage stability is excellent; and –: rates of change of the absorbance and fluorescence intensity are more than 15%, and thus, the storage stability is poor).

The results of Examples 1 to 78 and Comparative Examples 1 and 2 are shown in Tables 1 to 2, respectively. It should be noted that the excitation wavelength and the fluorescence emission wavelength of the staining compound were determined by measuring an aqueous solution, which had been obtained by diluting 500-fold a 10 mg/mL solution of the staining compound in DMSO with purified water, with a fluorescence spectrophotometer FL 4500 manufactured by Hitachi High-Technologies Corporation.

TABLE 1

| | Dye | Excitation wavelength λex | Fluorescence emission wavelength λem | Stokes' shift λex − λem | Site(s) to be labelled | Staining property | Fluorescence sensitivity | Storage stability |
|---|---|---|---|---|---|---|---|---|
| Example 1 | 1 | 531 | 633 | 102 | blood vessel, gallbladder, and gastrointestinal tract | +++ | +++ | +++ |
| Example 2 | 2 | 482 | 609 | 127 | blood vessel, liver, and gastrointestinal tract | +++ | +++ | +++ |
| Example 3 | 3 | 525 | 607 | 82 | blood vessel, gallbladder, and gastrointestinal tract | +++ | +++ | +++ |
| Example 4 | 5 | 482 | 580 | 98 | liver, gallbladder, and gastrointestinal tract | +++ | ++ | +++ |
| Example 5 | 6 | 474 | 610 | 136 | blood vessel, gastrointestinal tract, and gallbladder | +++ | +++ | +++ |
| Example 6 | 7 | 498 | 601 | 103 | blood vessel and liver | +++ | +++ | +++ |
| Example 7 | 11 | 588 | 668 | 80 | blood vessel, liver, and gastrointestinal tract | +++ | ++ | +++ |
| Example 8 | 13 | 477 | 567 | 90 | liver and gastrointestinal tract | +++ | ++ | +++ |
| Example 9 | 14 | 610 | 675 | 65 | gallbladder | +++ | ++ | +++ |
| Example 10 | 17 | 527 | 636 | 109 | blood vessel, liver, and gastrointestinal tract | +++ | +++ | +++ |
| Example 11 | 18 | 570 | 699 | 129 | blood vessel, gallbladder, and gastrointestinal tract | +++ | +++ | +++ |
| Example 12 | 20 | 533 | 661 | 128 | blood vessel, liver, and gastrointestinal tract | +++ | +++ | +++ |
| Example 13 | 22 | 570 | 598 | 28 | liver and gastrointestinal tract | +++ | +++ | ++ |
| Example 14 | 23 | 545 | 636 | 91 | nose | +++ | +++ | +++ |
| Example 15 | 24 | 566 | 611 | 45 | nose | +++ | +++ | +++ |
| Example 16 | 25 | 394 | 554 | 160 | blood vessel, liver, gallbladder, and gastrointestinal tract | +++ | ++ | +++ |
| Example 17 | 29 | 518 | 575 | 57 | blood vessel, gallbladder, and liver | +++ | +++ | +++ |
| Example 18 | 30 | 502 | 644 | 142 | blood vessel, gallbladder/liver, and gastrointestinal tract | +++ | +++ | +++ |
| Example 19 | 31 | 560 | 677 | 117 | nose | +++ | +++ | +++ |
| Example 20 | 34 | 570 | 657 | 87 | nose | +++ | +++ | +++ |
| Example 21 | 35 | 611 | 720 | 109 | nose | +++ | +++ | ++ |
| Example 22 | 37 | 571 | 648 | 77 | blood vessel, gastrointestinal tract, and gallbladder | +++ | +++ | ++ |
| Example 23 | 38 | 582 | 679 | 97 | blood vessel, liver, gallbladder, and gastrointestinal tract | +++ | +++ | +++ |
| Example 24 | 40 | 576 | 657 | 81 | blood vessel, liver, and gastrointestinal tract | +++ | +++ | +++ |
| Example 25 | 42 | 563 | 618 | 55 | skin surface, liver, and gastrointestinal tract | +++ | +++ | ++ |
| Example 26 | 43 | 569 | 649 | 80 | blood vessel, liver, gallbladder, and gastrointestinal tract | +++ | +++ | +++ |
| Example 27 | 44 | 510 | 558 | 48 | liver and gastrointestinal tract | +++ | +++ | ++ |
| Example 28 | 45 | 401 | 516 | 115 | nose | +++ | +++ | +++ |
| Example 29 | 46 | 610 | 675 | 65 | nose | +++ | +++ | +++ |
| Example 30 | 50 | 481 | 586 | 105 | blood vessel, gastrointestinal tract, and gallbladder | +++ | +++ | ++ |
| Example 31 | 51 | 582 | 670 | 88 | gallbladder and gastrointestinal tract | +++ | + | ++ |
| Example 32 | 54 | 610 | 633 | 23 | gastrointestinal tract and nose | +++ | ++ | +++ |
| Example 33 | 56 | 437 | 585 | 148 | liver, gallbladder, and gastrointestinal tract | +++ | +++ | +++ |
| Example 34 | 59 | 559 | 671 | 112 | blood vessel, nose, and gastrointestinal tract | +++ | +++ | +++ |
| Example 35 | 60 | 563 | 609 | 46 | gastrointestinal tract | +++ | ++ | +++ |
| Example 36 | 62 | 450 | 527 | 77 | gastrointestinal tract | +++ | +++ | +++ |
| Example 37 | 66 | 586 | 661 | 75 | blood vessel, nose, and gastrointestinal tract | +++ | ++ | ++ |
| Example 38 | 67 | 568 | 712 | 144 | blood vessel | +++ | +++ | +++ |
| Example 39 | 68 | 602 | 667 | 65 | gastrointestinal tract | +++ | +++ | +++ |
| Example 40 | 69 | 600 | 656 | 56 | gastrointestinal tract | +++ | +++ | +++ |
| Example 41 | 72 | 583 | 668 | 85 | gallbladder and gastrointestinal tract | +++ | +++ | +++ |
| Example 42 | 73 | 598 | 726 | 128 | nose | +++ | +++ | +++ |
| Example 43 | 76 | 592 | 671 | 79 | gastrointestinal tract and lower abdomen | +++ | +++ | +++ |
| Example 44 | 77 | 614 | 669 | 55 | nose | +++ | +++ | +++ |
| Example 45 | 78 | 619 | 683 | 64 | nose, gallbladder, and gastrointestinal tract | +++ | +++ | +++ |
| Example 46 | 79 | 674 | 724 | 50 | nose and gastrointestinal tract | +++ | +++ | +++ |
| Example 47 | 81 | 552 | 702 | 150 | gastrointestinal tract | +++ | +++ | +++ |
| Example 48 | 88 | 535 | 655 | 120 | nose | +++ | +++ | +++ |
| Example 49 | 102 | 551 | 673 | 122 | gastrointestinal tract | +++ | +++ | +++ |
| Example 50 | 103 | 567 | 702 | 135 | gastrointestinal tract | +++ | +++ | +++ |
| Example 51 | 105 | 451 | 530 | 79 | liver and gastrointestinal tract | +++ | ++ | +++ |
| Example 52 | 108 | 479 | 600 | 121 | blood vessel, liver, gallbladder, and gastrointestinal tract | +++ | +++ | +++ |
| Example 53 | 116 | 486 | 606 | 120 | blood vessel, gallbladder, and gastrointestinal tract | +++ | ++ | +++ |
| Example 58 | 109 | 440 | 600 | 160 | liver and gastrointestinal tract | +++ | +++ | +++ |
| Example 59 | 115 | 520 | 640 | 120 | blood vessel, gallbladder, and gastrointestinal tract | +++ | +++ | +++ |
| Example 60 | 123 | 564 | 651 | 87 | gallbladder and gastrointestinal tract | +++ | +++ | +++ |
| Example 61 | 124 | 605 | 618 | 13 | nose | +++ | +++ | +++ |
| Example 62 | 127 | 564 | 651 | 87 | blood vessel, liver, and gastrointestinal tract | +++ | +++ | +++ |
| Example 63 | 128 | 530 | 690 | 160 | blood vessel, liver, and gastrointestinal tract | +++ | ++ | +++ |
| Example 64 | 129 | 522 | 611 | 89 | blood vessel, gallbladder, and gastrointestinal tract | +++ | +++ | +++ |
| Example 65 | 130 | 541 | 619 | 78 | blood vessel, liver, and gastrointestinal tract | +++ | +++ | +++ |
| Example 66 | 131 | 440 | 580 | 140 | liver and gastrointestinal tract | +++ | +++ | +++ |

TABLE 1-continued

| | Dye | Excitation wavelength λex | Fluorescence emission wavelength λem | Stokes' shift λex – λem | Site(s) to be labelled | Staining property | Fluorescence sensitivity | Storage stability |
|---|---|---|---|---|---|---|---|---|
| Example 67 | 132 | 530 | 680 | 150 | blood vessel | +++ | +++ | +++ |
| Example 68 | 133 | 510 | 690 | 180 | blood vessel | +++ | +++ | +++ |
| Example 69 | 134 | 440 | 600 | 160 | blood vessel | +++ | +++ | +++ |
| Example 70 | 135 | 430 | 600 | 170 | blood vessel | +++ | +++ | +++ |
| Example 71 | 136 | 560 | 760 | 200 | gastrointestinal tract | +++ | +++ | +++ |
| Example 72 | 137 | 590 | 700 | 110 | gallbladder and gastrointestinal tract | +++ | +++ | +++ |
| Example 73 | 138 | 540 | 690 | 150 | gastrointestinal tract | +++ | +++ | +++ |
| Example 74 | 139 | 570 | 640 | 70 | nose | +++ | +++ | +++ |
| Example 75 | 140 | 510 | 650 | 140 | gastrointestinal tract | +++ | +++ | +++ |
| Example 76 | 141 | 380 | 490 | 110 | gastrointestinal tract | +++ | +++ | +++ |
| Example 77 | 142 | 530 | 680 | 150 | gastrointestinal tract | +++ | +++ | +++ |
| Example 78 | 110 | 623 | 671 | 48 | blood vessel | +++ | +++ | +++ |

*Dye numbers refer to numbers of the compounds described as specific examples.

TABLE 2

| | Dye | Excitation wavelength λex | Fluorescence emission wavelength λem | Stokes' shift λex – λem | Site(s) to be labelled | Staining property | Fluorescence sensitivity | Storage stability |
|---|---|---|---|---|---|---|---|---|
| Comaprative Example 1 | ICG | 784 | 811 | 27 | liver | +++ | + | – |
| Comaprative Example 2 | fluorescein | 494 | 521 | 27 | blood vessel | +++ | ++ | ++ |

As is clear from Tables 1 and 2, the probe for a biological specimen of the present invention can effectively label a specific site in a body tissue. In addition, the probe for a biological specimen of the present invention has excellent spectral characteristics and exhibits excellent storage stability. Further, in the staining with conventionally known dyes described in, for example, Comparative Examples 1 and 2, only a single site can be labelled. In contrast, many of the probes of the present invention can simultaneously label multiple sites with one probe. In this case, multiple sites can be simultaneously monitored, and hence, the amount of the probe to be required becomes the smallest, resulting in a cost reduction. Further, the probe of the present invention can label a specific site with high contrast, and hence can precisely image morphological features such as a size and a shape. In particular, the imaging of a disease-related site and the monitoring of its time-dependent change are particularly useful. Further, Zebrafish has slight intrinsic fluorescence in the abdomen, but there is almost no intrinsic fluorescence in the other sites. An individual labelled with the staining agent of the present invention exhibits remarkable staining property and fluorescence sensitivity compared with an individual to which a probe is not exposed, and hence, the form of a tissue can be clearly visualized. Different sites of Zebrafish could not be labelled until such a low molecular weight compound of the present invention is used. In addition, the use of Zebrafish as a model animal allows the screening in a short time and at a low cost.

Example 79

[Ex Vivo Labelling with Probe for Biological Specimen]
Zebrafish which had been stained by the operation in Example 5 was taken out and fixed with a 4% solution of paraformaldehyde (PFA) in PBS. After that, a tissue section having a thickness of 50 μm was prepared with a linear slicer PRO7 (manufactured by Dosaka EM Co., Ltd.) (Table 3). The section was collected on an MAS-coated slide glass (manufactured by Matsunami Glass Ind., Ltd.), mounted with Fluoromount G (manufactured by Southern Biotechnology), and then covered with a cover glass. The obtained slide was observed with a fluorescence stereomicroscope (MZ16FA manufactured by Leica Microsystems K.K.) and an inverted fluorescence microscope (Axiovert 200M manufactured by Carl Zeiss, Inc.).

Examples 80 and 81

[In Vitro Labelling with Probe for Biological Specimen]
A human frozen tissue section slide (manufactured by BioChain Institute, Inc.) shown in Table 3 was immersed in a 10 ng/mL aqueous solution of each of the staining compounds shown in Table 3 for 1 hour. Next, the slide was washed three times with PBS for 10 minutes, mounted with Fluoromount G (manufactured by Southern Biotechnology), and then covered with a cover glass. The slide was observed with a fluorescence stereomicroscope (MZ16FA manufactured by Leica Microsystems K.K.) and an inverted fluorescence microscope (Axiovert 200M manufactured by Carl Zeiss, Inc.) to evaluate the staining property and fluorescence intensity.

Table 3 shows the results of Examples 79 to 81.

TABLE 3

| | Dye | Biological specimen | Staining property | Fluorescence sensitivity |
|---|---|---|---|---|
| Example 79 | 6 | Zebrafish liver section | +++ | +++ |
| Example 80 | 18 | human small intestine section | +++ | +++ |
| Example 81 | 23 | human liver tumor section | +++ | +++ |

As clear from Table 3, the probe of the present invention can label a tissue of a biological specimen with both ex vivo staining and in vitro staining, and is excellent in staining property and fluorescence sensitivity, and thus, can clearly visualize the tissue.

INDUSTRIAL APPLICABILITY

There is provided the probe for a biological specimen for labelling a biological specimen in a simple manner and with high sensitivity, which exhibits high storage stability and has a large Stokes' shift. The probe for a biological specimen can effectively label different specific sites of the respective body tissues and organs, based on a difference in partial structures thereof. In the present invention, the effective labelling of specific sites enables the imaging of morphological features such as a size and a shape. In particular, the imaging of a disease-related site and the monitoring of its time-dependent change enable the progression and cure of a disease to be objectively evaluated. The probe is also applicable to a technology of selectively imaging a specific body tissue at a molecular level. Further, the speed of drug discovery including screening becomes faster, with the result that a cost reduction can be achieved. The probe is also applicable to the development of high precision diagnosis and treatment method for new diseases. Further, it is expected to use the probe as an index in screening for a safety evaluation of a chemical substance. In addition, the probe for a biological specimen of the present invention is used for a life science research to understand unexplained phenomena, for example, with the result that, the probe for a biological specimen of the present invention may become an effective basic technology that dramatically develops the industry.

The present invention is not limited to the above embodiments and various changes and modifications can be made within the spirit and scope of the present invention. Therefore to apprise the public of the scope of the present invention, the following claims are made.

This application claims the benefit of Japanese Patent Application No. 2008-330987, filed Dec. 25, 2008, which is hereby incorporated by reference herein in its entirety.

The invention claimed is:

1. A labelling method, wherein one of staining and differential staining is performed by bringing a biological specimen into contact with a composition comprising a probe for a biological specimen comprising, as an active agent, at least one member among the following formulae

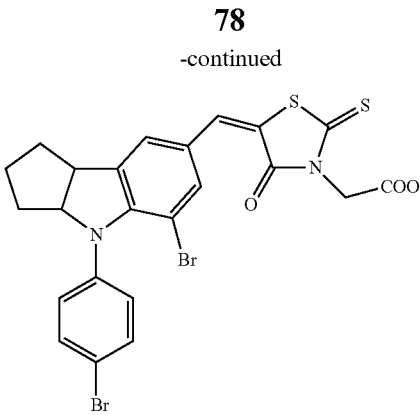

(1)

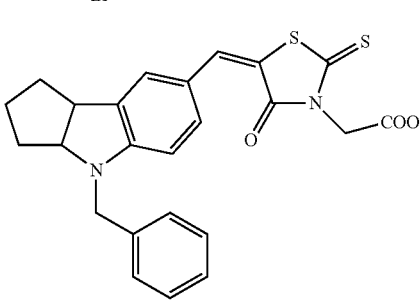

(2)

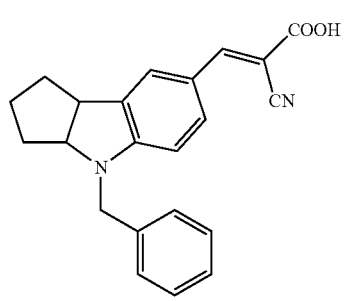

(3)

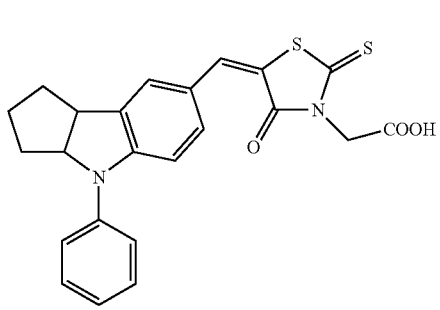

(5)

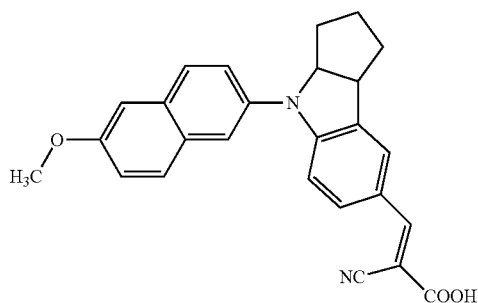

(6)

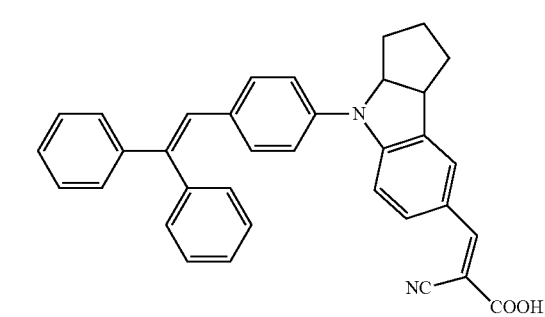

(7)

-continued
(11)
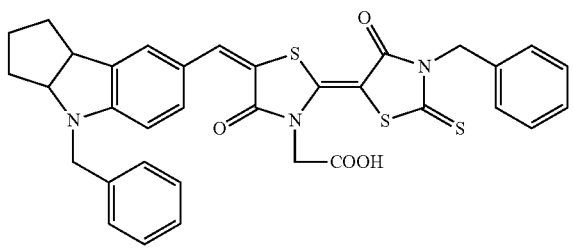
(13)
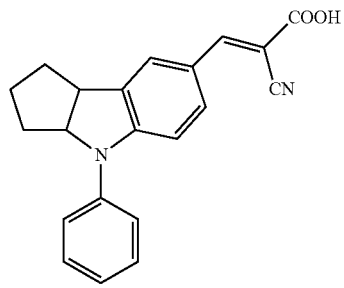
(14)
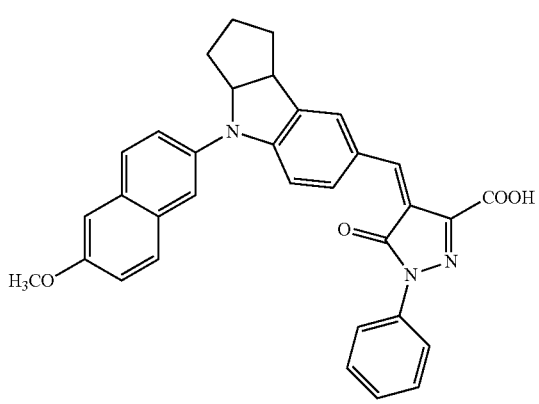
(17)
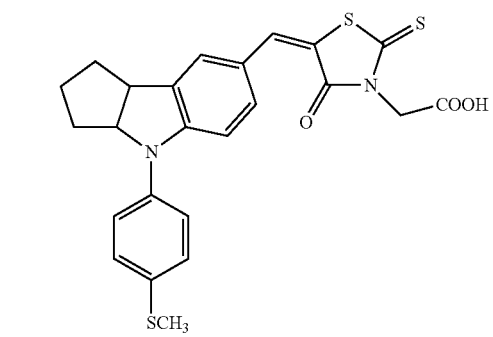
(18)
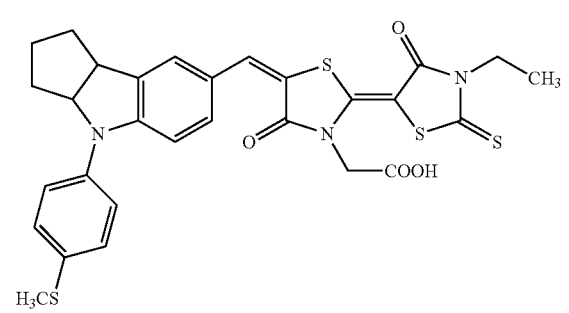
-continued
(20)
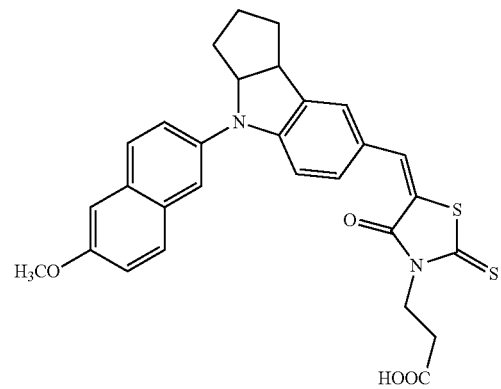
(22)
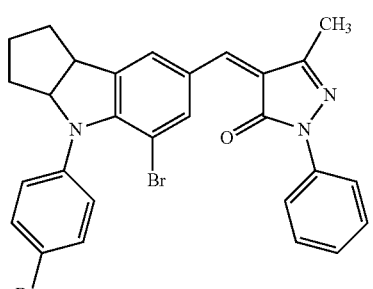
(23)
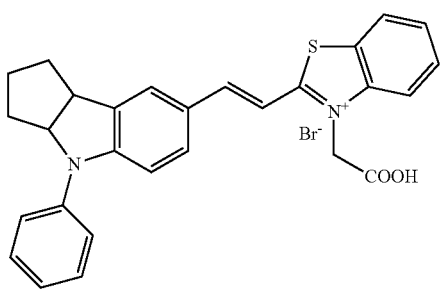
(24)
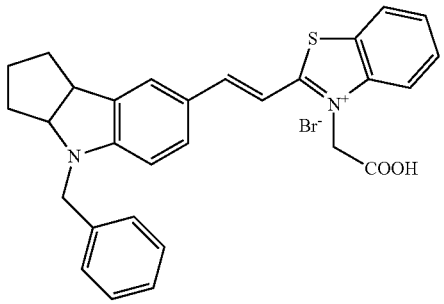
(25)
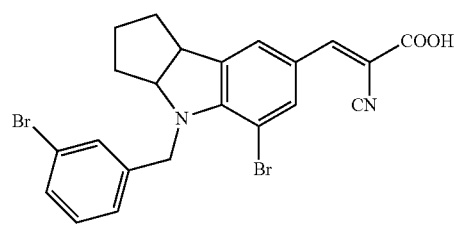

-continued
(29)
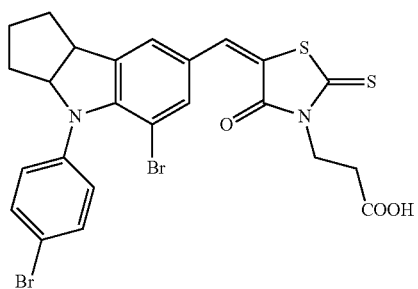
(30)
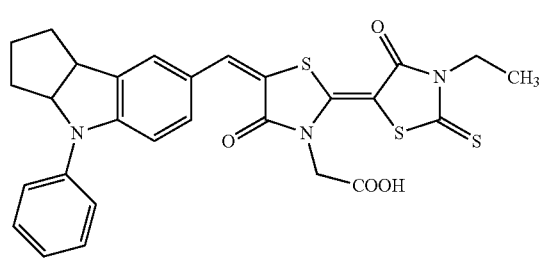
(31)
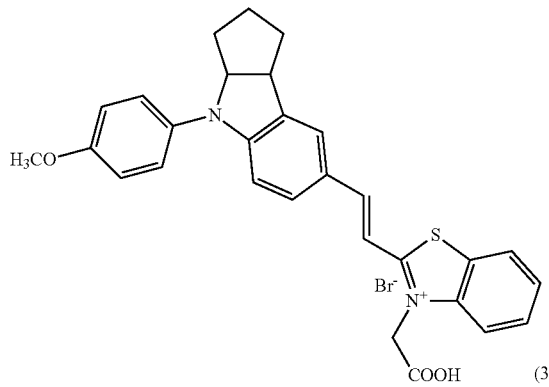
(34)
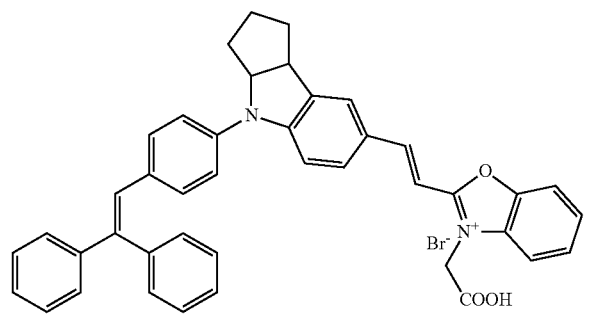
(35)
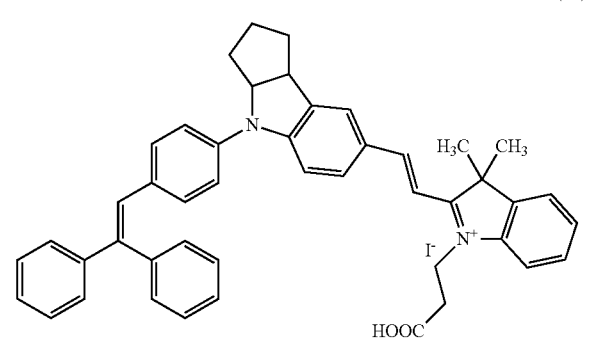
-continued
(37)
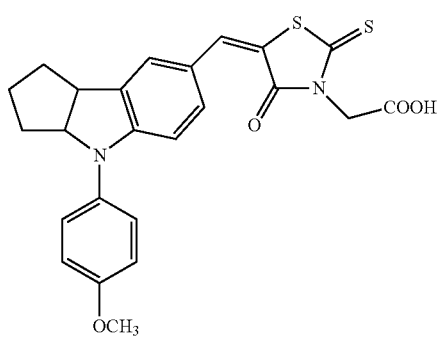
(38)
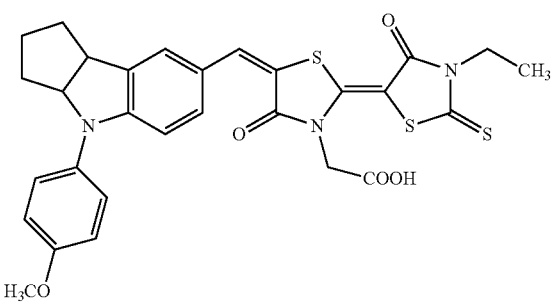
(40)
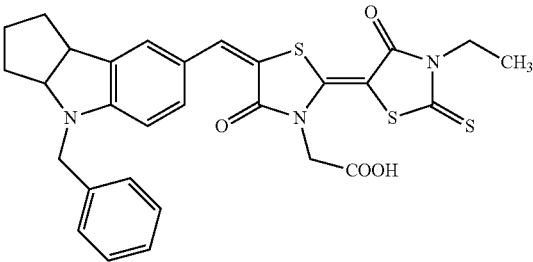
(42)
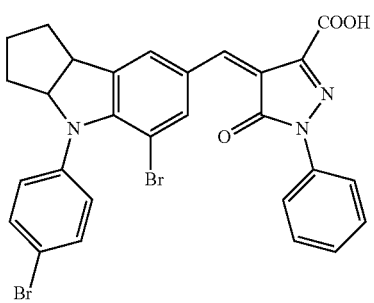
(43)
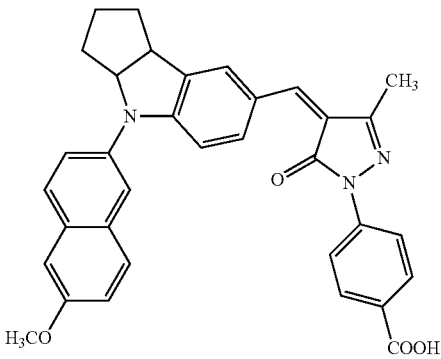

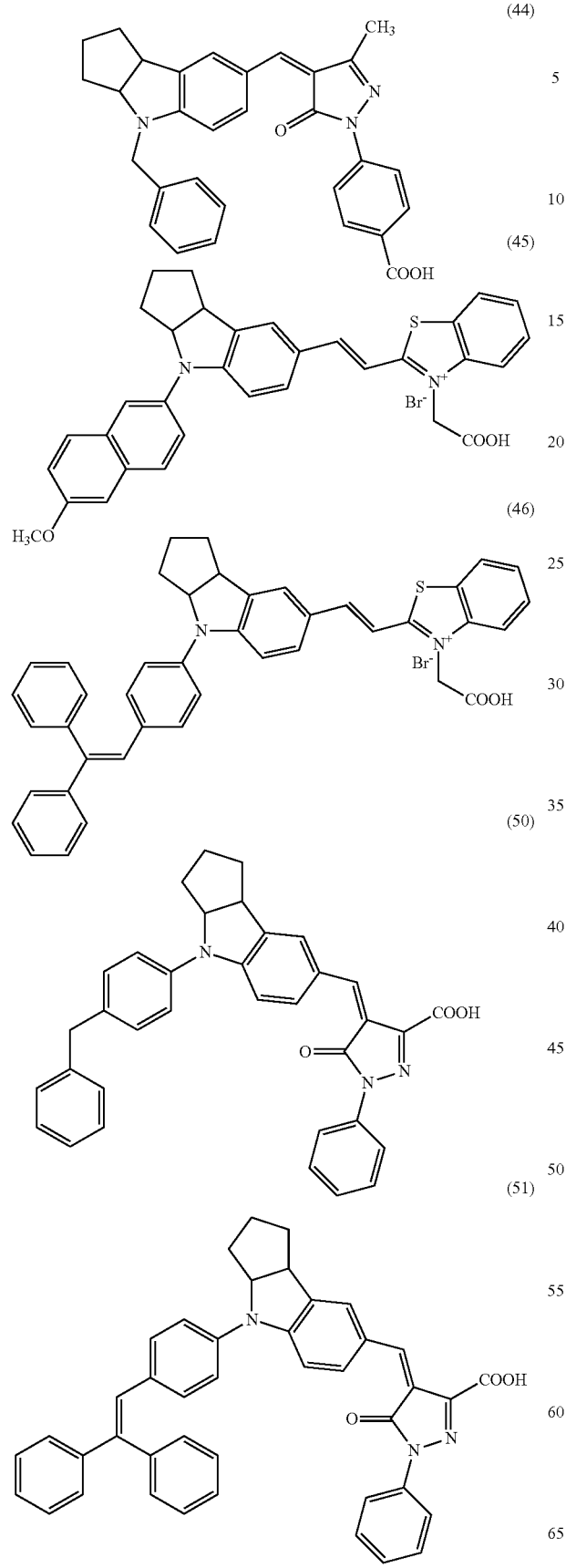
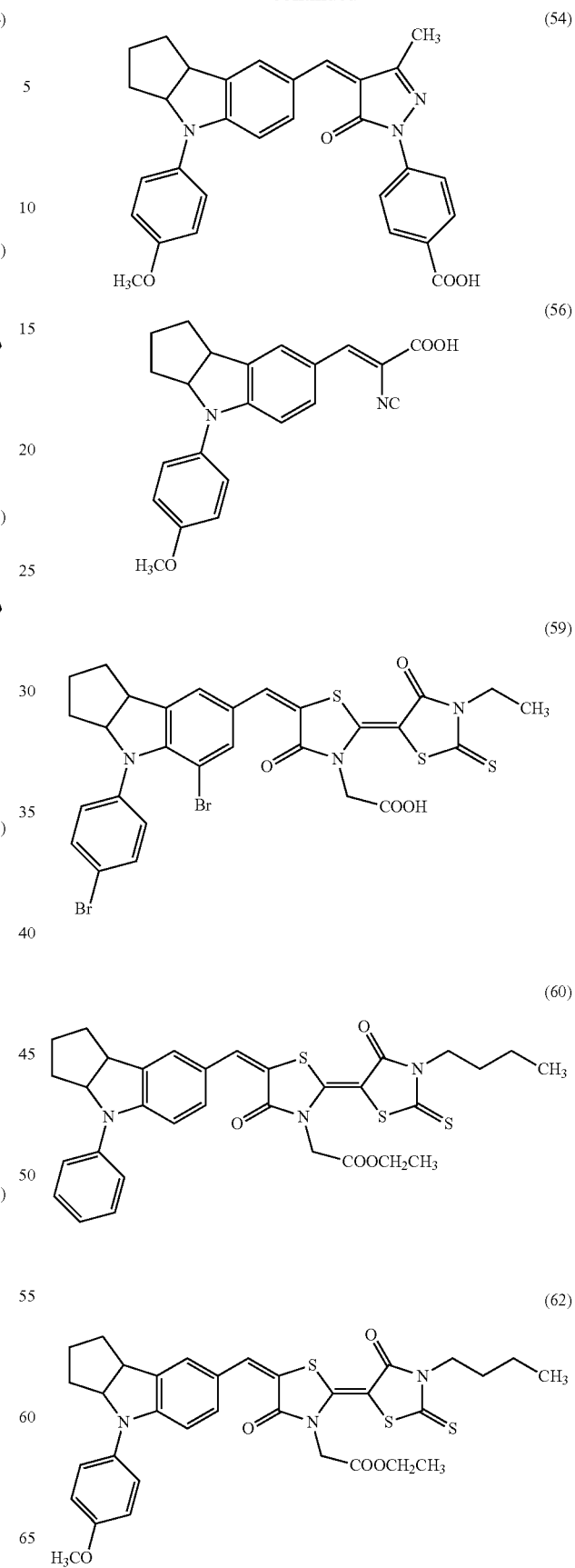

85
-continued
(66)
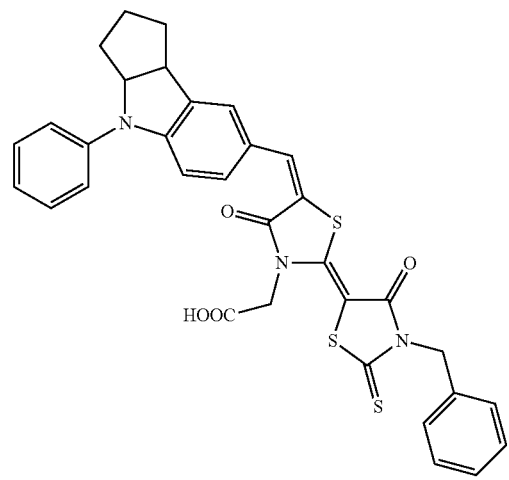
(67)
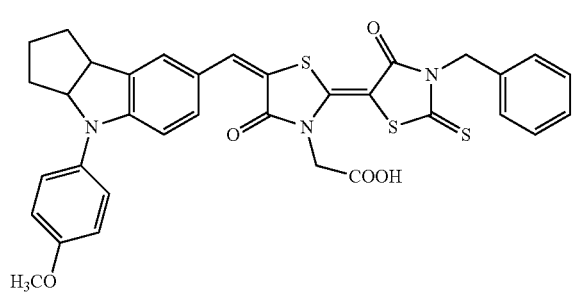
(68)
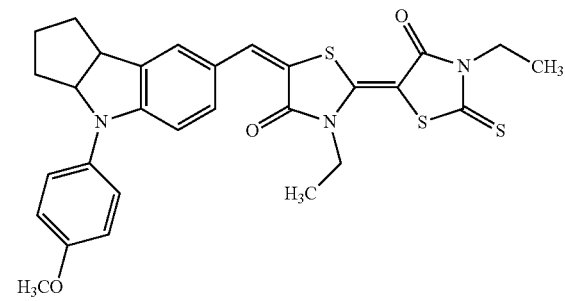
(69)
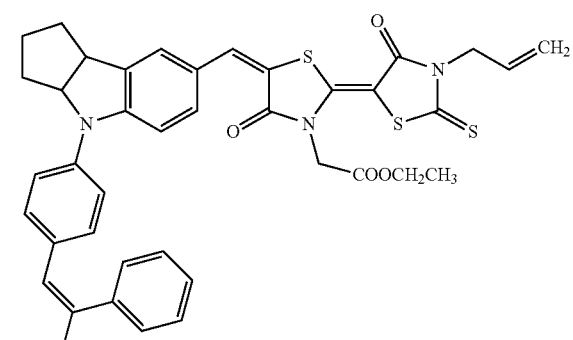
86
-continued
(72)
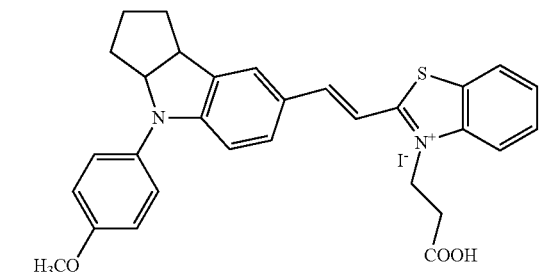
(73)
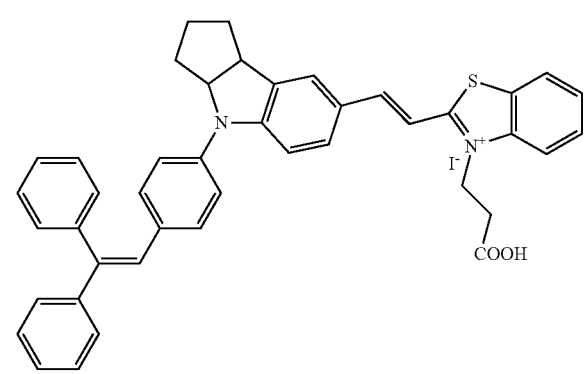
(76)
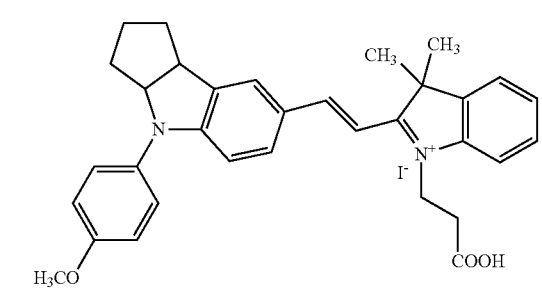
(77)
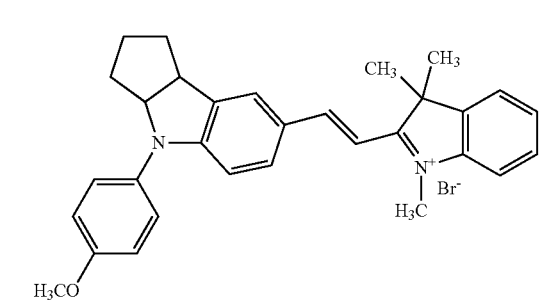
(78)
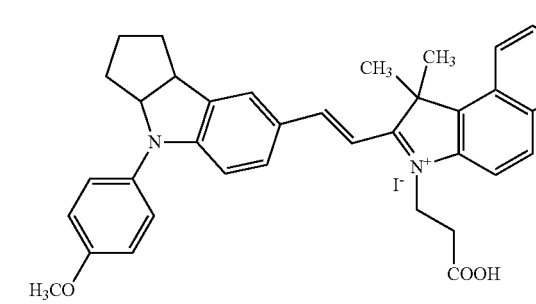

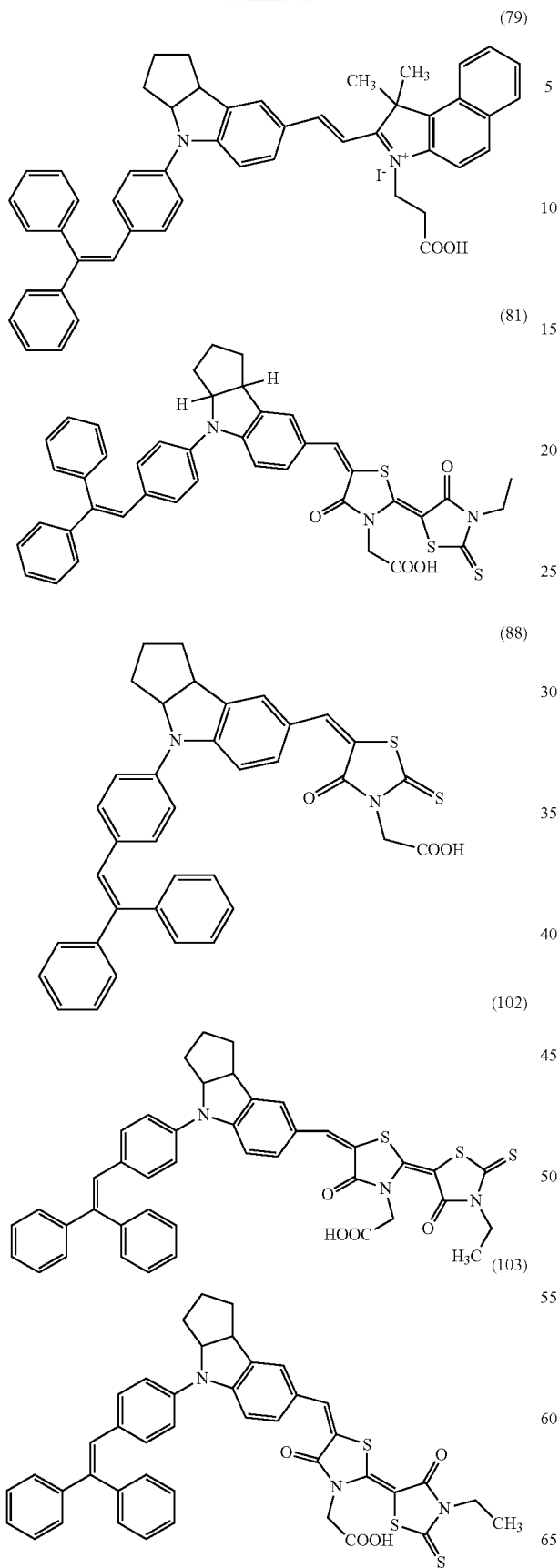
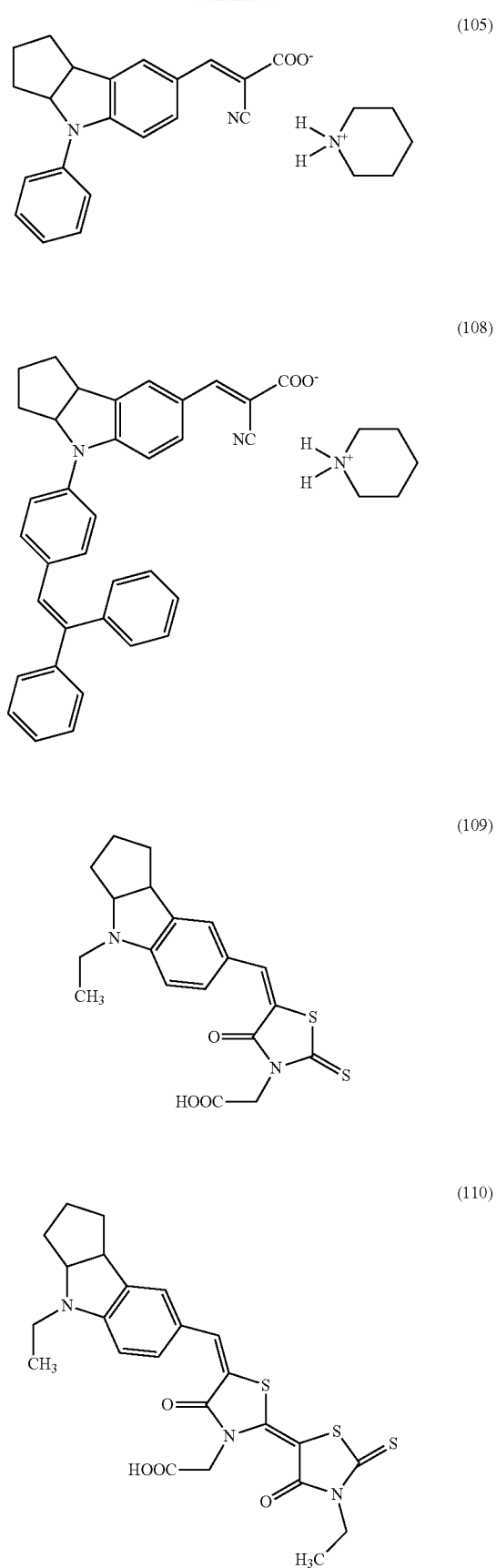

(115)
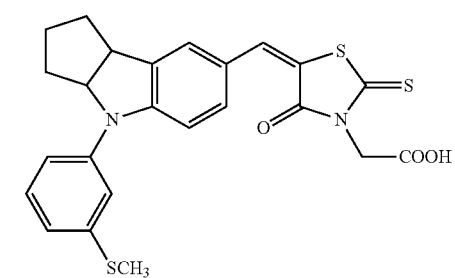
(116)
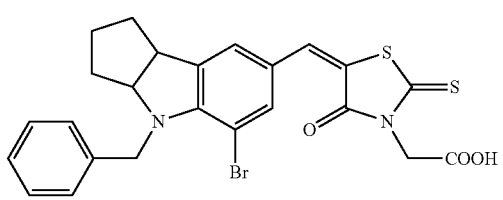
(123)
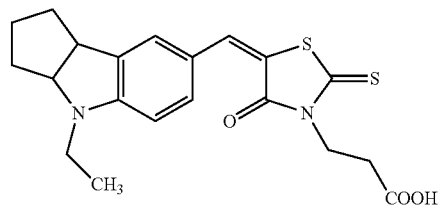
(124)
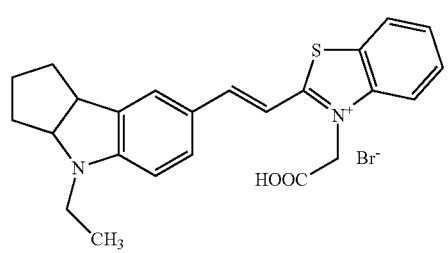
(127)
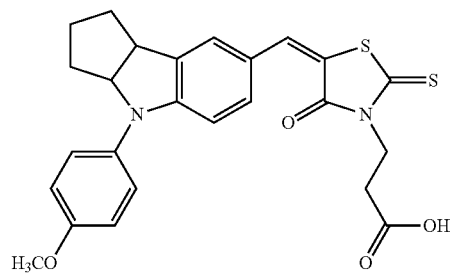
(128)
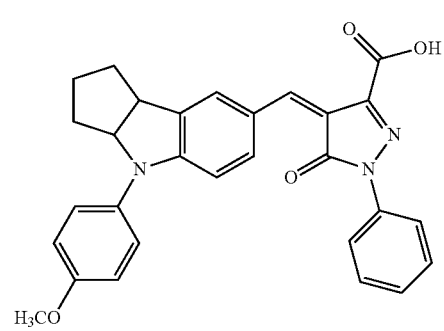
(129)
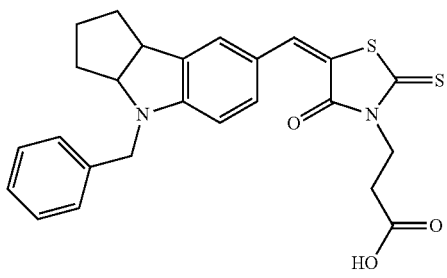
(130)
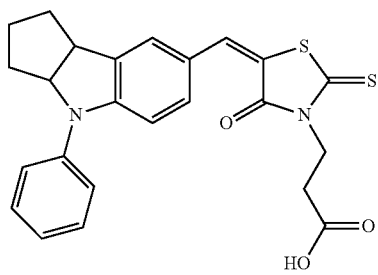
(131)
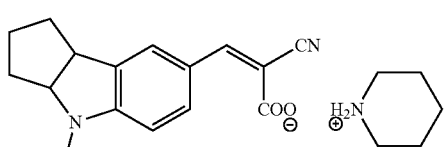
(132)
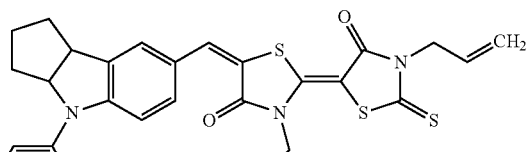
(133)
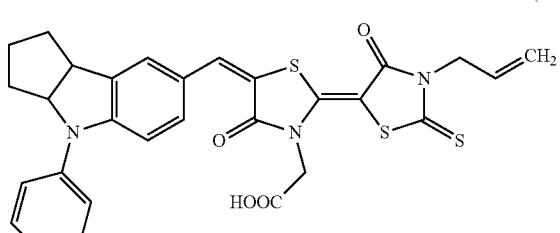
(134)
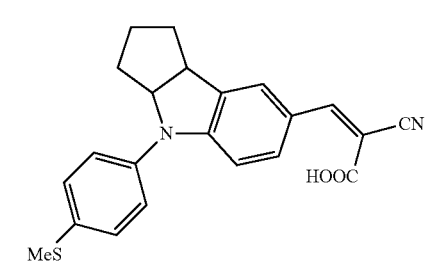

(135)
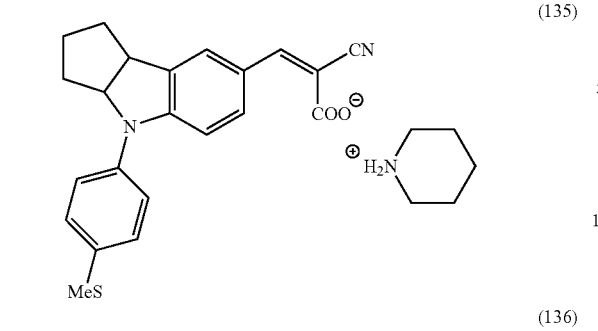

(136)
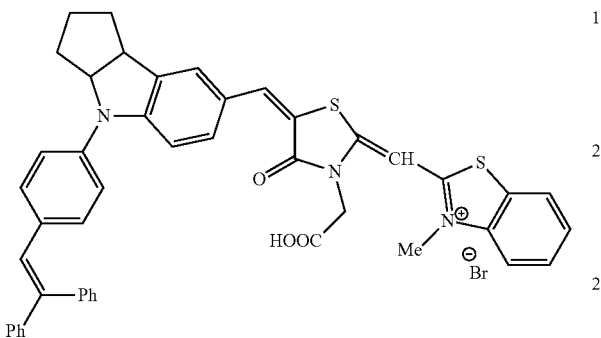

(137)
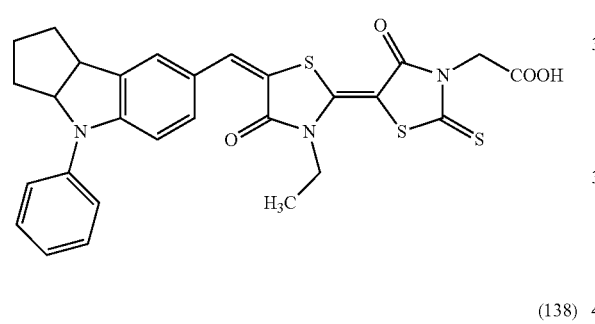

(138)
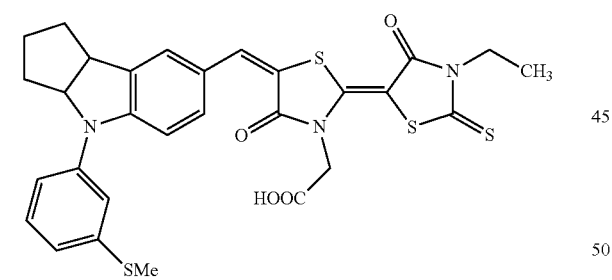

(139)
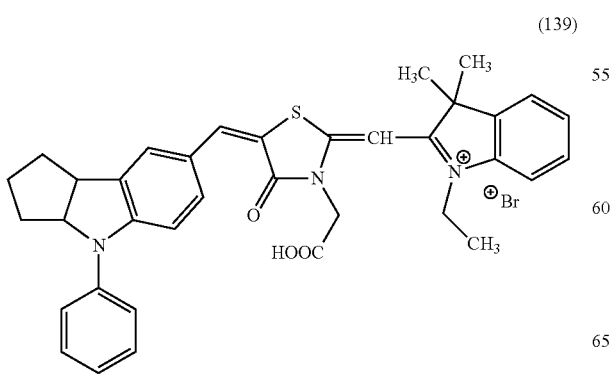

(140)
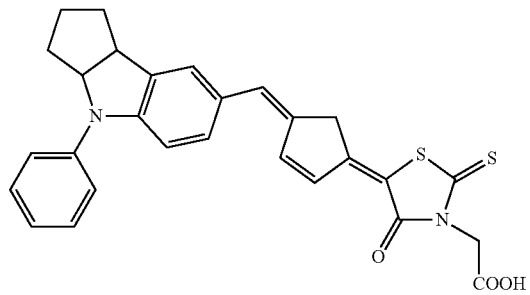

(141)
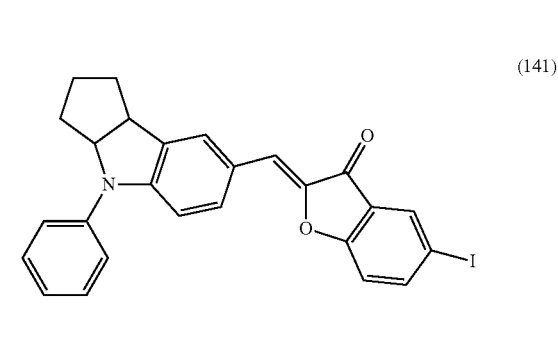

(142)
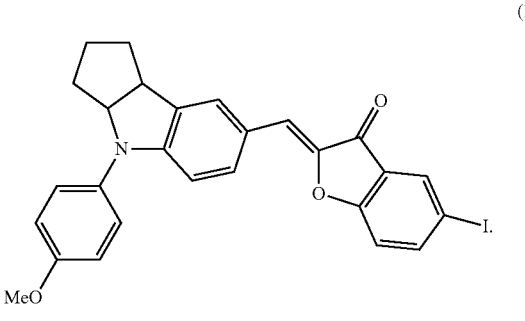

2. A labelling method according to claim 1, wherein the biological specimen is used in vivo.

3. A method, comprising the steps of applying to a sample a composition for dyeing a biological specimen; and
determining whether or not said biological specimen is dyed, wherein
said composition comprises a probe for said biological specimen comprising, as an active agent, at least one member among the following formulae (1)
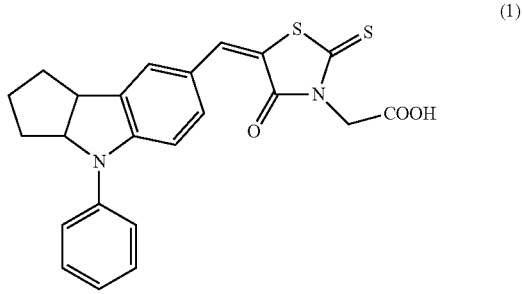

-continued
(2)
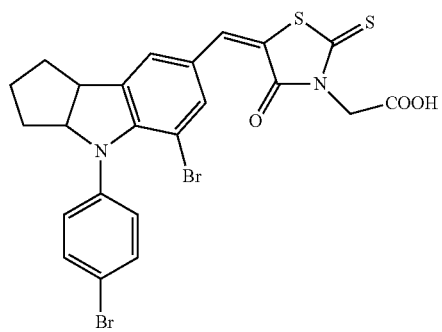
(3)
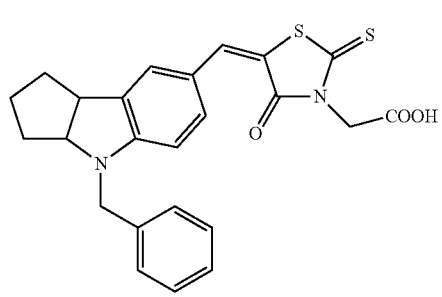
(5)
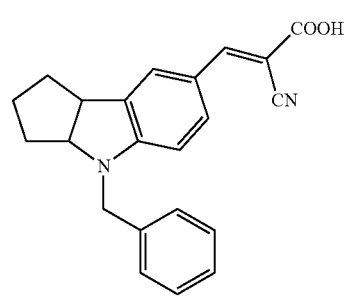
(6)
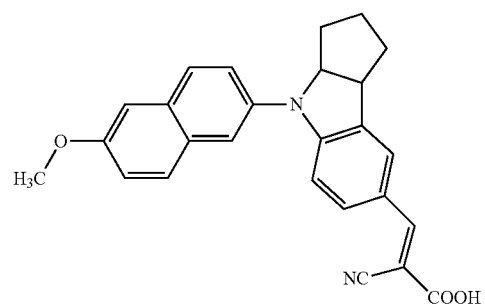
(7)
-continued
(11)
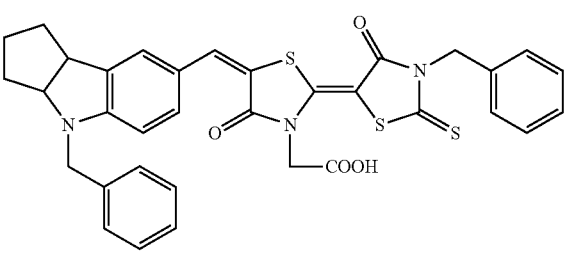
(13)
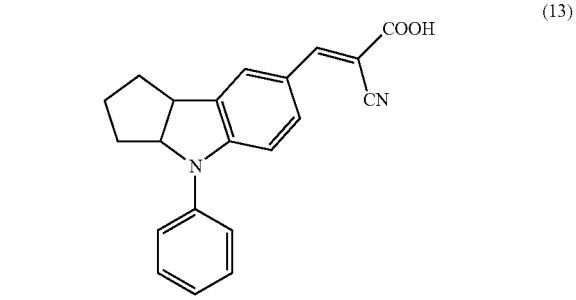
(14)
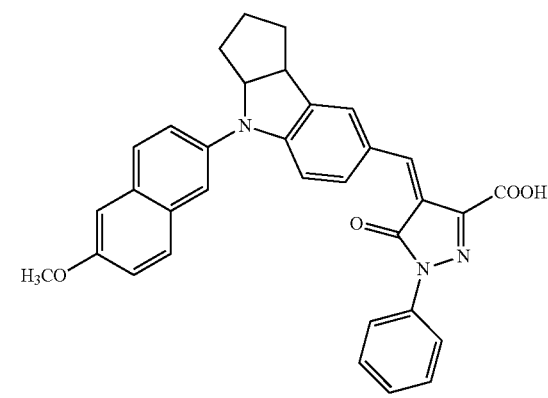
(17)
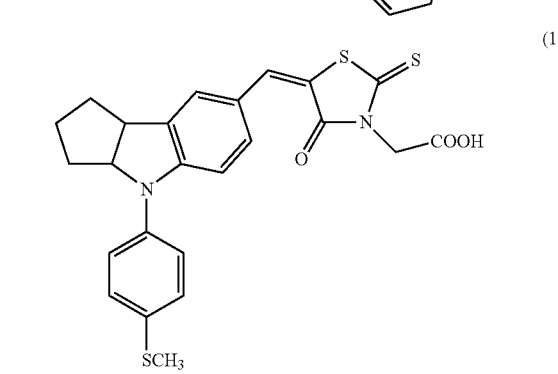
(18)
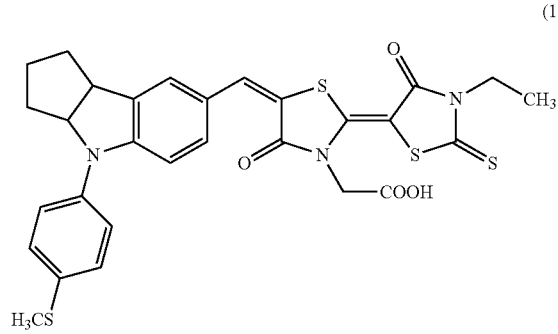

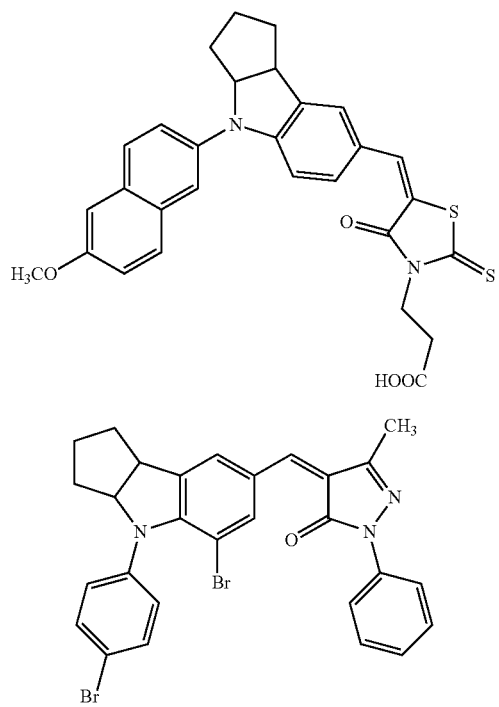
(20)
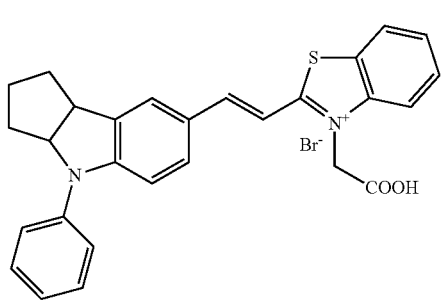
(22)
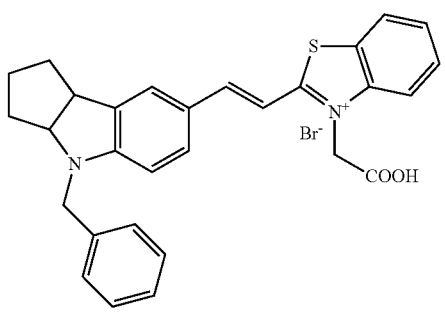
(23)
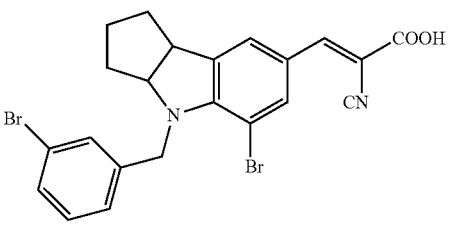
(24)
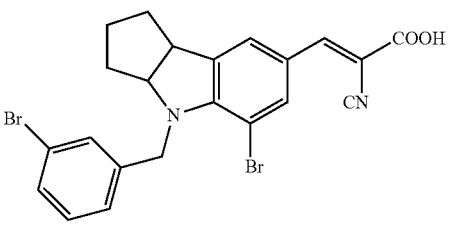
(25)
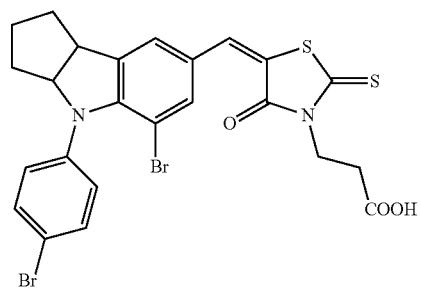
(29)
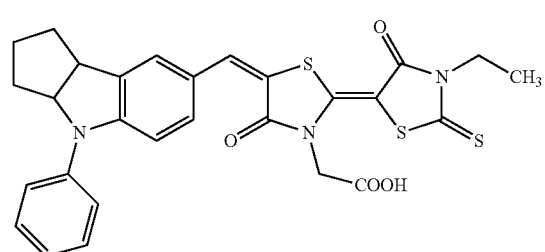
(30)
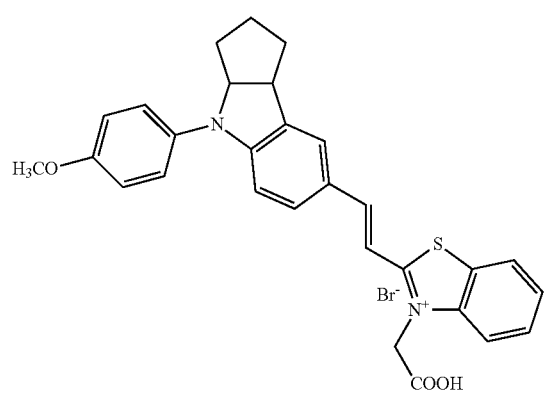
(31)
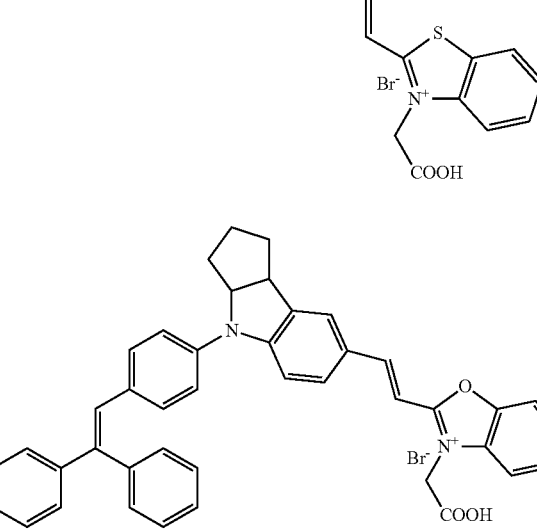
(34)
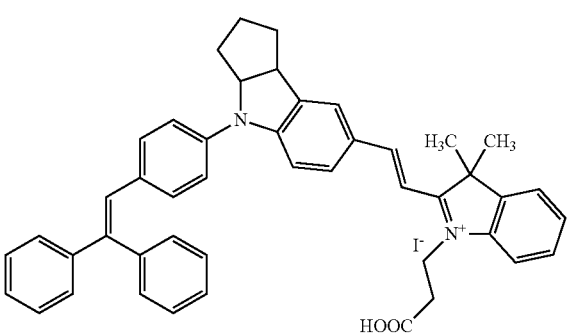
(35)

97
-continued
(37)
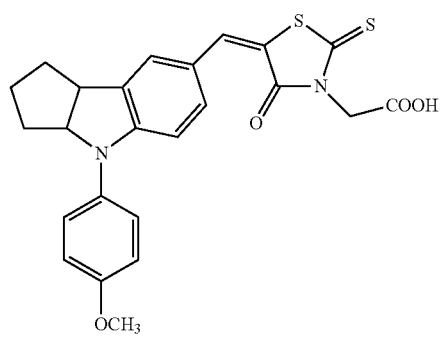
(38)
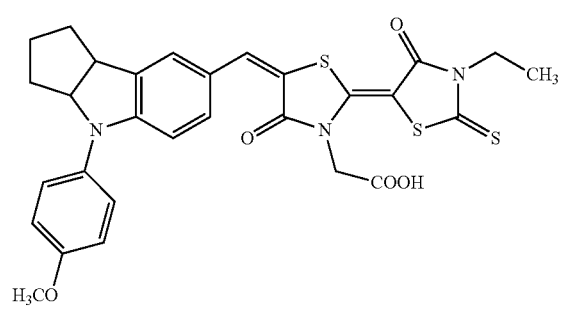
(40)
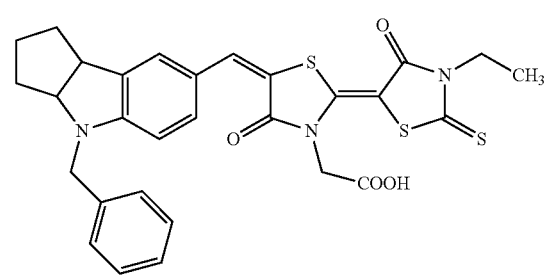
(42)
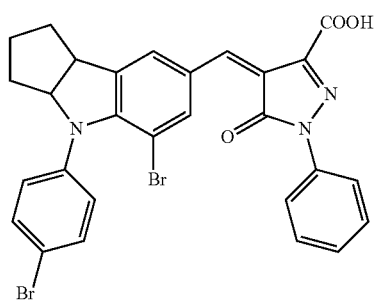
(43)
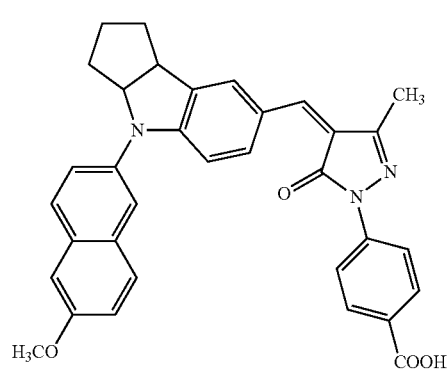
98
-continued
(44)
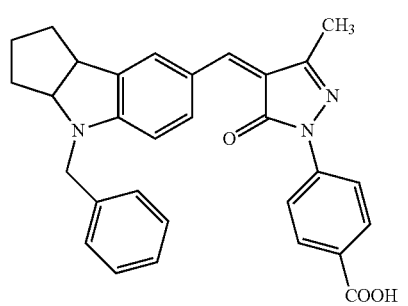
(45)
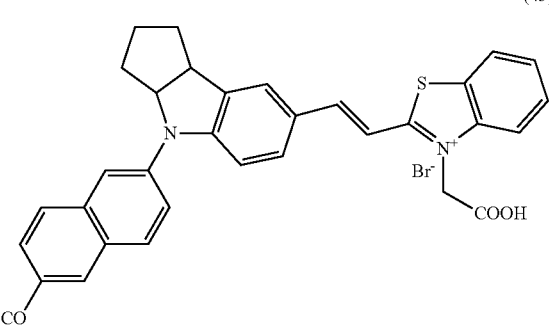
(46)
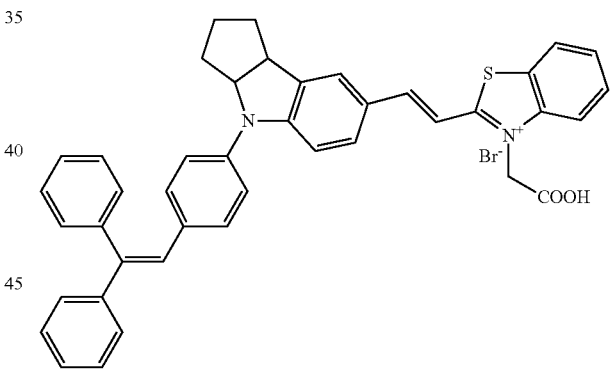
(50)
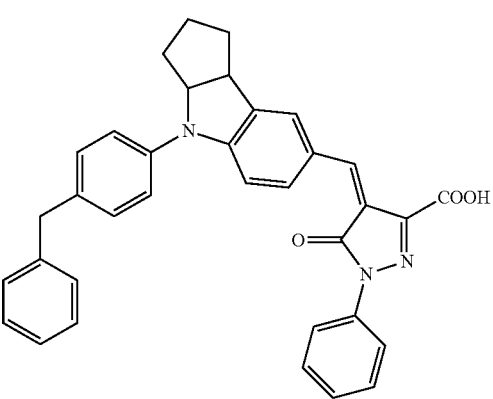

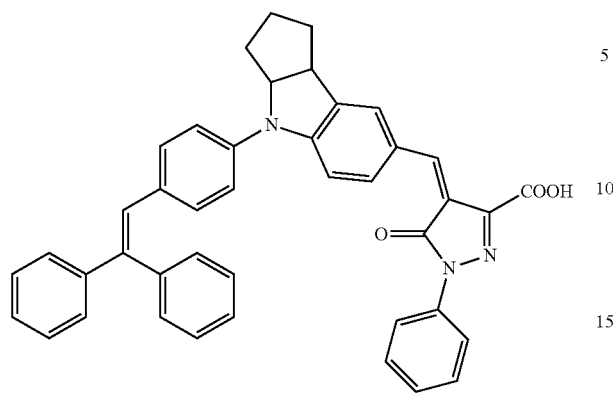
(51)
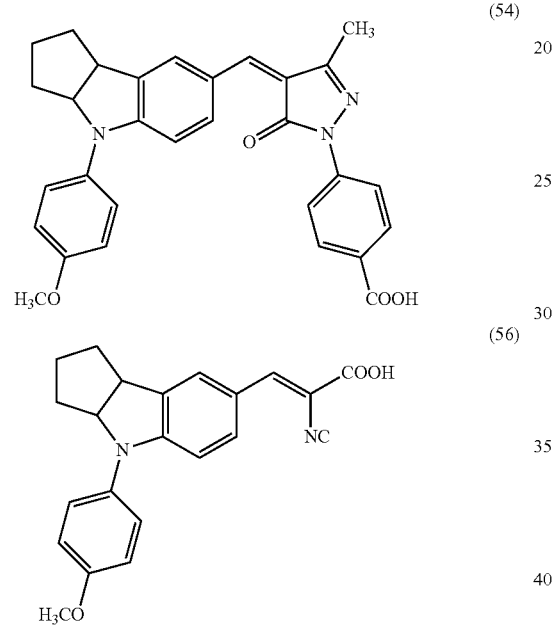
(54)
(56)
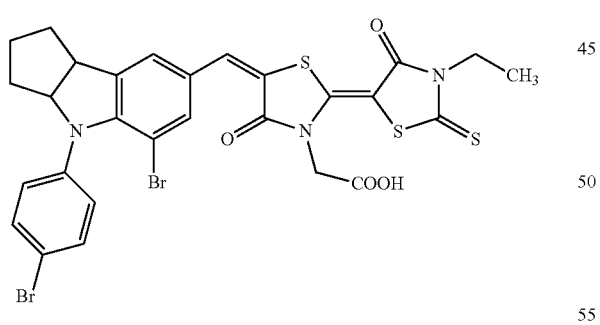
(59)
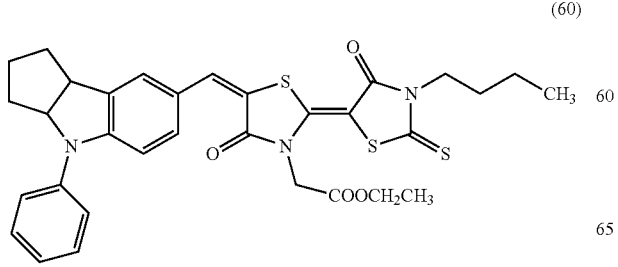
(60)
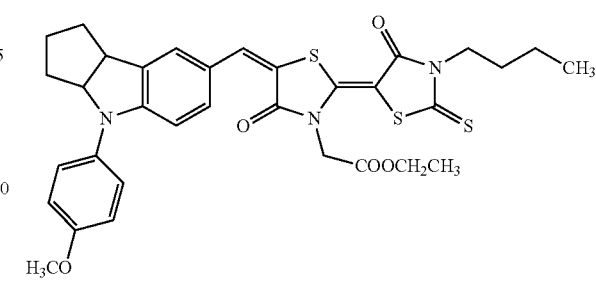
(62)
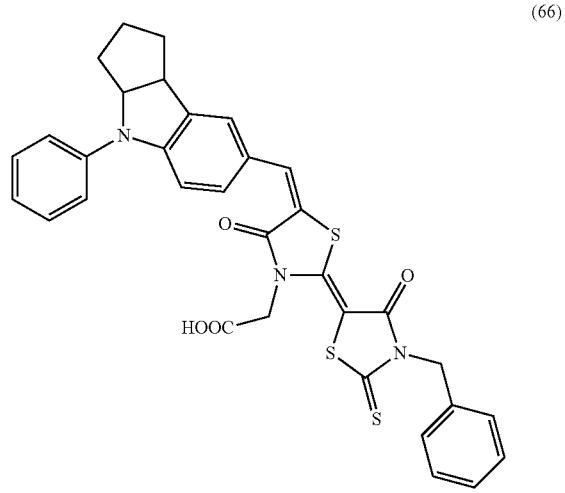
(66)
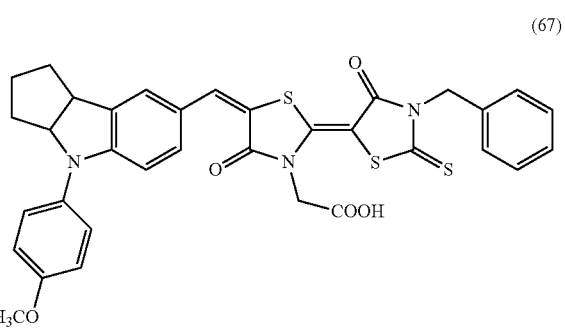
(67)
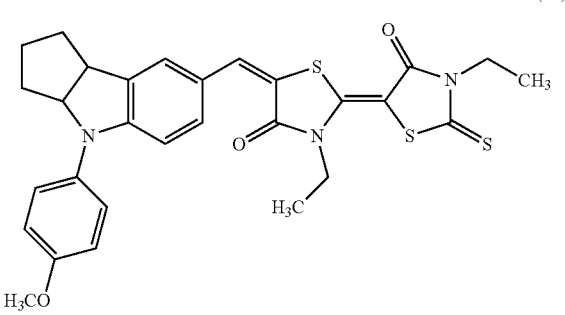
(68)

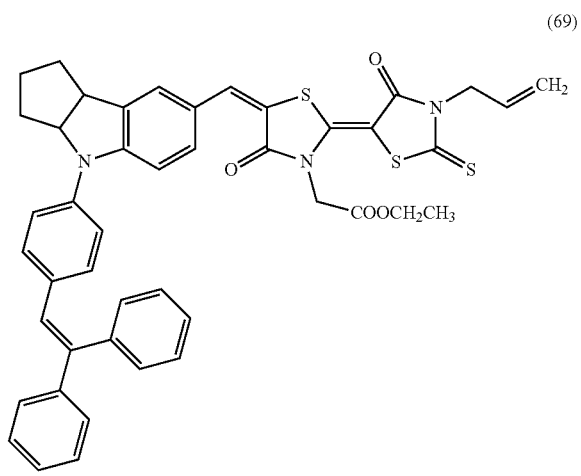
(69)
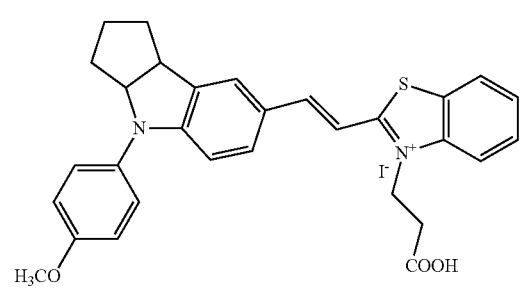
(72)
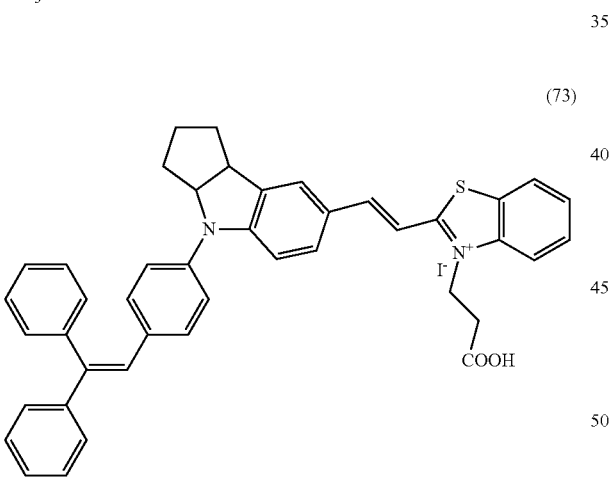
(73)
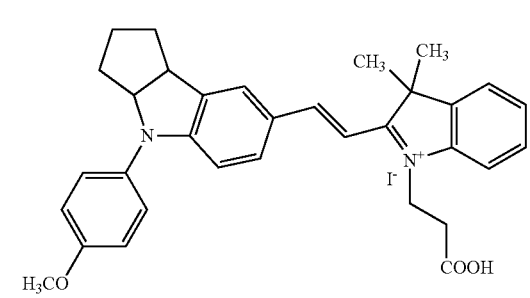
(76)
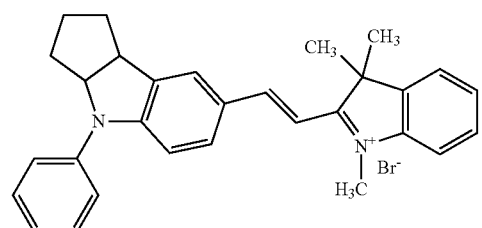
(77)
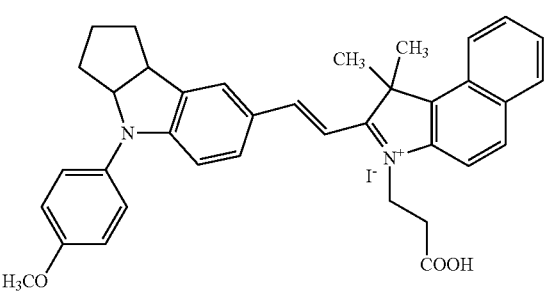
(78)
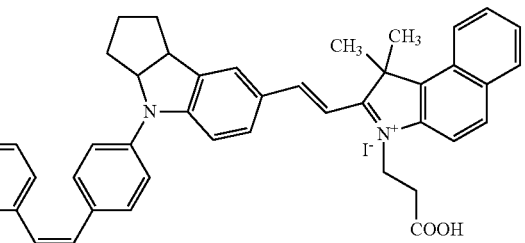
(79)
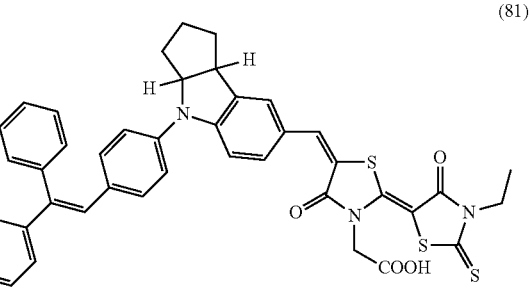
(81)

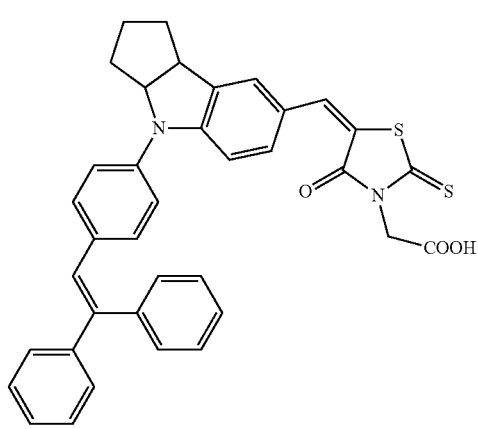
(88)
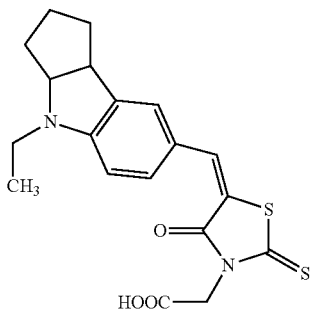
(109)
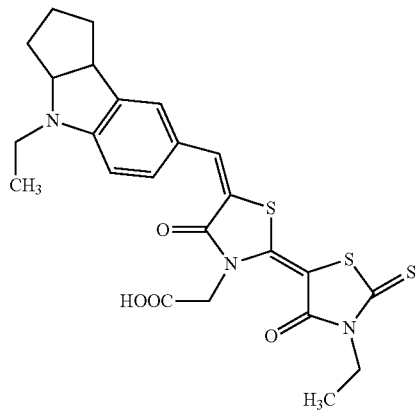
(102)
(110)
(103)
(115)
(105)
(108)
(116)
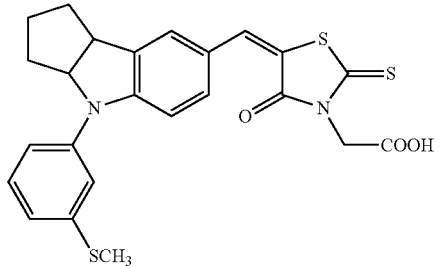
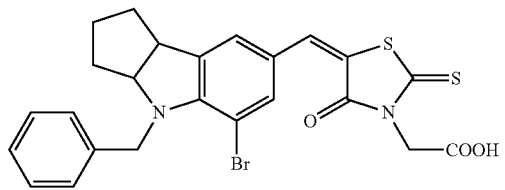
(123)
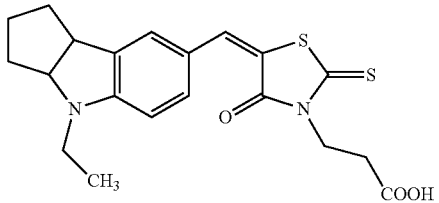

-continued
(124)
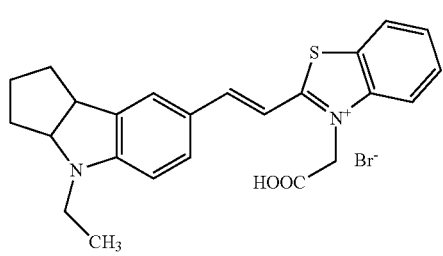
(127)
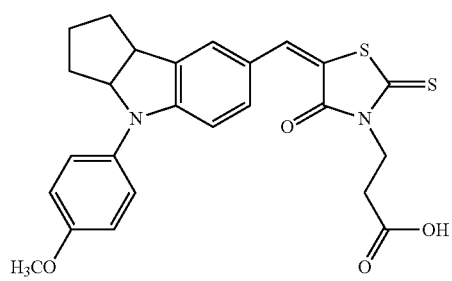
(128)
(129)
(130)
-continued
(131)
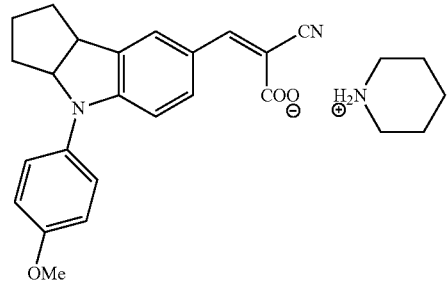
(132)
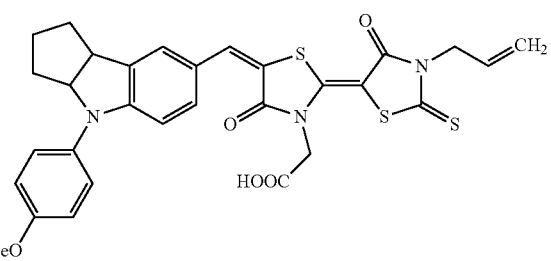
(133)
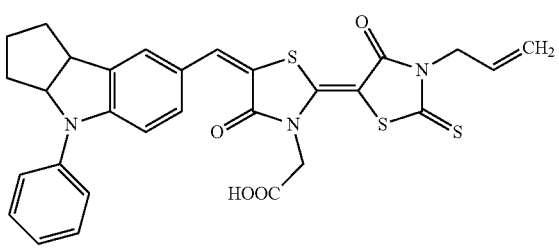
(134)
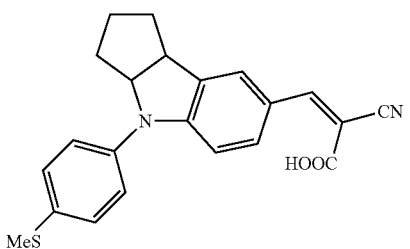
(135)
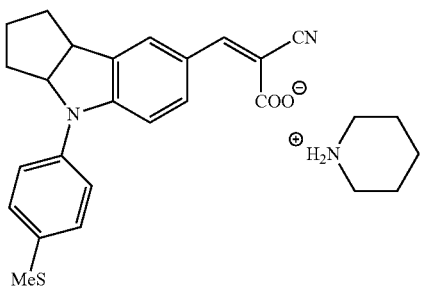

-continued (136)

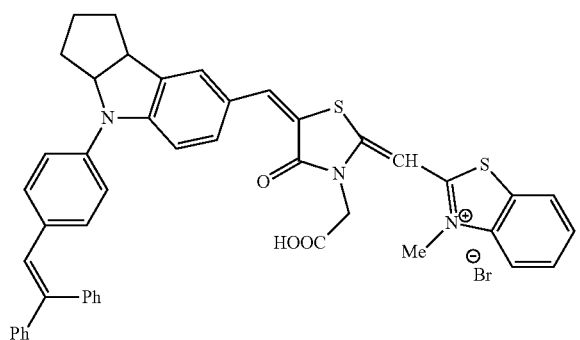

(137)

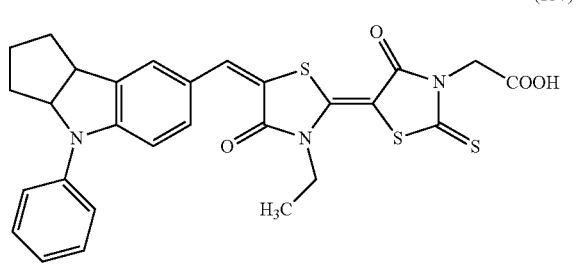

(138)

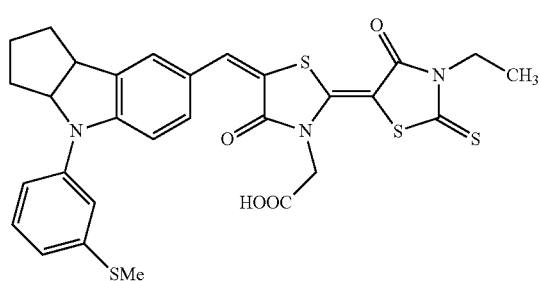

(139)

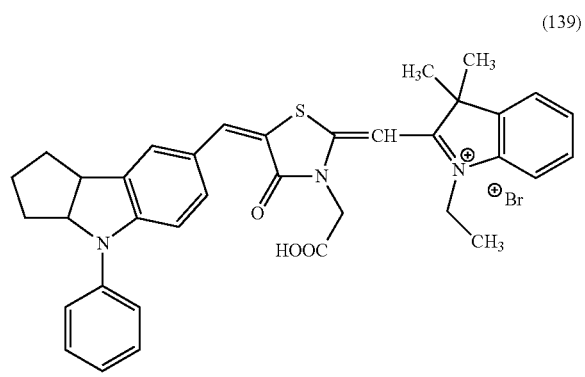

-continued (140)

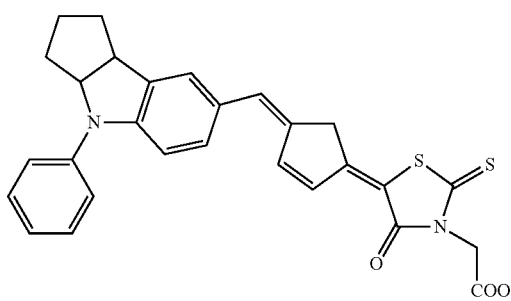

(141)

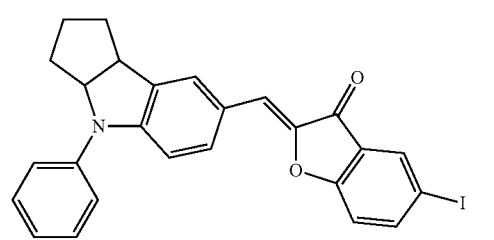

(142)

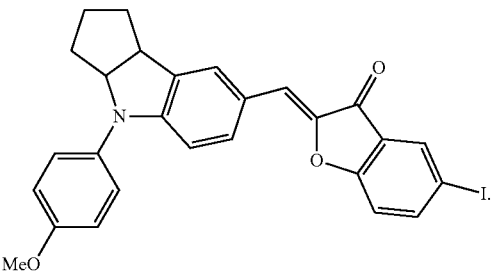

4. A method according to claim 3, wherein the biological specimen is a small bony fish.

5. A method according to claim 4, wherein the small bony fish comprises Zebrafish.

6. A labelling method according to claim 1, wherein the composition further comprises dimethyl sulfoxide.

7. A method according to claim 3, wherein the composition further comprises dimethyl sulfoxide.

8. A labelling method according to claim 1, which is carried out on the biological specimen in vitro.

9. A labelling method according to claim 1, which is carried out on the biological specimen ex vivo.

10. A labelling method according to claim 2, wherein the labelling method is performed in vivo with an individual organism, a microorganism, protozoan, a biological tissue, a biological tissue section, a human cell or an animal cell.

11. A method according to claim 8, wherein the labelling method is performed in vitro with a biological tissue, a biological tissue section, a human cell or an animal cell.

12. A method according to claim 9, wherein the labelling method is performed ex vivo with a biological tissue, a biological tissue section, a human cell or an animal cell.

* * * * *